United States Patent
Varasi et al.

(10) Patent No.: US 8,980,877 B2
(45) Date of Patent: *Mar. 17, 2015

(54) SPIROCYCLIC DERIVATIVES AS HISTONE DEACETYLASE INHIBITORS

(75) Inventors: Mario Varasi, Milan (IT); Florian Thaler, Gerenzano (IT); Raffaella Amici, Codogno (IT); Agnese Abate, Philadelphia, PA (US); Maria Carmela Fulco, Milan (IT); Saverio Minucci, Noverasco di Opera (IT); Ciro Mercurio, Legnano (IT)

(73) Assignee: DAC S.R.L., Milan (IT)

( * ) Notice: Subject to any disclaimer, the term of this patent is extended or adjusted under 35 U.S.C. 154(b) by 293 days.

This patent is subject to a terminal disclaimer.

(21) Appl. No.: 13/446,861

(22) Filed: Apr. 13, 2012

(65) Prior Publication Data

US 2012/0258949 A1  Oct. 11, 2012

Related U.S. Application Data

(63) Continuation-in-part of application No. 12/988,197, filed as application No. PCT/EP2009/054376 on Apr. 14, 2009, now Pat. No. 8,592,444.

(30) Foreign Application Priority Data

Apr. 15, 2008 (EP) .................................. 08154528
Oct. 13, 2009 (EP) .................................. 09172856
Oct. 11, 2010 (WO) ................ PCT/EP2010/065176

(51) Int. Cl.
| | | |
|---|---|---|
| A61K 31/407 | (2006.01) |
| A61K 31/438 | (2006.01) |
| A61K 31/55 | (2006.01) |
| C07D 491/107 | (2006.01) |
| A61K 31/397 | (2006.01) |
| A61K 31/537 | (2006.01) |
| C07D 498/10 | (2006.01) |

(52) U.S. Cl.
CPC .............. *A61K 31/397* (2013.01); *A61K 31/407* (2013.01); *A61K 31/438* (2013.01); *A61K 31/537* (2013.01); *A61K 31/55* (2013.01); *C07D 491/107* (2013.01); *C07D 498/10* (2013.01)
USPC .......... 514/210.19; 540/543; 544/71; 546/17; 548/407; 548/409; 548/950

(58) Field of Classification Search
CPC . A61K 31/397; A61K 31/407; A61K 31/438; C07D 498/10; C07D 491/107
USPC ....... 540/543; 544/71; 546/17; 548/407, 409, 548/950; 514/210.19
See application file for complete search history.

(56) References Cited

FOREIGN PATENT DOCUMENTS

| WO | 2007/113249 A2 | 10/2007 |
| WO | 2007/136605 A2 | 11/2007 |
| WO | 2009/127609 A1 | 10/2009 |

OTHER PUBLICATIONS

International Search Report from PCT/EP2010/065176 dated May 11, 2011 (3 pages).
Written Opinion from PCT/EP2010/065176 dated May 11, 2011 (6 pages).
James R Davie, "Covalent modifications of histones: expression from chromatin templates," Current Opinion in Genetics & Development, 1998, 173-178, vol. 8, Current Biology Ltd ISSN 0959-437X.
Jiansheng Wu et al., "25 years after the nucleosome model: chromatin modifications," TIBS 25, Dec. 2000, 619-623, Elsevier Science Ltd.
S. Timmermann et al., "Histone acetylation and disease," CMLS, Cell. Mol. Life Sci., 2001, 728-736, vol. 58, Birkhauser Verlag, Basel.
Lili Huang, "Targeting Histone Deacetylases for the Treatment of Cancer and Inflammatory Diseases," Journal of Cellular Physiology, 2006, 611-616, vol. 209, Wiley-Liss, Inc.
Saverio Minucci et al., "Histone deacetylase inhibitors and the promise of epigenetic (and more) treatments for cancer," Nature Reviews—Cancer, Jan. 2006, 38-51, vol. 6, Nature Publishing Group.

(Continued)

*Primary Examiner* — Rita Desai
(74) *Attorney, Agent, or Firm* — McCormick, Paulding & Huber, LLP

(57) ABSTRACT

This invention is related to new histone deacetylase inhibitors according to the general formula (I), wherein: m and n are independently zero or an integer from 1 to 4; p is zero or an integer from 1 to 3, with the proviso that when p is zero, n and m cannot be both 1; R is hydrogen; $C_1$-$C_6$ alkyl, optionally substituted by $C_3$-$C_8$ cycloalkyl, $C_6$-$C_{10}$ aryl or hetero($C_2$-$C_9$) aryl; (CO)$R^2$; (SO$_2$)$R^3$; $C_3$-$C_8$ cycloalkyl; $C_6$-$C_{10}$ aryl; or hetero($C_2$-$C_9$)aryl; $R^1$ is halogen, $C_1$-$C_6$ alkyl, $C_1$-$C_6$ haloalkyl, $C_1$-$C_6$ alkoxy, $C_1$-$C_6$ haloalkoxy; Y is $CH_2$ or $NR^4$; Z is C=$R^5$; and $R^2$, $R^3$, $R^4$, and $R^5$ are as further defined in the specification; and pharmaceutical acceptable salts thereof.

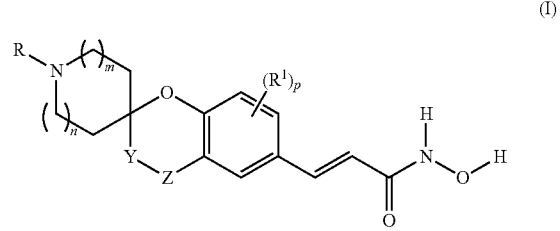

7 Claims, No Drawings

(56) References Cited

OTHER PUBLICATIONS

Mehdi Ouaissi et al., "Histone Deacetylase Enzymes as Potential Drug Targets in Cancer and Parasitic Diseases" Journal of Biomedicine and Biotechnology, 2006, 1-10, vol. 2006, Article ID 13474, Hindawi Publishing Corporation.

Rajiv P. Sharma et al., "Valproic acid and chromatin remodeling in schizophrenia and bipolar disorder: Preliminary results from a clinical population," Schizophrenia Research, 2006, 227-231, vol. 88, Elsevier B. V.

MA Glozak et al., "Histone deacetylases and cancer," Oncogene, 2007, 5420-5432, vol. 26, Nature Publishing Group.

Greetje Elaut et al., "The Pharmaceutical Potential of Histone Deacetylase Inhibitors," Current Pharmaceutical Design, 2007, 2584-2620, vol. 13, Bentham Science Publishers Ltd.

Konstantin V. Balakin et al., "Histone Deacetylase Inhibitors in Cancer Therapy: Latest Developments, Trends and Medicinal Chemistry Perspective," Anti-Cancer Agents in Medicinal Chemistry, 2007, vol. 7(4), Bentham Science Publishers Ltd.

HB Lee et al., "Histone deacetylase inhibitors: A novel class of therapeutic agents in diabetic nephropathy," Kidney International, 2007, S61-S66, vol. 72, International Society of Nephrology.

B. E. Morrison et al., "Histone deacetylases: Focus on the nervous system," Cell. Mol. Life. Sci., 2007, 2258-2269, vol. 64, Birkhauser Verlag, Basel.

Aleksey G. Kazantsev et al., "Therapeutic application of histone deacetylase inhibitors for central nervous system disorders," Nature Reviews/Drug Discovery, Oct. 2008, 854-868, vol. 7, Macmillan Publishers Limited.

David M Vigushin et al., "Histone deacetylase inhibitors in cancer treatment," Anti-Cancer Drugs, 2002, 1-13, vol. 13, Lippincott Williams & Wilkins.

Leigh Ellis et al., "Epigenetics in cancer: Targeting chromatin modifications," Mol Cancer Ther, Jun. 2009, 1409-1420, vol. 8(6), American Association for Cancer Research.

Solomon D. Kattar et al., "Parallel medicinal chemistry approaches to selective HDAC1/HDAC2 inhibitor (SHI-1:2) optimization," Bioorganic & Medicinal Chemistry Letters, 2009, 1168-1172, vol. 19, Elsevier Ltd.

Joey L. Methot et al., "SAR profiles of spirocyclic nicotinamide derived selective HDAC1/HDAC2 inhibitors (SHI-1:2)," Bioorganic & Medicinal Chemistry Letters, 2008, 6104-6109, vol. 18, Elsevier Ltd.

Maria A. Halili et al., "Histone Deacetylase Inhibitors in Inflammatory Disease," Current Topics in Medicinal Chemistry, 2009, vol. 9(3), Bentham Science Publishers Ltd.

Dante Rotili et al., "Non-Cancer Uses of Histone Deacetylase Inhibitors: Effects on Infectious Diseases and β-Hemoglobinopathies," Current Topics in Medicinal Chemistry, 2009, vol. 9(3), Bentham Science Publishers Ltd.

Norbert L. Wiech et al., "Inhibition of Histone Deacetylases: A Pharmacological Approach to the Treatment of Non-Cancer Disorders," Current Topics in Medicinal Chemistry, 2009, 257-271, vol. 9(3), Bentham Science Publishers Ltd.

Michael Haberland et al., "The many roles of histone deacetylases in development and physiology: implications for disease and therapy," Nature Reviews/Genetics, Jan. 2009, 32-42, vol. 10, Macmillan Publishers Limited.

Walid Rasheed et al., "Histone deacetylase inhibitors in lymphoma and solid malignancies," Expert Rev. Anticancer Ther., 2008, 413-432, vol. 8(3), Future Drugs Ltd.

SPIROCYCLIC DERIVATIVES AS HISTONE DEACETYLASE INHIBITORS

CROSS REFERENCE TO RELATED APPLICATIONS

This application is a Continuation-In-Part of U.S. patent application Ser. No. 12/988,197 filed on Oct. 15, 2010 and is entitled to the benefit of and incorporates by reference essential subject matter disclosed in European Patent Application No. 08154528.7 filed on Apr. 15, 2008 and International Patent Application No. PCT/EP2009/054376 filed on Apr. 14, 2009. This application is also entitled to the benefit of and incorporates by reference essential subject matter disclosed in in European Patent Application No. 09172856.8 filed on Oct. 13, 2009 and International Patent Application No. PCT/EP2010/065176 filed on Oct. 11, 2010.

FIELD OF THE INVENTION

The present invention relates to inhibitors of histone deacetylases (HDACs), to a process for their preparation, pharmaceutical compositions comprising them, and to their use as therapeutic agents, in particular for the treatment of cancer.

BACKGROUND OF THE INVENTION

The reversible acetylation of the ε-amino groups of several lysine residues in the N-terminal histone tails mediates important conformational modifications in nucleosomes. These modifications influence the access of transcription factors to DNA and regulate gene expression (Davie, J. R. *Curr Opin Genet Dev* 1998, 8, 173-178; Ellis, L. et al. *Mol Cancer Ther* 2009, 8, 1409-1420). Two enzyme classes are involved in the process of acetylation and deacetylation of histones: histone acetyltransferases (HAT), which catalyse histone acetylation by acting as transcriptional co-activators, and histone deacetylases (HDAC).

After their recruitment to the promoter regions induced by transcription repressors and co-repressors such as Sin3, SMRT and N—CoR, histone deacetylases induce the formation of hypoacetylated histones and ultimately lead to transcriptional silencing (Wu, J. et al. *Trends Biochem. Sci.* 2000, 25, 619-623). The aberrant recruitment of histone deacetylases by oncogene proteins, or the disruption of the equilibrium between the activities of histone acetyltransferases and histone deacetylases are implicated in a series of pathologies, such as cancer, diseases of the central and peripheral nervous system, inflammatory diseases, infections, respiratory diseases, immune diseases, cardiovascular diseases, muscular disorders, fibrosis or psoriasis. The following (non exhaustive) selection of references demonstrate the involvement of HDACs in different diseases and the potential therapeutic benefit, which can be achieved by inhibiting them: Timmermann S. et al. *Cell Mol Life Sci.* 2001 58, 728-736; Huang, L. *J. Cell. Physiol.* 2006, 209, 611-616; Minucci, S. et al. *Nature Reviews Cancer,* 2006, 6, 38-51; Ouaissi, M. et al. *J Biomed Biotechnol.* 2006, 1-10; Sharma, P. et al. *Schizophr. Res.* 2006, 88, 227-231; Glozak M. A. et al. *Oncogene.* 2007, 26, 5420-5432; Elaut G. et al. *Curr Pharm Des.* 2007, 13, 2584-2620; Balakin K. V. et al. *Anticancer Agents Med. Chem.* 2007 7, 576-92; Lee H. B. et al. *Kidney Int. Suppl.* 2007, 106, S61-66; Morrison B. E. et al. *Cell Mol Life Sci.* 2007, 64, 2258-2269; Rasheed W. et al. *Expert Rev Anticancer Ther.* 2008, 8, 413-432; Kazantsev A. G. et al. *Nat Rev Drug Discov.* 2008, 7, 854-868; Haberland M. et al. *Nat Rev Genet.* 2009, 10, 32-42; Wiech N. E. et al. *Curr Top Med. Chem.* 2009, 9, 252-271; Rotili D. et al. *Curr Top Med. Chem.* 2009, 9, 272-291; Halili M. A. et al. *Curr Top Med. Chem.* 2009, 9, 309-319.

There has been a considerable effort to develop inhibitors of histone deacetylases in recent years and several classes of compounds have been found to have potent and specific activities in preclinical studies. Their clinical benefits, however, are limited by toxicity problems, poor pharmacokinetic properties, poor potency and lack of selectivity (Elaut G. et al. *Curr Pharm Des.* 2007, 13, 2584-2620; Vigushin, D. et al. *Anti-Cancer Drugs* 2002, 13, 1-13).

PCT applications WO 2007/061880, WO 2007/061978 and WO 2007/136605 (Merck) disclose spirocyclic compounds as HDAC inhibitors. Compounds disclosed in these patents and their biological activities were further described in *Biorg Med Chem Lett* 2008, 18, 6104-6109 and in *Biorg Med Chem Lett* 2009, 19, 1168-1172. Further spirocyclic HDAC inhibitors are disclosed in WO2009/127609.

The inventors have found now that certain substituted spirocyclic derivatives are highly potent inhibitors of the HDAC enzymes.

SUMMARY OF THE INVENTION

According to the present invention there are provided compounds, endowed with a potent HDAC inhibitory activity, of general formula (I)

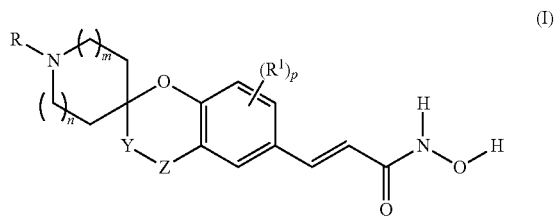

wherein:
m, n are independently zero or an integer from 1 to 4;
P is, zero or an integer from 1 to 3;
R is hydrogen; $C_1$-$C_6$ alkyl, optionally substituted by $C_3$-$C_8$ cycloalkyl, $C_6$-$C_{10}$ aryl, or hetero($C_2$-$C_9$)aryl; $(CO)R^2$; $(SO_2)R^3$; $C_3$-$C_8$ cycloalkyl; $C_6$-$C_{10}$ aryl or hetero($C_2$-$C_9$) aryl;
$R^1$ is halogen, $C_1$-$C_6$ alkyl, $C_1$-$C_6$ haloalkyl, $C_1$-$C_6$ alkoxy, or $C_1$-$C_6$ haloalkoxy;
Y is $CH_2$ or $NR^4$;
Z is $C=R^5$;
$R^2$ is $C_1$-$C_6$ alkyl, optionally substituted by $C_6$-$C_{10}$ aryl or by hetero($C_2$-$C_9$)aryl; $C_6$-$C_{10}$ aryl; hetero($C_2$-$C_9$)aryl; O—$C_1$-$C_6$ alkyl, optionally substituted by $C_6$-$C_{10}$ aryl; O—($C_6$-$C_{10}$-aryl) or $NR^6R^7$;
$R^3$ is $C_1$-$C_6$ alkyl, optionally substituted by $C_6$-$C_{10}$ aryl or by hetero($C_2$-$C_9$)aryl; $C_6$-$C_{10}$ aryl or hetero($C_2$-$C_9$)aryl;
$R^4$ is hydrogen; $C_1$-$C_6$ alkyl, optionally substituted by $C_6$-$C_{10}$ aryl or by hetero($C_2$-$C_9$)aryl;
$R^5$ is oxygen or $NOR^8$;
$R^6$ is hydrogen; $C_1$-$C_6$ alkyl, optionally substituted by $C_6$-$C_{10}$ aryl or by hetero($C_2$-$C_9$)aryl; $C_6$-$C_{10}$ aryl or hetero($C_2$-$C_9$) aryl;
$R^7$ is hydrogen; $C_1$-$C_6$ alkyl, optionally substituted by $C_6$-$C_{10}$ aryl or by hetero($C_2$-$C_9$)aryl; or $R^6$ and $R^7$ together with the nitrogen to which they are bound form a $C_4$-$C_9$-heterocyclic ring, optionally containing one or more further heteroatoms in the ring selected from $NR^9$, O or S;

$R^8$ is hydrogen; $C_1$-$C_6$ alkyl, optionally substituted by $C_6$-$C_{10}$ aryl;

$R^9$ is hydrogen; $C_1$-$C_6$ alkyl, optionally substituted by $C_6$-$C_{10}$ aryl or by hetero($C_2$-$C_9$)aryl; $C_6$-$C_{10}$ aryl; hetero($C_2$-$C_9$)aryl; (CO)$R^{10}$; or (SO$_2$)$R^{11}$;

$R^{10}$ is $C_1$-$C_6$ alkyl, optionally substituted by $C_6$-$C_{10}$ aryl or by hetero($C_2$-$C_9$)aryl; O—$C_1$-$C_6$ alkyl, optionally substituted by $C_6$-$C_{10}$ aryl; O—($C_6$-$C_9$-aryl) or $NR^{12}R^{13}$;

$R^{11}$ is $C_1$-$C_6$ alkyl, optionally substituted by $C_6$-$C_{10}$ aryl or by hetero($C_2$-$C_9$)aryl; $C_6$-$C_{10}$ aryl or hetero($C_2$-$C_9$)aryl;

$R^{12}$ is hydrogen; $C_1$-$C_6$ alkyl, optionally substituted by $C_6$-$C_{10}$ aryl or by hetero($C_2$-$C_9$)aryl; $C_6$-$C_{10}$ aryl or hetero ($C_2$-$C_9$)aryl;

$R^{13}$ is hydrogen; $C_1$-$C_6$ alkyl, optionally substituted by $C_6$-$C_{10}$ aryl or hetero($C_2$-$C_9$)aryl;

and the pharmaceutically acceptable salts thereof; provided that when p is zero, then n and m cannot be both 1.

DETAILED DESCRIPTION OF THE INVENTION

According to the description and claims, "$C_6$-$C_{10}$ aryl" represents a mono or bicyclic aromatic ring system of, respectively, 6, 9 or 10 atoms, such as benzene, indene and naphthalene and includes also indan and tetrahydronaphthalene.

According to the description and claims, "hetero($C_2$-$C_9$) aryl" represents a mono or bicyclic heteroaromatic ring system of, respectively, 5 to 10 members, which contains one, two or three heteroatoms selected from nitrogen, oxygen or sulphur. Examples of said hetero($C_2$-$C_9$)aryls include, but are not limited to: pyrrolyl, furyl, thienyl, pyrazolyl, imidazolyl, oxazolyl, thiazolyl, 1,2,3-oxadiazolyl, 1,3,4-thiadiazolyl, pyridyl, pyridazinyl, pyrimidinyl, pyrazinyl, indolyl, isoindolyl, benzo[b]furanyl, benzo[b]thienyl, benzopyranyl, indazolyl, benzimidazolyl, purinyl, quinolyl, isoquinolyl, quinazolinyl, and quinoxalinyl.

The $C_6$-$C_{10}$ aryl and hetero($C_2$-$C_9$)aryl may be optionally substituted with one or more substituents selected from halogen, hydroxy, $NH_2$, CN, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, $C_1$-$C_6$ dialkylamino or phenyl.

According to the description and claims, the term "$C_3$-$C_8$ cycloalkyl" refers to a saturated monocyclic hydrocarbon ring system having three to eight carbon atoms and zero heteroatoms. Representative examples of cycloalkyl groups include, but are not limited to, cyclopropyl, cyclopentyl, and cyclohexyl.

According to the description and claims, the term "$C_1$-$C_6$ alkyl" refers to a straight or branched hydrocarbon chain radical, consisting solely of carbon and hydrogen atoms, having from one to six carbon atoms. The "$C_1$-$C_6$ alkyl" group is preferably a linear or branched $C_1$-$C_4$ alkyl group, more preferably a $C_1$-$C_2$ alkyl group.

According to the description and claims, the term "$C_1$-$C_6$ alkoxy" refers to a straight or branched O—$C_1$-$C_6$ alkyl, where alkyl is as defined herein. The "$C_1$-$C_6$ alkoxy" group is preferably a linear or branched $C_1$-$C_4$ alkoxy group, more preferably a $C_1$-$C_2$ alkoxy group.

According to the description and claims, the term "$C_1$-$C_6$ haloalkyl" refers to a straight or branched hydrocarbon chain radical, which is substituted by one or more halogen atoms and having from one to six carbon atoms. The "$C_1$-$C_6$ haloalkyl" group is preferably a linear or branched $C_1$-$C_4$ haloalkyl group, more preferably a $C_1$-$C_2$ haloalkyl group, being in particular $CF_3$.

According to the description and claims, the term "$C_1$-$C_6$ haloalkoxy" refers to a straight or branched O—$C_1$-$C_6$ haloalkyl, where haloalkyl is as defined herein. The "$C_1$-$C_6$ haloalkoxy" group is preferably a linear or branched $C_1$-$C_4$ haloalkoxy group, more preferably a $C_1$-$C_2$ haloalkoxy group, being in particular $OCF_3$, $OCHF_2$ or $OCH_2F$.

According to the description and claims, the term "$C_1$-$C_6$ acylamino" refers to a straight or branched —NH—C(O)—$C_1$-$C_6$ alkyl, where $C_1$-$C_6$ alkyl is as defined herein.

According to the description and claims, the term "$C_1$-$C_6$ alkylamino" refers to a straight or branched —NH—$C_1$-$C_6$ alkyl, where $C_1$-$C_6$ alkyl is as defined herein.

"Halogens" are preferably fluorine, chlorine or bromine, being in particular fluorine or chlorine.

In the case p represents the integers 2 or 3 it is to be understood that each $R^1$ substituent may be the same or different.

"Pharmaceutically acceptable salts" comprise conventional non-toxic salts obtained by salification with inorganic acids (e.g. hydrochloric, hydrobromide, sulphuric or phosphoric acids), or with organic acids (e.g. acetic, propionic, succinic, benzoic, cinnamic, mandelic, salicylic, glycolic, lactic, oxalic, malic, maleic, malonic, fumaric, tartaric, citric, p-toluenesulfonic or methanesulfonic acids).

In addition, the compounds of the present invention can exist in unsolvated as well as in solvated forms with pharmaceutically acceptable solvents such as water, ethanol and the like.

The compounds of the invention and their pharmaceutical acceptable salts can exist as single stereoisomers, racemates, and as mixtures of diastereoisomers. The compounds can exist also as geometric isomers. All such geometric isomers, single stereoisomers, racemates and mixtures thereof, are intended to be within the scope of the invention.

The present invention comprises metabolic precursors of compounds of formula (I). The term "metabolic precursors" means compounds having a different structure from that of the relevant formula (I), which after administration to the patient are directly or indirectly transformed into a compound of said formula (I). Methods for selecting metabolic precursors and their relative preparation are described for example in the book by Bundgaard (Bundgaard, H. ed., "Design of Prodrugs", Elsevier, 1985).

A preferred sub-group of compounds is that defined by the structure of formula (I) as drawn above in the summary, wherein:

m, n are independently zero or an integer from 1 to 4;

p is zero or 1;

R is hydrogen; $C_1$-$C_4$ alkyl, optionally substituted by $C_3$-$C_8$ cycloalkyl, phenyl, or hetero($C_2$-$C_9$)aryl; (CO)$R^2$; $C_3$-$C_8$ cycloalkyl; phenyl; or hetero($C_2$-$C_9$)aryl;

$R^1$ is halogen, $C_1$-$C_4$ alkyl, $C_1$-$C_4$ haloalkyl, $C_1$-$C_4$ alkoxy, or $C_1$-$C_4$ haloalkoxy;

Y is $CH_2$ or $NR^4$;

Z is C=$R^5$;

$R^2$ is $C_1$-$C_4$ alkyl, optionally substituted by phenyl or by hetero($C_2$-$C_9$)aryl; phenyl; hetero($C_2$-$C_9$)aryl; O—$C_1$-$C_4$ alkyl; or $NR^6R^7$;

$R^4$ is hydrogen; $C_1$-$C_4$ alkyl, optionally substituted by phenyl;

$R^5$ is oxygen or $NOR^8$;

$R^6$ is hydrogen; $C_1$-$C_4$ alkyl, optionally substituted by phenyl; or phenyl;

$R^7$ is hydrogen; $C_1$-$C_4$ alkyl, optionally substituted by phenyl;

$R^8$ is hydrogen; $C_1$-$C_4$ alkyl, optionally substituted by phenyl;

and the pharmaceutically acceptable salts thereof.

Examples of specific compounds belonging to formula (I) are the following:

(±)-(E)-3-[4-oxo-spiro(chromane-2,3'-pyrrolidine)-6-yl]-N-hydroxy-acrylamide;
(±)-(E)-3-[1'-Benzyl-4-oxo-spiro(chromane-2,3'-pyrrolidine)-6-yl]-N-hydroxy-acrylamide;
(−)-(E)-3-[1'-Benzyl-4-oxo-spiro(chromane-2,3'-pyrrolidine)-6-yl]-N-hydroxy-acrylamide;
(+)-(E)-3-[1'-Benzyl-4-oxo-spiro(chromane-2,3'-pyrrolidine)-6-yl]-N-hydroxy-acrylamide;
(±)-(E)-3-[1'-Acetyl-4-oxo-spiro(chromane-2,3'-pyrrolidine)-6-yl]-N-hydroxy-acrylamide;
(±)-(E)-3-[1'-Benzoyl-4-oxo-spiro(chromane-2,3'-pyrrolidine)-6-yl]-N-hydroxy-acrylamide;
(±)-(E)-3-[1'-Methyl-4-oxo-spiro(chromane-2,3'-pyrrolidine)-6-yl]-N-hydroxy-acrylamide;
(±)-(E)-3-[1'-Ethyloxycarbonyl-4-oxo-spiro(chromane-2,3'-pyrrolidine)-6-yl]-N-hydroxy-acrylamide;
(±)-(E)-3-[1'-(2-Phenyl-ethyl)-4-oxo-spiro(chromane-2,3'-pyrrolidine)-6-yl]-N-hydroxy-acrylamide;
(±)-(E)-3-[1'-(1-Methyl-1H-indol-3-ylmethyl)-4-oxo-spiro(chromane-2,3'-pyrrolidine)-6-yl]-N-hydroxy-acrylamide;
(±)-(E)-3-[1'-(4-Fluoro-benzyl)-4-oxo-spiro(chromane-2,3'-pyrrolidine)-6-yl]-N-hydroxy-acrylamide;
(±)-(E)-3-[4-oxo-spiro(chromane-2,3'-piperidine)-6-yl]-N-hydroxy-acrylamide;
(±)-(E)-3-[1'-Benzyl-4-oxo-spiro(chromane-2,3'-piperidine)-6-yl]-N-hydroxy-acrylamide;
(±)-(E)-3-[1'-Methyl-4-oxo-spiro(chromane-2,3'-piperidine)-6-yl]-N-hydroxy-acrylamide;
(±)-(E)-3-[1'-Ethyloxycarbonyl-4-oxo-spiro(chromane-2,3'-piperidine)-6-yl]-N-hydroxy-acrylamide;
(±)-(E)-3-[1'-Acetyl-4-oxo-spiro(chromane-2,3'-piperidine)-6-yl]-N-hydroxy-acrylamide;
(−)-(E)-3-[1'-Benzyl-4-oxo-spiro(chromane-2,3'-piperidine)-6-yl]-N-hydroxy-acrylamide;
(+)-(E)-3-[1'-Benzyl-4-oxo-spiro(chromane-2,3'-piperidine)-6-yl]-N-hydroxy-acrylamide;
(±)-(E)-3-[1'-(4-Fluoro-benzyl)-4-oxo-spiro(chromane-2,3'-piperidine)-6-yl]-N-hydroxy-acrylamide;
(±)-(E)-3-[1'-(2-Phenyl-ethyl)-4-oxo-spiro(chromane-2,3'-piperidine)-6-yl]-N-hydroxy-acrylamide;
(±)-(E)-3-[1'-Benzoyl-4-oxo-spiro(chromane-2,3'-piperidine)-6-yl]-N-hydroxy-acrylamide;
(±)-(E)-3-[4-oxo-spiro(chromane-2,4'-azepane)-6-yl]-N-hydroxy-acrylamide;
(±)-(E)-3-[1'-Benzyl-4-oxo-spiro(chromane-2,4'-azepane)-6-yl]-N-hydroxy-acrylamide;
(±)-(E)-3-[1'-Acetyl-4-oxo-spiro(chromane-2,4'-azepane)-6-yl]-N-hydroxy-acrylamide;
(±)-(E)-3-[1'-Benzoyl-4-oxo-spiro(chromane-2,4'-azepane)-6-yl]-N-hydroxy-acrylamide;
(±)-(E)-3-[1'-Methyl-4-oxo-spiro(chromane-2,4'-azepane)-6-yl]-N-hydroxy-acrylamide;
(±)-(E)-3-[1'-Ethyloxycarbonyl-4-oxo-spiro(chromane-2,4'-azepane)-6-yl]-N-hydroxy-acrylamide;
(±)-(E)-3-[1'-(2-Phenyl-ethyl)-4-oxo-spiro(chromane-2,4'-azepane)-6-yl]-N-hydroxy-acrylamide;
(±)-(E)-3-[1'-(4-Fluoro-benzyl)-4-oxo-spiro(chromane-2,4'-azepane)-6-yl]-N-hydroxy-acrylamide;
(E)-3-[4-oxo-spiro(chromane-2,3'-azetidine)-6-yl]-N-hydroxy-acrylamide;
(E)-3-[1'-Benzyl-4-oxo-spiro(chromane-2,3'-azetidine)-6-yl]-N-hydroxy-acrylamide;
(E)-3-[1'-(2-Phenyl-ethyl)-4-oxo-spiro(chromane-2,3'-azetidine)-6-yl]-N-hydroxy-acrylamide;
(E)-3-[1'(4-Fluoro-benzyl)-4-oxo-spiro(chromane-2,3'-azetidine)-6-yl]-N-hydroxy-acrylamide;
(E)-3-[1'-Methyl-4-oxo-spiro(chromane-2,3'-azetidine)-6-yl]-N-hydroxy-acrylamide;
(E)-3-{1-[2-(4-Fluoro-phenyl)-ethyl]-4-oxo-spiro(chromane-2,3'-azetidine)-6-yl}-N-hydroxy-acrylamide;
(E)-3-[1'-Acetyl-4-oxo-spiro(chromane-2,3'-azetidine)-6-yl]-N-hydroxy-acrylamide;
(E)-3-[1'-Benzoyl-4-oxo-spiro(chromane-2,3'-azetidine)-6-yl]-N-hydroxy-acrylamide;
(E)-3-[1'-Ethyloxycarbonyl-4-oxo-spiro(chromane-2,3'-azetidine)-6-yl]-N-hydroxy-acrylamide;
(±)-(E)-3-{3,4-Dihydro-4-oxo-spiro[2H-(1,3)-benzoxazine-2,3'-piperidin]-6-yl}-N-hydroxy-acrylamide;
(±)-(E)-3-{1'-Benzyl-3,4-dihydro-4-oxo-spiro[2H-(1,3)-benzoxazine-2,3'-piperidin]-6-yl}-N-hydroxy-acrylamide;
(±)-(E)-3-{1'-Methyl-3,4-dihydro-4-oxo-spiro[2H-(1,3)-benzoxazine-2,3'-piperidin]-6-yl}-N-hydroxy-acrylamide;
(±)-(E)-3-{1'-(4-Fluoro-benzyl)-3,4-dihydro-4-oxo-spiro[2H-(1,3)-benzoxazine-2,3'-piperidin]-6-yl}-N-hydroxy-acrylamide;
(±)-(E)-3-{1'-(2-Phenyl-ethyl)-3,4-dihydro-4-oxo-spiro[2H-(1,3)-benzoxazine-2,3'-piperidin]-6-yl}-N-hydroxy-acrylamide;
(E)-3-[1'-(1-Methyl-1H-indol-3-ylmethyl)-4-oxo-spiro(chromane-2,3'-azetidine)-6-yl]-N-hydroxy-acrylamide;
(±)-(E)-3-[1'-(1-Methyl-1H-indol-3-ylmethyl)-4-oxo-spiro(chromane-2,3'-piperidine)-6-yl]-N-hydroxy-acrylamide;
(±)-(E)-3-{1'-(1-Methyl-1H-indol-3-ylmethyl)-4-oxo-spiro[2H-(1,3)-benzoxazine-2,3'-piperidin]-6-yl}-N-hydroxy-acrylamide;
(±)-(E)-3-[1'-(1-Methyl-1H-indol-3-ylmethyl)-4-oxo-spiro(chromane-2,4'-azepane)-6-yl]-N-hydroxy-acrylamide;
(±)-(E)-3-(1'-Ethyl-4-oxospiro[chromane-2,3'-piperidine]-6-yl)-N-hydroxy-acrylamide;
(±)-(E)-3-(1'-Isopropyl-4-oxospiro[chromane-2,3'-piperidine]-6-yl)-N-hydroxy-acrylamide;
(±)-(E)-3-(1'-Cyclopentyl-4-oxospiro[chromane-2,3'-piperidine]-6-yl)-N-hydroxy-acrylamide;
(E)-3-(1'-Benzyl-8-fluoro-4-oxospiro[chromane-2,4'-piperidine]-6-yl)-N-hydroxy-acrylamide;
(E)-3-(1'-Benzyl-8-methyl-4-oxospiro[chromane-2,4'-piperidine]-6-yl)-N-hydroxy-acrylamide;
(E)-3-(1'-(4-Fluorobenzyl)-4-(methoxyimino)spiro[chroman-2,3'-piperidine]-6-yl)-N-hydroxyacrylamide;
(E)-3-(1'-Cyclopentyl-4-(hydroxyimino)spiro[chroman-2,3'-piperidine]-6-yl)-N-hydroxyacrylamide;
(E)-3-(4-(Benzyloxyimino)-1'-phenethylspiro[chroman-2,3'-piperidine]-6-yl)-N-hydroxyacrylamide.

The compounds according to the present invention can be prepared, for example, as shown in the reaction schemes below and according to the reaction steps specified as follows, or, particularly, in a manner as described by way of example in the following examples, or analogously or similarly thereto using preparation procedures and synthesis strategies known to the person skilled in the art.

Compounds of general formula (I), wherein Z is C=NOR$^8$, with R$^8$ as defined above, can be prepared by treating compounds of formula (I), wherein Z is C=O with H$_2$NOR$^8$, in the presence of a suitable base (e.g. pyridine) in a suitable solvent (e.g. ethanol or DMF). The reaction can be carried out at a temperature between room temperature and the boiling point of the solvent.

Compounds of general formula (I), wherein Z is C=O, can be prepared according to Scheme A:

Scheme A

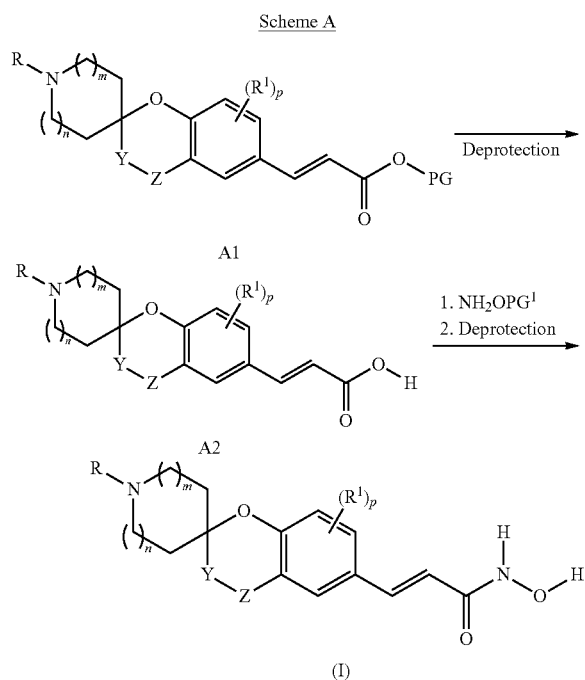

wherein m, n, p, R, $R^1$, and Y are as defined above in formula (I), Z is C=O, PG and $PG^1$ are protecting groups chosen among those known in the art, for example methyl, tert-butyl, etc. for PG and O-(tetrahydro-2H-pyran-2-yl), etc. for $PG^1$.

A compound of formula A1 can be deprotected into a compound of formula A2 according to known methods, e.g. by treatment of a tert-butyl ester derivative with TFA (trifluoroacetic acid) in a suitable solvent such as dichloromethane at a temperature ranging from 0° C. to room temperature or by treatment of a methyl ester with LiOH or NaOH in a suitable solvent, for example in methanol, in a methanol/water or in a dioxane/water mixture, or by treatment with HCl in a water/acetic acid or water/dioxan mixture. The hydrolysis of the methyl ester can be carried out at a temperature ranging from 0° C. to the boiling point of the solvent.

The reaction of a compound of formula A2 with the protected hydroxylamine $NH_2OPG^1$ can be carried out with condensating agents such as EDC (1-(3-dimethylaminopropyl)-3-ethylcarbodiimide), optionally in the presence of a suitable base (e.g. triethylamine or di-isopropylethylamine) in a suitable solvent (e.g. tetrahydrofuran, dichloromethane or DMF). Generally an activator of the condensation reaction, such as HOBt (1-hydroxybenzotriazole) or HOAt (1-hydroxy-7-azabenzotriazole), can be added to the reaction mixture. The reaction can be carried out at room temperature for a period lasting between about 2 and 12 h. Deprotection of the hydroxylamine can be achieved by known methods, for example in the case of tetrahydropyran-2-yl using HCl in aprotic solvents (such as THF, diethylether or dioxane).

The compounds of formula A1 can be prepared by synthetic methods and chemical reactions per se well-known in the art. For example, a compound of formula A1, wherein Z is C=O, can be prepared according to Scheme B:

Scheme B

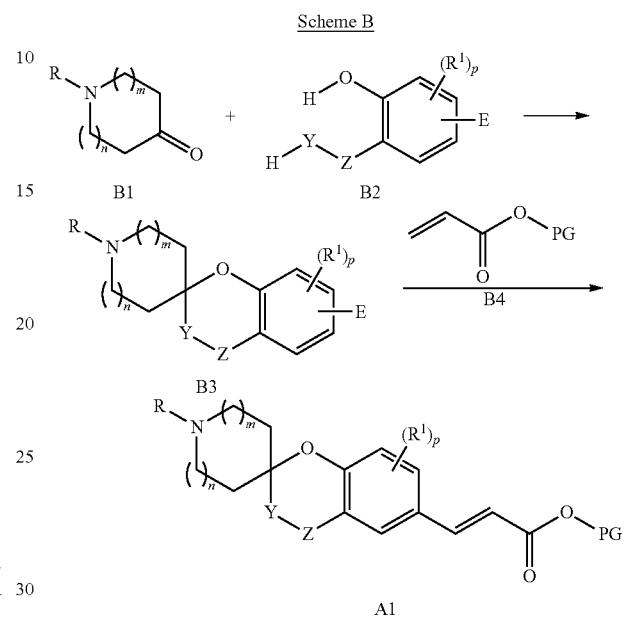

wherein m, n, p, R, $R^1$, Y, and PG are as defined above and, Z is C=O, H is hydrogen, and E is bromine or iodine.

Compounds of formula B1 and B2 are known compounds or can be prepared by known methods. Reaction between a compound of formula B1 and B2 can be carried out in presence of a base (e.g. pyrrolidine) in an appropriate solvent (e.g. methanol) at a temperature ranging from 0° C. to the boiling point of the solvent.

Reaction of a compound of formula B3 with the protected acroylester B4 can be carried out according to the Heck reaction. The reaction conditions are described for example in the book by Larhed and Hallberg (Larhed, M.; Hallberg, A. "Handbook of Organopalladium Chemistry for Organic Synthesis", Negishi, E., Ed.; Wiley-Interscience, 2002). The reaction can be carried out in a suitable organic solvent (e.g. DMF) in the presence of palladium salts (e.g. palladium acetate), organic or inorganic bases (e.g. triethylamine, 1,4-diazabicyclo[2,2,2]-octane, sodium or potassium carbonate) and phosphine ligand derivatives, such as triphenylphosphine or tri-o-tolyl-phosphine, at a temperature between room temperature and the boiling point of the solvent.

Alternatively, compounds of formula A1, wherein Z is C=O, can be prepared according to Scheme C:

Scheme C

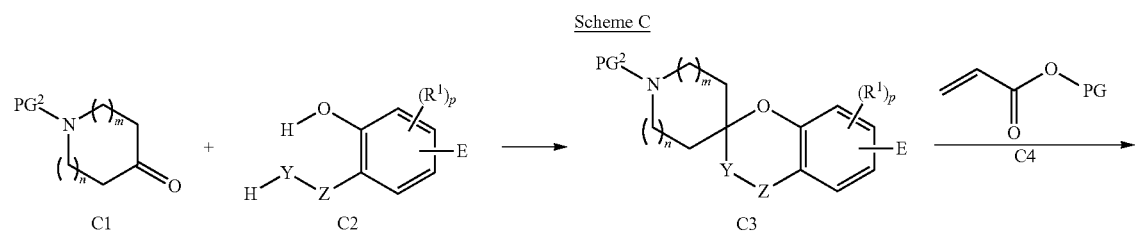

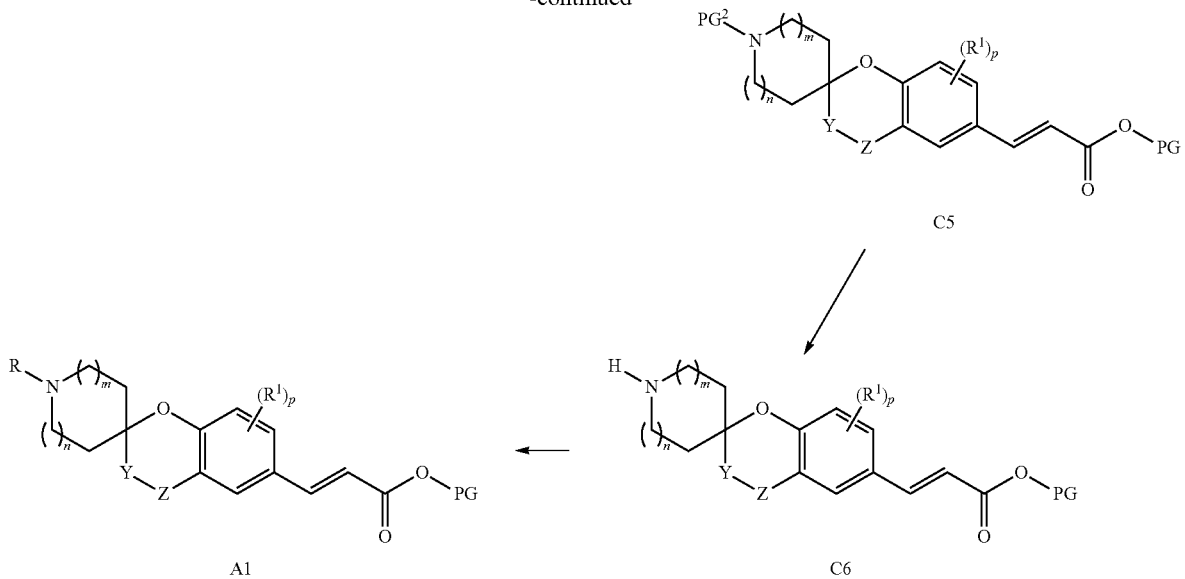

wherein m, n, p, R, R$^1$, Y, H, E, and PG are as defined above, Z is C=O, and PG$^2$ is a protecting group chosen among those known in the art, e.g. carboxybenzyl, tert-butyloxycarbonyl (BOC), 9-fluorenylmethyloxycarbonyl, etc.

Compounds of formula C1 and C2 are known compounds or can be prepared by known methods. Reaction between a compound of formula C1 and a compound of formula C2 can be carried out at the same conditions like the reaction between a compound of formula B1 and a compound of formula B2 as outlined in Scheme B. The Heck reaction between a compound of formula C3 with a protected acroylester C4 can be carried out at the same conditions like the reaction between a compound of formula B3 with the protected acroylester B4 as outlined in Scheme B. A compound of formula C5 can be deprotected into a compound of formula C6 according to known methods, e.g. by treatment of a BOC derivative with TFA (trifluoroacetic acid) in a suitable solvent such as dichloromethane or dioxane, at a temperature ranging from 0° C. to room temperature. The compound of formula A1 can be prepared starting from compound of formula C6 and a compound of formula R—W, R$^2$—(CO)W or R$^3$—(SO$_2$)W, wherein R is C$_1$-C$_6$ alkyl, optionally substituted by C$_3$-C$_8$ cycloalkyl, C$_6$-C$_{10}$ aryl or hetero(C$_2$-C$_9$)aryl, W is a halogen atom, e.g. chloride or bromide, R$^2$ and R$^3$ are C$_1$-C$_6$ alkyl, optionally substituted by C$_6$-C$_{10}$ aryl or by hetero(C$_2$-C$_9$) aryl; C$_6$-C$_{10}$ aryl; or hetero(C$_2$-C$_9$)aryl. The reaction between the compound of formula C6 and a compound of formula R—W, a compound of formula R$^2$—(CO)W or a compound of formula R$^3$—(SO$_2$)W can be carried out in a suitable organic solvent, e.g. dichloromethane, in presence of a base (e.g. triethylamine) at a temperature ranging from about 0° C. to about 50° C. Alternatively, a compound of formula A1, wherein R is C$_1$-C$_6$ alkyl, optionally substituted by C$_3$-C$_8$ cycloalkyl, C$_8$-C$_{10}$ aryl or hetero(C$_2$-C$_9$)aryl, can be prepared starting from compound of formula C6 and a compound of formula R$^{14}$—CHO, wherein R$^{14}$ is hydrogen or C$_1$-C$_5$ alkyl, optionally substituted by C$_3$-C$_8$ cycloalkyl, C$_6$-C$_{10}$ aryl or hetero(C$_2$-C$_9$)aryl; C$_3$-C$_8$ cycloalkyl, C$_6$-C$_{10}$ aryl or hetero(C$_2$-C$_9$)aryl, preferably under nitrogen atmosphere, in a suitable organic solvent (e.g. dichloromethane, methanol, ethanol or tetrahydrofuran) at a temperature between about 0 and the boiling point of the solvent in the presence of a reducing agent such as sodium borohydride, sodium triacetoxyborohydride or sodium cyanoborohydride.

In the case it is necessary to protect a chemical group of a compound of the present invention and/or an intermediate thereof, before carrying out one of the aforedescribed reactions, said chemical group can be protected and deprotected according to known methods. A thorough discussion for protection/deprotection steps is provided for example in Greene and Wuts (Greene, T. W.; Wuts, P. G. M. "Protective Groups in Organic Synthesis", John Wiley & Sons Inc., 1991) or in Kocienski (Kocienski, P. J. "Protecting Groups", George Thieme Verlag, 1994).

Salification of the compounds of formula (I), and preparation of compounds of formula (I), free of their salts, can be carried out by known conventional methods.

The invention also comprises a method for preventing and/or treating diseases linked to the disregulation of histone deacetylase activity characterized by administering to a patient a pharmacologically useful quantity of one or more compounds of formula (I), as previously defined. The invention includes the same compounds for use in the prevention or treatment of the aforesaid diseases. Further provided by the invention is the use of the same compounds for the manufacture of a medicament for the prevention or treatment of the aforesaid diseases.

In view of the above described mechanisms of action, the compounds of the present invention are useful in the prevention or treatment of tumor type diseases, including but not limited to: acute and chronic myeloid leukaemia, acute and chronic lymphoblastic leukaemia, myelodysplastic syndromes, multiple myeloma, Hodgkin's disease, non-Hodgkin's lymphomas, cutaneous and peripheral T-cell lymphoma, adult T-cell leukemia, large B-cell lymphoma; mammary tumors; pulmonary tumors and pleural mesotheliomas, adenocarcinoma, non-small lung cancer, small-cell lung cancer; skin tumors including basal cell carcinomas (basaliomas), melanomas, squamous cell carcinoma, Kaposi's sarcoma, keratocanthomas; osteosarcomas, fibrosarcomas, rhabdomyosarcomas, neuroblastomas, glioblastomas, cerebral tumors, head and neck cancer, testicular and ovarian tumors, cervical carcinoma, endometrial and prostate tumors (for example advanced prostate cancer), thyroid carcinomas (for example tyroid follicular cancer), colon cancers (for example colon adenocarcinoma, colon adenoma), gastric tumors and gastrointestinal adenocarcinomas, hepatic carcinomas, pancreatic carcinomas (for example exocrine pancreatic carcinoma), renal tumors, teratocarcinomas and embryonic carcinomas.

The compounds of the invention are also useful in the prevention or treatment of neurological conditions, including, but not limited to, epilepsy, neuropathic pain, cerebral ischemia, spinal and bulbar muscular atrophy, Friedreich's ataxia, Huntington's disease, Alzheimer's disease, Parkinson's disease, amyotrophic lateral sclerosis, Rett syndrome, diffuse Lewy body syndrome, Gilles de la Tourette syndrome, diseases caused by protein aggregates, Kennedy's disease, and multiple sclerosis.

The compounds of the invention are also useful in the prevention or treatment of mental retardation, including, but not limited to, fragile X syndrome and Rubinstein-Taybi syndrome.

The compounds of the invention are also useful in the prevention or treatment of psychiatric disorders, including, but not limited to, bipolar disorders, depression and schizophrenia.

The compounds of the invention are also useful in the prevention or treatment of inflammatory diseases, including, but not limited to, inflammatory responses of the nervous system, inflammatory bowel disease (e.g. Crohn's disease, ulcerative colitis), sarcoidosis, and arthritis.

The compounds of the invention are also useful in the prevention or treatment of immune disorders, including, but not limited to, autoimmune diseases, chronic immune reactions against the host, psoriasis, atopic dermatitis and systemic lupus erythematosus.

The compounds of the invention are also useful in the prevention or treatment of infections, including, but not limited to, infections caused by protozoa, fungi, phytotoxic agents, viruses and parasites, for example HIV infections, malaria, leishmaniasis, bilharziasis, amoebiasis, African trypanosomiasis, toxoplasmosis, cryptosporidiosis, Chagas disease, infections caused by *Eimeria tenella, Sarcocystis neurona, Neospora caninum*.

The compounds of the invention are also useful in the prevention or treatment of cardiovascular disorders, including, but not limited to, hypertrophy and cardiac decompensation, restenosis, reperfusion injury, cardiac failure, and cardiac ischemia.

The compounds of the invention are also useful in the prevention or treatment of other diseases such as diabetes, fibrotic diseases of the skin, fibrosis, renal diseases, beta thalassemia and respiratory diseases, including, but not limited to, chronic obstructive pulmonary disorders and asthma.

The compounds of formula (I) can also be used in combination with additional agents, in particular anti-tumor and differentiating agents, either by separate administrations, or by including the two active principles in the same pharmaceutical formulation. Non-exhaustive examples of suitable additional agents include:

a) other histone deacetylase inhibitors (for example SAHA, PXD101, JNJ-16241199, JNJ-26481585, SB939, ITF-2357, LBH589, PCI-24781, resminostat, CHR-3996, AR-42, valproic acid, butyric acid, MS-275, MGCD0103, chidamide or FK-228);

b) retinoid receptor modulators such as 13-cis-retinoic acid, 9-cis-retinoic acid, bexarotene, alitretinoin, or tretinoin; vitamin D;

c) antiproliferative/antineoplastic drugs and combinations thereof, as used in medical oncology, such as alkylating agents (for example platin derivatives like cis-platin, carboplatin, oxaliplatin, lobaplatin, satraplatin, nedaplatin, heptaplatin; nitrogen mustard such as chlorambucil, melphalan, chlormethine, cyclophosphamide, ifosfamide, trofosfamide, uramustine, bendamustine, estramustine; busulphan, temozolomide or nitrosoureas); antimetabolites (for example antifolates such as aminopterin, methotrexate, pemetrexed, raltitrexed); purines such as cladribine, clofarabine, fludarabine, mercaptopurine, pentostatin, thioguanine; pyrimidines like capecitabine, cytarabine, fluorouracil, floxuridine, gemcitabine; azacitidine, decitabine; cytosine arabinoside or hydroxyurea; antitumour antibiotics (for example anthracyclines like aclarubicin, amrubicin, daunomycin, doxorubicin, epirubicin, idarabicin, valrubicin, zorubicine; mitoxantrone; or antibiotics from streptomyces like actinomycin, bleomycin, mitomycin, or plicamycin); antimitotic agents (for example vinca alkaloids like vincristine, vinblastine, vindesine or vinorelbine; taxoids like docetaxel, paclitaxel or tesetaxel; epothilones like ixabepilone) and topoisomerase inhibitors (for example epipodophyllotoxins like etoposide and teniposide; amsacrine, camptothecin, irinotecan, rubitecan, and topotecan);

d) cytostatic agents such as antioestrogens (for example tamoxifen, toremifene, raloxifene, droloxifene and idoxifene), oestrogen receptor down regulators (for example fulvestrant), antiandrogens (for example bicalutamide, flutamide, nilutamide, liarozole or cyproterone acetate), LHRH antagonists or LHRH agonists (for example goserelin, leuprorelin or buserelin), progestogens (for example megestrol acetate), aromatase inhibitors (for example as anastrozole, letrozole, vorazole and exemestane) and inhibitors of 5-alpha-reductase such as finasteride;

e) agents which inhibit cancer cell invasion (for example metalloproteinase inhibitors and inhibitors of urokinase plasminogen activator receptor function);

f) inhibitors of growth factor function, for example growth factor antibodies, growth factor receptor antibodies (for example the anti-erbb2 antibody trastuzumab, the anti-erbb1 antibody cetuximab and panitumumab, the anti IGF1R antibody figitumumab), farnesyl transferase inhibitors, MEK inhibitors, tyrosine kinase inhibitors and serine/threonine kinase inhibitors, for example enzastaurin, dasatinib, erlotinib, gefitinib, imatinib, lapatinib, nilotinib, sorafenib, sunitinib, everolimus, sirolimus or temsirolimus;

g) antiangiogenic agents such as those which inhibit the effects of vascular endothelial growth factor, for example the anti-vascular endothelial cell growth factor antibody bevacizumab [Avastin™], lenalidomide or thalidomide;

h) cell cycle inhibitors including for example CDK inhibitors (for example flavopiridol, roscovitine) and other inhibitors of cell cycle checkpoints; inhibitors of aurora kinase and other kinases involved in mitosis and cytokinesis regulation;

i) proteasome inhibitors (for example lactacystin, bortezomib, epoxomicin);

j) HSP90 inhibitors (for example 17-AAG, AT-13387, KOS-953, KOS-1022, CNF-1010, CNF-2024, IPI-504, IPI-926, SNX 5422, STA-9090, VER-52296, PU-H17 or XL-888);

k) Selective COX-2 inhibitors (for example celecoxib), or non selective NSAIDs (for example diclofenac, flurbiprofen, ibuprofen, ketoprofen, or naproxen).

In another aspect, a compound of general formula (I) can be used in combination with radiation therapy. In yet another aspect, a compound of general formula (I) may be administered in combination with standard chemotherapy combinations such as, but not restricted to, CMF (cyclophosphamide, methotrexate and 5-fluorouracil), CAF (cyclophosphamide, doxorubicin and 5-fluorouracil), AC (doxorubicin and cyclophosphamide), FEC (5-fluorouracil, epirubicin, and cyclophosphamide), ACT or ATC (doxorubicin, cyclophosphamide, and paclitaxel), or CMFP (cyclophosphamide, methotrexate, 5-fluorouracil and prednisone).

The invention also comprises pharmaceutical compositions characterized by containing one or more active principles of formula (I), in association with pharmaceutically acceptable carrier, excipients and diluents.

The compounds of this invention can be administered via any of the accepted modes of administration or agents for serving similar utilities. Thus, administration can be, for example, oral, nasal, parental (intravenous, subcutaneous, intramuscular), buccal, sublingual, rectal, topical, transdermal, intravesical, or using any other route of administration.

The compounds of formula (I) can be pharmaceutically formulated according to known methods. The pharmaceutical compositions can be chosen on the basis of the treatment requirements. Such compositions are prepared by blending and are suitably adapted to oral or parenteral administration, and as such can be administered in the form of tablets, capsules, oral preparations, powders, granules, pills, injectable or infusible liquid solutions, suspensions or suppositories.

Tablets and capsules for oral administration are normally presented in unit dose form and contain conventional excipients such as binders, fillers, diluents, tableting agents, lubricants, detergents, disintegrants, coloring agents, flavoring agents and wetting agents. The tablets can be coated using methods well known in the art.

Suitable fillers include cellulose, mannitol, lactose and other similar agents. Suitable disintegrants include polyvinylpyrrolidone and starch derivatives such as sodium glycolate starch. Suitable lubricants include, for example, magnesium stearate. Suitable wetting agents include sodium lauryl sulfate.

The oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents.

Oral formulations also include conventional slow-release formulations such as enterically coated tablets or granules.

Pharmaceutical preparation for administration by inhalation can be delivered from an insufflator, nebulizer pressurized packs or other convenient means of delivering an aerosol spray.

For parenteral administration (e.g. bolus injection or continuous infusion), fluid unit dosages (e.g. in ampoules or in multi-dose containers) can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the invention.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. A reference for the formulations is the book by Remington ("Remington: The Science and Practice of Pharmacy", Lippincott Williams & Wilkins, 2000). Creams, as known to formulation experts, are viscous liquids or semisolid emulsions, and contain an oil phase, an emulsifier and an aqueous phase. The oil phase generally contains petrolatum and an alcohol such as cetyl or stearic alcohol. The emulsifier in a cream formulation is chosen from non-ionic, anionic, cationic or amphoteric surface-active agents. The monophasic gels contain the organic molecules uniformly distributed in the liquid, which is generally aqueous, but they also preferably contain an alcohol and optionally an oil. Preferred gelling agents are cross-linked acrylic acid polymers (e.g. carbomer-type polymers, such as carboxypolyalkylenes, which are commercially available under the Carbopol™ trademark). Hydrophilic polymers are also preferred, such as polyoxyethylene, polyoxyethylene-polyoxypropylene copolymers and polyvinyl alcohol; cellulose polymers such as hydroxypropyl cellulose, hydroxyethyl cellulose, hydroxypropyl methylcellulose, hydroxypropyl methylcellulose phthalate and methylcellulose; gums, such as xanthan gum and tragacanth gum; sodium alginate; and gelatin. Dispersing agents such as alcohol or glycerin can be added for gel preparation. The gelling agent can be dispersed by finely chopping and/or mixing.

Formulations suitable for topical administration to the eye also include eye drops, wherein the active ingredient is dissolved or suspended in a suitable carrier, especially an aqueous solvent for the active ingredient.

A further method of administering the compounds of the invention regards transdermal delivery. Typical transdermal formulations comprise conventional aqueous and non-aqueous vectors, such as creams, oils, lotions or pastes or can be in the form of membranes or medicated patches. One formulation provides that a compound of the invention is dispersed within a pressure sensitive patch which adheres to the skin. This formulation enables the compound to diffuse from the patch to the patient through the skin. For a constant release of the drug through the skin, natural rubber and silicon can be used as pressure sensitive adhesives.

The above mentioned uses and methods also include the possibility of co-administration of additional therapeutic agents, simultaneously or delayed with respect to the administration of the compound of formula (I).

In the previously mentioned uses and methods, the dosage of the compounds of formula (I), can vary depending upon a variety of factors including the patient type and condition, the degree of disease severity, mode and time of administration, diet and drug combinations. As an indication, they can be administered within a dose range of between 0.001 and 1000 mg/kg/day. The determination of optimum dosages for a particular patient is well known to one skilled in the art.

As is common practice, the compositions are normally accompanied by written or printed instructions for use in the treatment in question.

The following examples and biological data are presented in order to further illustrate the invention.

EXPERIMENTAL PART

Chemical Synthesis

Methods

Unless otherwise indicated, all the starting reagents were found to be commercially available and were used without any prior purification. Specifically, the following abbreviations may have been used in the descriptions of the experimental methods:

| | |
|---|---|
| NMR (Nuclear Magnetic Resonance) | $^1$H (proton) |
| MHz (Megahertz) | Hz (Hertz) |
| HPLC (High Performance Liquid Chromatography) | LC-MS (Liquid Chromatography Mass Spectrum) |
| s (seconds) | min (minutes) |
| h (hours) | mg (milligrams) |
| g (grams) | µl (microliters) |
| ml (milliliters) | mmol (millimoles) |
| M (molarity) | rt (retention time in minutes) |
| RT (room temperature) | MW (microwave) |
| AcOH (acetic acid) | BOC (tert-butoxycarbonyl) |
| BOC anhydride (di-tert-butyldicarbonate) | Bu$_4$NBr (tetrabutylammonium bromide) |
| CH$_3$CN (acetonitrile) | DCM (dichloromethane) |
| DIPEA (N,N-diisopropyl-ethylamine) | DMF (dimethylformamide) |
| DMSO (dimethyl sulfoxide) | DMSO-d$_6$ (deuterated dimethyl sulfoxide) |
| EDC (1-3(dimethylaminopropyl)-3-ethylcarbodiimide hydrochloride) | Et$_2$O (diethyl ether) |
| EtOAc (ethyl acetate) | EtOH (ethanol) |
| HCl (hydrochloric acid) | HOBt (1-hydroxybenzotriazole) |
| i-PrOH (isopropyl alcohol) | K$_2$CO$_3$ (potassium carbonate) |
| MeOH (methanol) | NaBH(OAc)$_3$ (Sodium triacetoxyborohydride) |
| Na$_2$CO$_3$ (sodium carbonate) | NaHCO$_3$ (sodium hydrogen carbonate) |
| NaOH (sodium hydroxide) | Na$_2$SO$_4$ (sodium sulphate) |
| NH$_2$OTHP (O-(tetrahydro-2H-pyran-2-yl)hydroxylamine) | NH$_3$ (ammonia) |
| Pd(OAc)$_2$ (palladium acetate) | P(o-tol)$_3$ (tri-o-tolyl-phosphane) |
| TEA (triethylamine) | TFA (trifluoroacetic acid) |

Except where indicated otherwise, all temperatures are expressed in ° C. (degrees centigrade) or K (Kelvin).

The $^1$H-NMR spectra were acquired with a Bruker 300 MHz instrument. The chemical shifts are expressed in parts per million (ppm, δ units). The coupling constants are expressed in Hertz (Hz) and the splitting patterns are described as (singlet), bs (broad singlet), d (doublet), t (triplet), q (quartet), quint (quintet), m (multiplet).

The LC-MS analyses were carried out in accordance with the following methods:

Method A:

Column Acquity UPLC-BEH C18 (50×2.1 mm, 1.7 µm); Phase A: Milli-Q water/CH$_3$CN 95/5+0.07% formic acid; Phase B: CH$_3$CN+0.05% formic acid; flow rate: 0.6 ml/min; UV detection (DIODE array) from 210 to 400 nm; ESI+ detection in the 100-2000 m/z range; HPLC: Waters Acquity UPLC; MS: Micromass SQD Single quadrupole (Waters).

Gradient: 0 min (A: 98%, B: 2%), 0-3.00 min (A: 0%, B: 100%), 3.00-3.50 min (A: 0%, B: 100%), 3.50-4.50 min (A: 98%, B: 2%).

Method B:

Column Acquity UPLC-BEH C18 (50×2.1 mm, 1.7 µm); Phase A: water/CH$_3$CN 95/5+0.1% TFA; Phase B: water/CH$_3$CN 5/95+0.1% TFA; flow rate: 0.6 ml/min; UV detection wavelength 254 nm or BPI; ESI+ detection 3.2 kV, 25 V, 350° C.; Waters Acquity UPLC, Micromass ZQ 2000 Single quadrupole (Waters).

Gradient: 0-0.25 min (A: 95%, B: 5%), 0.25-3.30 min (A: 0%, B: 100%), 3.30-4.00 min (A: 0%, B: 100%), 4.00-4.10 min (A: 95%, B: 5%); 4.10-5.00 min (A: 95%, B: 5%).

Method C:

Column XBridge C8 (50×4.6 mm, 3.5 µm); Phase A: water+0.1% TFA; Phase B: CH$_3$CN+0.1% TFA; flow rate: 2.0 ml/min; UV detection wavelength 254 nm or BPI; ESI+ detection 3.2 kV, 25 V, 350° C.; Waters HPLC, Micromass ZQ 2000 Single quadrupole (Waters).

Gradient: 0-1.00 min (A: 95%, B: 5%), 1.00-8.00 min (A: 0%, B: 100%), 8.00-8.10 min (A: 90%, B: 10%), 8.10-8.50 (A: 95%, B: 5%), 8.50-9.50 (A: 95%, B: 5%).

Method D:

Column Acquity: XBridge C8 (50×4.6 mm, 3.5 µm); Phase A: water+0.1% TFA; Phase B: CH$_3$CN+0.1% TFA; flow rate: 2.0 ml/min; UV detection wavelength 254 nm or BPI; ESI+ detection 3.2 kV, 25 V, 350° C.; Waters HPLC, Micromass ZQ 2000 Single quadrupole (Waters).

Gradient: 0-1.00 min (A: 95%, B: 5%), 1.00-7.50 min (A: 0%, B: 100%), 7.50-8.50 min (A: 0%, B: 100%), 8.50-8.60 min (A: 95%, B: 5%), 8.60-9.60 min (A: 95%, B: 5%).

Method E:

Column Acquity: Atlantis C18 (50×2.1 mm, 3 µm); Phase A: water+0.1% TFA; Phase B: CH$_3$CN+0.1% TFA; flow rate: 0.3 ml/min; UV detection wavelength 254 nm or BPI; ESI+ detection 3.2 kV, 25 V, 350° C.; Waters HPLC, Micromass ZQ 2000 Single quadrupole (Waters).

Gradient: 0-0.20 min (A: 95%, B: 5%), 0.20-5.00 min (A: 0%, B: 100%), 5.00-6.00 min (A: 0%, B: 100%), 6.00-6.10 min (A: 95%, B: 5%), 6.10-7.00 min (A: 95%, B: 5%).

Method F:

Column Acquity UPLC-BEH C18 (50×2.1 mm, 1.7 µm); Phase A: water/MeOH 95/5+0.1% Formic acid; Phase B: water/MeOH 5/95+0.1% Formic acid; flow rate: 0.6 ml/min; UV detection wavelength 254 nm or BPI; ESI+ detection 3.2 kV, 25 V, 350° C.; Waters Acquity UPLC, Micromass ZQ 2000 Single quadrupole (Waters).

Gradient: 0-0.25 min (A: 95%, B: 5%), 0.25-3.30 min (A: 0%, B: 100%), 3.30-4.00 min (A: 0%, B: 100%), 4.00-4.10 min (A: 95%, B: 5%); 4.10-5.00 min (A: 95%, B: 5%).

Method G:

Column Acquity UPLC-BEH C18 (50×2.1 mm, 1.7 µm); Phase A: water/MeOH 95/5+0.1% Formic acid; Phase B: water/MeOH 5/95+0.1% Formic acid; flow rate: 0.6 ml/min; UV detection wavelength 254 nm or BPI; ESI+ detection 3.2 kV, 25 V, 350° C.; Waters Acquity UPLC, Micromass ZQ 2000 Single quadrupole (Waters).

Gradient: 0-0.50 min (A: 95%, B: 5%), 0.50-6.00 min (A: 0%, B: 100%), 6.00-7.00 min (A: 0%, B: 100%), 7.00-7.10 min (A: 95%, B: 5%); 7.10-8.50 min (A: 95%, B: 5%).

Method H:

Column Acquity UPLC-BEH C18 (50×2.1 mm, 1.7 µm); Phase A: water/MeOH 95/5+0.1% TFA; Phase B: water/MeOH 5/95+0.1% TFA; flow rate: 0.6 ml/min; UV detection wavelength 254 nm or BPI; ESI+ detection 3.2 kV, 25 V, 350° C.; Waters Acquity UPLC, Micromass ZQ 2000 Single quadrupole (Waters).

Gradient: 0-0.25 min (A: 95%, B: 5%), 0.25-3.30 min (A: 0%, B: 100%), 3.30-4.00 min (A: 0%, B: 100%), 4.00-4.10 min (A: 95%, B: 5%); 4.10-5.00 min (A: 95%, B: 5%).

Method I:

Column Acquity: Phenomemex Synergi Polar (50×2.0 mm, 4 µm); Phase A: water/$CH_3CN$ 95/5+0.1% TFA; Phase B: water/$CH_3CN$ 95/5+0.1% TFA; flow rate: 0.4 ml/min; UV detection wavelength 254 nm or BPI; ESI+ detection 3.2 kV, 25 V, 350° C.; Waters HPLC, Micromass ZQ 2000 Single quadrupole (Waters).

Gradient: 0-0.20 min (A: 95%, B: 5%), 0.20-5.00 min (A: 0%, B: 100%), 5.00-6.00 min (A: 0%, B: 100%), 6.00-6.10 min (A: 95%, B: 5%), 8.60-9.60 min (A: 95%, B: 5%).

Method J:

Column Acquity UPLC-BEH C18 (50×2.1 mm, 1.7 µm); Phase A: water/$CH_3CN$ 95/5+0.1% TFA; Phase B: water/$CH_3CN$ 5/95+0.1% TFA; flow rate: 0.6 ml/min; UV detection wavelength 254 nm or BPI; ESI+ detection 3.2 kV, 25 V, 350° C.; Waters Acquity UPLC, Micromass ZQ 2000 Single quadrupole (Waters).

Gradient: 0-0.50 min (A: 95%, B: 5%), 0.50-6.00 min (A: 0%, B: 100%), 6.00-7.00 min (A: 0%, B: 100%), 4.00-4.10 min (A: 95%, B: 5%); 4.10-5.00 min (A: 95%, B: 5%).

Most of the reactions were monitored by thin layer chromatography (TLC) with 0.2 mm Merck silica gel plates (60F-254), visualized with UV light (254 nm). The chromatographic columns were packed with Merck silica gel 60 (0.04-0.063 mm).

Intermediate 1: (±)-(E)-3-[4-oxo-spiro(chromane-2,3'-pyrrolidine)-6-yl]-acrylic acid methyl ester

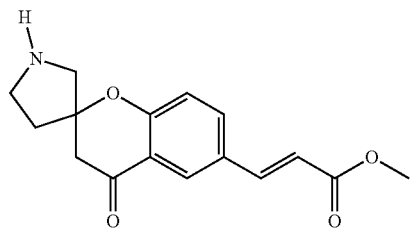 [SMILES: COC(=O)/C=C/c1ccc2c(c1)C(=O)CC1(CCNC1)O2]

Step A

A mixture of 2-hydroxy-5-bromoacetophenone (5.00 g, 23.3 mmol), 1-BOC pyrrolidin-3-one (4.30 g, 23.3 mmol) and pyrrolidine (3.87 ml, 46.5 mmol) in MeOH (20 ml) was heated under microwave irradiation for 4 h at 70° C. The solution was concentrated under vacuum and the crude mixture was purified by column chromatography (eluent: petroleum ether/EtOAc 95:5 to 7:3) to give (±)-6-bromo-4-oxo-spiro(chromane-2,3'-pyrrolidine)-1'-carboxylic acid tert-butyl ester (6.00 g) as a yellow solid.

Y=68%

LC-MS: (ES+) $MH^+$-56: 326

$^1$H NMR ($CDCl_3$) δ (ppm): 8.00 (d, J=2.64 Hz, 1H), 7.58 (dd, J=8.80, 2.05 Hz, 1 H), 6.89 (d, J=8.80 Hz, 1H), 3.68-3.85 (m, 1H), 3.50-3.66 (m, 2H), 3.23-3.46 (m, 1H), 2.88-3.04 (m, 1H), 2.84 (d, J=16.73 Hz, 1H), 2.23-2.39 (m, 1H), 1.84-2.02 (m, 1H), 1.47 (s, 9H).

Step B

A mixture of (±)-6-bromo-4-oxo-spiro(chromane-2,3'-pyrrolidine)-1'-carboxylic acid tert-butyl ester (4.70 g, 12.3 mmol), Pd(OAc)$_2$ (55.1 mg, 0.246 mmol), P(o-tol)$_3$ (149 mg, 0.490 mmol), TEA (5.13 ml, 36.8 mmol), methyl acrylate (3.32 ml, 36.9 mmol) in dry DMF (10 ml) was heated under $N_2$ atmosphere to 100° C. for 3 h. After cooling down to RT, the solution was poured into water (100 ml) and extracted with EtOAc (3 times 100 ml). The organic phase was dried over $Na_2SO_4$, filtered and evaporated under vacuum. The crude residue was recrystallized in petroleum ether:diisopropylether (1:1) to give (±)-(E)-3-[1-tert-butoxycarbonyl-4-oxo-spiro(chromane-2,3'-pyrrolidine)-6-yl]-acrylic acid methyl ester (3.85 g) as a light yellow solid.

Y=81%

LC-MS: (ES+) $MH^+$-56: 332

$^1$H NMR ($CDCl_3$) δ (ppm): 8.06 (d, J=2.05 Hz, 1H), 7.69 (dd, J=8.80, 2.05 Hz, 1H), 7.66 (d, J=15.85 Hz, 1H), 7.03 (d, J=8.80 Hz, 1H), 6.41 (d, J=16.14 Hz, 1H), 3.82 (s, 3H), 3.69-4.00 (m, 1H), 3.53-3.69 (m, 2H), 3.26-3.48 (m, 1H), 2.81-3.07 (m, 2H), 2.25-2.35 (m, 1H), 1.81-2.05 (m, 1H), 1.48 (bs, 9H).

Step C

4 M HCl in dioxane (10 ml, 80 mmol) was added to a solution of (±)-(E)-3-[1'-tert-butoxycarbonyl-4-oxo-spiro(chromane-2,3'-pyrrolidine)-6-yl]-acrylic acid methyl ester (4.30 g, 11.2 mmol) in DCM (15 ml) and the mixture was stirred at RT for 1 h. The precipitate was filtered off, washed with DCM, dried under vacuum and collected (3.3 g) as a white solid (hydrochloride salt). Y=92%

LC-MS: (ES+) $MH^+$: 288

$^1$H NMR (DMSO-$d_6$) δ (ppm): 9.65 (bs, 2H), 7.97-8.11 (m, 2H), 7.70 (d, J=15.85 Hz, 1H), 7.09 (d, J=9.39 Hz, 1H), 6.60 (d, J=16.14 Hz, 1H), 3.73 (s, 3H), 3.50-3.67 (m, 1H), 3.35-3.49 (m, 2H), 3.25-3.31 (m, 1H), 3.21 (d, J=17.02 Hz, 1H), 3.11 (d, J=17.02 Hz, 1H), 2.20-2.43 (m, 1H), 2.10 (dt, J=14.01, 9.87 Hz, 1H).

Intermediate 2: (±)-(E)-3-[4-oxo-spiro(chromane-2,3'-piperidine)-6-yl]-acrylic acid methyl ester

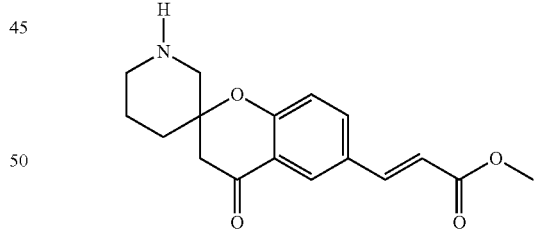

Step A

A mixture of 2-hydroxy-5-bromoacetophenone (4.36 g, 20.3 mmol), 1-BOC-piperidin-3-one (3.93 g, 20.3 mmol) and pyrrolidine (3.38 ml, 40.6 mmol) in MeOH (15 ml) was heated in the microwave apparatus at 70° C. for 3 h. The solution was then concentrated under vacuum and the crude mixture was purified by column chromatography (eluent: petroleum ether/EtOAc 9:1 to 8:2) to give (±)-6-bromo-4-oxo-spiro[chromane-2,3'-piperidine-6-yl]-1'-carboxylic acid tert-butyl ester (6.3 g) as a red oil.

Y=78%

LC-MS: (ES+) $MNa^+$: 418

$^1$H NMR ($CDCl_3$) δ (ppm): 7.98 (d, J=2.35 Hz, 1H), 7.58 (dd, J=8.80, 2.05 Hz, 1H), 6.86 (d, J=8.51 Hz, 1H), 3.89-4.06

(m, 1H), 3.72-3.89 (m, 1H), 3.12 (d, J=14.09 Hz, 1H), 3.10 (ddd, J=13.50, 9.98, 3.52 Hz, 1H), 2.75 (d, J=16.73 Hz, 1H), 2.68 (d, J=17.61 Hz, 1H), 2.02-2.17 (m, 2H), 1.05-1.99 (m, 11H).

Step B

A mixture of (±)-6-bromo-4-oxo-spiro(chromane-2,3'-piperidine)-1'-carboxylic acid tert-butyl ester (6.0 g, 15.19 mmol), Pd(OAc)$_2$ (68.1 mg, 0.304 mmol), P(o-tol)$_3$ (184.7 mg, 0.608 mmol), TEA (6.33 ml, 45.6 mmol), methyl acrylate (4.10 ml, 45.57 mmol) in dry DMF (15 ml) was heated under N$_2$ atmosphere to 100° C. for 3 h. After cooling down to RT, the solution was filtered on a celite pad and washed 3 times with EtOAc (100 ml). The filtrate was washed with water and brine. The organic phase was dried over Na$_2$SO$_4$ and evaporated under vacuum. The crude residue was purified by column chromatography (eluent: petroleum ether/EtOAc 8:2 to 7:3) to give (±)-(E)-3-[1'-tert-butoxycarbonyl-4-oxo-spiro (chromane-2,3'-piperidine)-6-yl]-acrylic acid methyl ester (6.0 g) as a yellow solid.

Y=98%

LC-MS: (ES+) MH$^+$: 402

$^1$H NMR (CDCl$_3$) δ (ppm): 7.97 (d, J=2.35 Hz, 1H), 7.91 (dd, J=8.51, 2.35 Hz, 1H), 7.65 (d, J=16.14 Hz, 1H), 7.00 (d, J=8.51 Hz, 1H), 6.48 (d, J=15.85 Hz, 1H), 3.87-3.98 (m, 1H), 3.75-3.82 (m, 1H), 3.74 (s, 3H), 3.16 (d, J=13.79 Hz, 1H), 2.97-3.10 (m, 1H), 2.87 (m, J=17.02 Hz, 1H), 2.76 (d, J=16.73 Hz, 1H), 1.99-2.09 (m, 1H), 1.68-1.87 (m, 2H), 1.47-1.60 (m, 1H), 1.30 (s, 9H).

Step C

4 M HCl in dioxane (15 ml, 60 mmol) was added to a solution of (±)-(E)-3-[1'-tert-butoxycarbonyl-4-oxo-spiro (chromane-2,3'-piperidine)-6-yl]-acrylic acid methyl ester (3.0 g, 7.48 mmol) in DCM (10 ml) and the mixture was stirred at RT for 1 h. The precipitate was filtered off, washed with DCM, dried under vacuum and collected (2.4 g) as a white solid (hydrochloride salt).

Y=95%

LC-MS: (ES+) MH$^+$: 302

$^1$H NMR (DMSO-d$_6$) δ (ppm): 9.65 (bs, 1H), 8.86 (bs, 1H), 8.05 (dd, J=8.80, 2.35 Hz, 1H), 8.02 (d, J=2.05 Hz, 1H), 7.69 (d, J=16.14 Hz, 1H), 7.16 (d, J=8.80 Hz, 1H), 6.59 (d, J=16.14 Hz, 1H), 3.72 (s, 3H), 3.41-3.55 (m, 1H), 3.11-3.27 (m, 2 H), 3.02 (d, J=17.02 Hz, 1H), 2.87 (d, J=17.02 Hz, 1H), 2.77-2.89 (m, 1H), 1.99-2.17 (m, 1H), 1.80-1.99 (m, 1H), 1.54-1.80 (m, 2H).

Intermediate 3: (±)-(E)-3-[4-oxo-spiro(chromane-2,4'-azepane)-6-yl]-acrylic acid methyl ester

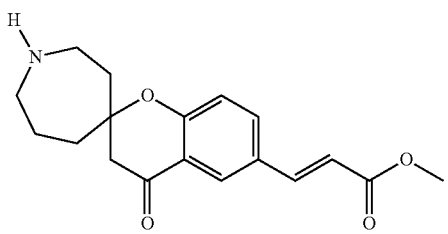 [SMILES: COC(=O)/C=C/c1ccc2c(c1)C(=O)CC1(CCCNCC1)O2]

Step A

A mixture of 2-hydroxy-5-bromoacetophenone (5.04 g, 23.4 mmol), 1-BOC-azepan-4-one (5.00 g, 23.4 mmol) and pyrrolidine (3.90 ml, 46.8 mmol) in MeOH (100 ml) was heated under reflux for 6 h. The solution was then concentrated under vacuum and water was added to the mixture. The solution was neutralized with HCl 20% and extracted with EtOAc. The organic phase was dried over Na$_2$SO$_4$ and evaporated under vacuum. The crude mixture was purified by column chromatography (eluent: petroleum ether/EtOAc 9:1 to 8:2) to give (±)-6-bromo-4-oxo-spiro[chromane-2,4'-azepane-6-yl]-1'-carboxylic acid tert-butyl ester (7.5 g).

Y=78%

LC-MS: (ES+) MNa$^+$: 432

$^1$H NMR (CDCl$_3$) δ (ppm): 7.96 (d, J=2.35 Hz, 1H), 7.56 (dd, J=8.80, 2.35 Hz, 1H), 6.89 (d, J=8.80 Hz, 1H), 3.45-3.78 (m, 2H), 3.31-3.40 (m, 1H), 3.31 (ddd, J=12.62, 10.27, 2.35 Hz, 1H), 2.78 (d, J=16.73 Hz, 1H), 2.68 (d, J=16.73 Hz, 1H), 2.09-2.27 (m, 2H), 1.72-2.03 (m, 2H), 1.55-1.72 (m, 2H), 1.48 (s, 9H).

Step B

A mixture of (±)-6-bromo-4-oxo-spiro(chromane-2,4'-azepane)-1'-carboxylic acid tert-butyl ester (7.20 g, 17.6 mmol), Pd(OAc)$_2$ (78 mg, 0.35 mmol), P(o-tol)$_3$ (213 mg, 0.70 mmol), TEA (7.32 ml, 52.7 mmol), methyl acrylate (4.74 ml, 52.7 mmol) in dry DMF (20 ml) was heated under N$_2$ atmosphere to 100° C. for 3 h. After cooling down to RT, the solution was filtered on a celite pad and washed with EtOAc (100 ml). The filtrate was washed with water and brine. The organic phase was dried over Na$_2$SO$_4$ and evaporated under vacuum. The crude residue was purified by column chromatography (eluent: petroleum ether/EtOAc 8:2 to 7:3) to give (±)-(E)-3-[1'-tert-butoxycarbonyl-4-oxo-spiro (chromane-2,4'-azepane)-6-yl]-acrylic acid methyl ester (7.1 g) as a light yellow solid.

Y=97%

LC-MS: (ES+) MNa$^+$: 438

$^1$H NMR (CDCl$_3$) δ (ppm): 8.02 (d, J=2.35 Hz, 1H), 7.66 (dd, J=8.51, 2.35 Hz, 1H), 7.65 (d, J=16.43 Hz, 1H), 7.01 (d, J=8.80 Hz, 1H), 6.39 (d, J=15.85 Hz, 1H), 3.81 (s, 3H), 3.45-3.76 (m, 2H), 3.20-3.45 (m, 2H), 2.82 (d, J=16.73 Hz, 1H), 2.71 (d, J=16.73 Hz, 1H), 2.20 (dd, J=14.38, 6.16 Hz, 2H), 1.57-2.03 (m, 4H), 1.48 (s, 9H).

Step C

4 M HCl in dioxane (20 ml, 80 mmol) was added to a solution of (±)-(E)-3-[1'-tert-butoxycarbonyl-4-oxo-spiro (chromane-2,4'-azepane)-6-yl]-acrylic acid methyl ester (6.00 g, 14.5 mmol) in DCM (20 ml) and the mixture was stirred at RT for 1 h. The precipitated product was filtered off, washed with DCM, dried under vacuum and collected (4.07 g) as a light yellow solid (hydrochloride salt).

Y=80%

LC-MS: (ES+) MH$^+$: 316

$^1$H NMR (DMSO-d$_6$) δ (ppm): 9.12 (bs, 2H), 7.88-8.16 (m, 2H), 7.68 (d, J=16.14 Hz, 1H), 7.15 (d, J=8.51 Hz, 1H), 6.57 (d, J=15.85 Hz, 1H), 3.72 (s, 3H), 3.03-3.35 (m, 4H), 2.95 (d, J=16.73 Hz, 1H), 2.89 (d, J=16.73 Hz, 1H), 2.04-2.37 (m, 3H), 1.81-2.00 (m, 2H), 1.66-1.79 (m, 1H).

Intermediate 4: (E)-3-[4-oxo-spiro(chromane-2,3'-azetidine)-6-yl]-acrylic acid methyl ester

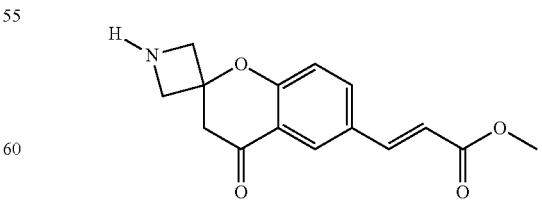

Step A

1-BOC-azetidin-3-one (2.00 g, 11.7 mmol) was added to a mixture of 2-hydroxy-5-bromoacetophenone (2.50 g, 11.7 mmol) and pyrrolidine (0.97 ml, 11.7 mmol) in MeOH (8 ml), and the reaction mixture was heated to 70° C. by MW (closed vessel) for 5 h. The solution was then concentrated under vacuum and the crude mixture was purified by column chromatography on silica gel (eluent: petroleum ether/EtOAc form 9:1 to 8:2) to give 6-bromo-4-oxo-spiro(chromane-2,3'-azetidine-6-yl)-1'-carboxylic acid tert-butyl ester (2.50 g) as a yellow solid.

Y=58%

LC-MS: (ES+) MH$^+$-56: 312

$^1$H NMR (300 MHz, DMSO-d$_6$) δ (ppm): 7.81 (dd, J=2.64, 0.59 Hz, 1H), 7.78 (dd, J=8.51, 2.64 Hz, 1H), 7.16 (dd, J=8.51, 0.59 Hz, 1H), 3.99 (d, J=9.39 Hz, 2H), 3.89 (d, J=9.68 Hz, 2H), 3.20 (s, 2H), 1.38 (s, 9H).

Step B

A mixture of 6-bromo-4-oxo-spiro(chromane-2,3'-azetidine-6-yl)-1'-carboxylic acid tert-butyl ester (2.50 g, 6.80 mmol), Pd(OAc)$_2$ (29.0 mg, 0.129 mmol), P(o-tol)$_3$ (85.0 mg, 0.279 mmol), TEA (2.80 ml, 20.4 mmol) and methyl acrylate (1.80 ml, 20.4 mmol) in dry DMF (5 ml) was heated under N$_2$ atmosphere to 100° C. for 3 h. After cooling down to RT, the solution was filtered on a celite pad and washed with EtOAc (50 ml). The filtrate was then washed with water and brine, and the organic phase was dried over Na$_2$SO$_4$ and evaporated under vacuum. The crude residue was purified by column chromatography on silica gel (eluent: petroleum ether/EtOAc 8:2 to 7:3) to give (E)-3-[1'-tert-butoxycarbonyl-4-oxo-spiro(chromane-2,3'-azetidine)-6-yl]-acrylic acid methyl ester (2.30 g) as a light yellow solid.

Y=90%

LC-MS: (ES+) MH$^+$-56: 318

$^1$H NMR (300 MHz, DMSO-d$_6$) δ (ppm): 8.03 (dd, J=8.51, 2.35 Hz, 1H), 8.01 (d, J=2.05 Hz, 1H), 7.69 (d, J=16.14 Hz, 1H), 7.21 (d, J=8.51 Hz, 1H), 6.60 (d, J=15.85 Hz, 1H), 4.01 (d, J=9.68 Hz, 2H), 3.91 (d, J=9.68 Hz, 2H), 3.72 (s, 3H), 3.21 (s, 2H), 1.39 (s, 9H).

Step C

4 M HCl in dioxane (5.0 ml) was added to a solution of (E)-3-[1-tert-butoxycarbonyl-4-oxo-spiro(chromane-2,3'-azetidine)-6-yl]-acrylic acid methyl ester (1.50 g, 4.02 mmol) in DCM (28 ml) and the mixture was stirred at RT over night. The precipitated product was filtered off, washed with DCM, dried under vacuum and collected (1.14 g, hydrochloride salt) as a white solid.

Y=92%

LC-MS: (ES+) MH$^+$: 274

$^1$H NMR (300 MHz, DMSO-d$_6$) δ (ppm): 9.44 (bs, 1H), 9.32 (bs, 1H), 8.07 (dd, J=8.80, 2.35 Hz, 1H), 8.03 (d, J=2.35 Hz, 1H), 7.70 (d, J=16.14 Hz, 1H), 7.22 (d, J=8.51 Hz, 1H), 6.62 (d, J=16.14 Hz, 1H), 4.08-4.25 (m, 4H), 3.73 (s, 3H), 3.32 (s, 2H).

Intermediate 5: (±)-(E)-3-{3,4-Dihydro-4-oxo-spiro[2H-(1,3)-benzoxazine-2,3'-piperidin]-6-yl}-acrylic acid methyl ester

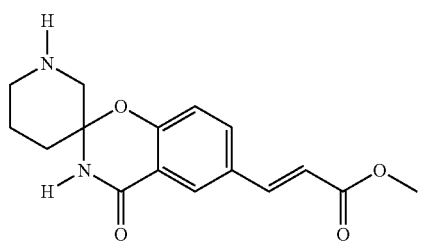 [SMILES: COC(=O)/C=C/c1ccc2c(c1)C(=O)NC1(CCCNC1)O2]

Step A

1-BOC-piperidin-3-one (4.0 g, 20 mmol) was added to a mixture of 5-bromo-2-hydroxybenzamide (2.0 g, 9.2 mmol) and pyrrolidine (0.76 ml, 9.2 mmol) in MeOH (7.5 ml), and the reaction mixture was heated to 70° C. by MW (closed vessel) for 5 h. The solution was then concentrated under vacuum and the crude mixture was purified by column chromatography on silica gel (eluent: DCM/EtOAc 7:3) to give (±)-6-bromo-3,4-dihydro-4-oxo-spiro-[2H-(1,3)-benzoxazine-2,3'-piperidine]-1'-carboxylic acid tert-butyl ester (2.50 g) as a yellow solid.

Y=68%

LC-MS: (ES+) MNa$^+$: 421

$^1$H NMR (300 MHz, DMSO-d$_6$) δ (ppm): 8.93 (bs, 1H), 7.83 (d, J=2.64 Hz, 1H), 7.57-7.79 (m, 1H), 6.65-7.16 (m, 1H), 3.92-4.17 (m, 1H), 3.70-3.89 (m, 1H), 2.80-3.17 (m, 2H), 1.97-2.19 (m, 1H), 1.58-1.93 (m, 3H), 0.82-1.52 (m, 9H).

Step B

A solution of (±)-6-bromo-3,4-dihydro-4-oxo-spiro-[2H-(1,3)-benzoxazine-2,3'-piperidine]-1'-carboxylic acid tert-butyl ester (2.50 g, 6.30 mmol) in dry DMF (5 ml) was treated with Pd(OAc)$_2$ (26.0 mg, 0.130 mmol), P(o-tol)$_3$ (76.6 mg, 0.252 mmol), TEA (2.6 ml, 19 mmol) and methyl acrylate (1.7 ml, 19 mmol) following the procedure described for Intermediate 4, Step B, to give (±)-(E)-3-{1'-tert-butoxycarbonyl-3,4-dihydro-4-oxo-spiro[2H-(1,3)-benzoxazine-2,3'-piperidin]-6-yl}-acrylic acid methyl ester (2.30 g) as a light orange solid.

Y=75%

LC-MS: (ES+) MNa$^+$: 425

$^1$H NMR (300 MHz, DMSO-d$_6$) δ (ppm): 8.88 (bs, 1H), 7.86-8.11 (m, 2H), 7.69 (d, J=15.85 Hz, 1H), 6.72-7.12 (m, 1H), 6.57 (d, J=16.14 Hz, 1H), 3.93-4.11 (m, 1H), 3.76-3.89 (m, 1H), 3.72 (s, 3H), 2.79-3.15 (m, 2H), 2.02-2.18 (m, 1H), 1.60-1.95 (m, 3H), 1.05-1.51 (m, 9H).

Step C (±)-(E)-3-{1'-Tert-butoxycarbonyl-3,4-dihydro-4-oxo-spiro[2H-(1,3)-benzoxazine-2,3'-piperidin]-6-yl}-acrylic acid methyl ester (1.90 g, 4.72 mmol) in DCM (33 ml) was treated with 4 M HCl in dioxane (5.90 ml) as described for Intermediate 4, Step C, giving (±)-(E)-3-{3,4-dihydro-4-oxo-spiro[2H-(1,3)-benzoxazine-2,3'-piperidin]-6-yl}-acrylic acid methyl ester (1.35 g, hydrochloride salt) as a light brown solid.

Y=84%

LC-MS: (ES+) MH$^+$:303

$^1$H NMR (300 MHz, DMSO-d$_6$) δ (ppm): 9.43-9.72 (m, 1H), 8.70-9.03 (m, 1H), 8.05 (d, J=2.05 Hz, 1H), 7.98 (dd, J=8.66, 2.20 Hz, 1H), 7.70 (d, J=16.14 Hz, 1H), 7.19 (d, J=8.51 Hz, 1H), 6.59 (d, J=15.85 Hz, 1H), 3.73 (s, 3H), 3.46-3.63 (m, 1H), 2.77-3.32 (m, 3H), 1.56-2.23 (m, 4H).

Intermediate 6: (±)-6-bromospiro[chroman-2,3'-piperidin]-4-one

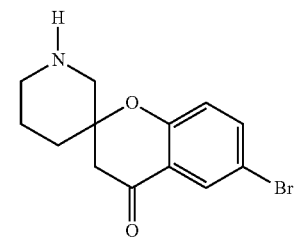 [SMILES: O=C1CC2(CCCNC2)Oc2ccc(Br)cc21]

(±)-6-Bromo-4-oxo-spiro[chromane-2,3'-piperidine-6-yl]-1'-carboxylic acid tert-butyl ester (Intermediate 2 STEP A, 2.50 g, 6.31 mmol) was dissolved in DCM (20 ml) and 4 M HCl in dioxane (5 ml) was added to the resulting solution. The mixture was stirred for 5 h at RT and the resulting precipitate was collected by filtration to give (±)-6-bromospiro[chroman-2,3'-piperidin]-4-one hydrochloride (2.079 g).

Y=89%

LC-MS: 297

$^1$H NMR (DMSO-d$_6$) δ (ppm): 9.69 (bs, 1H), 8.83 (bs, 1H), 7.82 (d, J=2.93 Hz, 1H), 7.80 (dd, J=6.75, 2.64 Hz, 1H), 7.11 (d, J=9.10 Hz, 1H), 3.39-3.54 (m, 1H), 3.10-3.26 (m, 2H), 3.00 (d, J=17.02 Hz, 1H), 2.86 (d, J=17.31 Hz, 1H), 2.62-2.86 (m, 1H), 1.98-2.18 (m, 1H), 1.78-1.98 (m, 1H), 1.56-1.78 (m, 2H).

Intermediate 7: (−)-6-bromospiro[chroman-2,3'-piperidin]-4-one

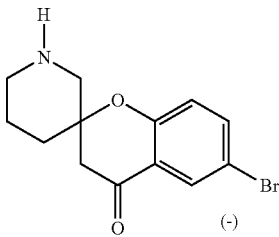 [SMILES: O=C1CC2(CCCNC2)Oc2ccc(Br)cc21]

(R)-2-Acetoxy-2-phenylacetic acid (0.732 g, 3.77 mmol) was dissolved in DCM (50 ml). TEA (1.577 ml, 11.32 mmol), EDC (1.085 g, 5.66 mmol) and HOBt.H$_2$O (0.866 g, 5.62 mmol) were added and the mixture was stirred at RT for 10 min.

(±)-6-Bromospiro[chroman-2,3'-piperidin]-4-one hydrochloride (Intermediate 6, 1.39 g, 4.12 mmol) was added and the mixture was stirred at RT for 18 h and then washed with 5% NaHCO$_3$ and with brine. The organic layer was dried over Na$_2$SO$_4$ and evaporated to dryness.

The crude mixture of diastereoisomers was purified by silica gel chromatography (eluent: petroleum ether/EtOAc from 6:4 to 3:7). The less polar isomer that eluted first (430 mg, 22%, $^1$H NMR (DMSO-d$_6$) δ (ppm): 7.68-7.83 (m, 2H), 7.19-7.65 (m, 5H), 6.94 (d, J=8.80 Hz, 1H), 6.38 (s, 1H), 4.11 (d, J=13.50 Hz, 1H), 3.45-3.87 (m, 1H), 2.88-3.19 (m, 2H), 2.77 (d, J=17.02 Hz, 1H), 2.67 (d, J=17.02 Hz, 1H), 2.10 (s, 3H), 1.36-2.02 (m, 3H), 1.00-1.32 (m, 1H)) was then dissolved in EtOH (25 ml) and 12 M HCl (25 ml). The resulting mixture was stirred at reflux overnight. Then EtOH was evaporated and the residue was basified with 20% NaOH and extracted with EtOAc. The organic phase was dried over Na$_2$SO$_4$ and evaporated to dryness to give (−)-6-bromospiro[chroman-2,3'-piperidin]-4-one (216 mg).

Y=80%

Optical rotation: α$_D$=−19.28°, c=0.5 g/100 ml in MeOH (hydrochloride salt)

$^1$H NMR (DMSO-d$_6$) δ (ppm): 7.76 (d, J=2.35 Hz, 1H), 7.71 (dd, J=8.51, 2.64 Hz, 1H), 7.04 (d, J=8.80 Hz, 1H), 2.91 (d, J=16.73 Hz, 1H), 2.78 (d, J=17.02 Hz, 1H), 2.74-2.90 (m, 2H), 2.65-2.74 (m, 1H), 2.54-2.64 (m, 1H), 1.80-1.90 (m, 1H), 1.52-1.79 (m, 2H), 1.31-1.47 (m, 1H).

Intermediate 8: (+)-6-bromospiro[chroman-2,3'-piperidin]-4-one

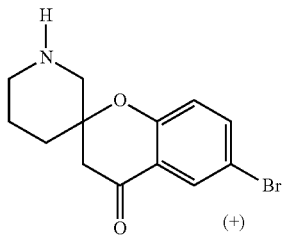 [SMILES: O=C1CC2(CCCNC2)Oc2ccc(Br)cc21]

(R)-2-Acetoxy-2-phenylacetic acid (0.732 g, 3.77 mmol) was dissolved in DCM (50 ml). TEA (1.577 ml, 11.32 mmol), EDC (1.08 g, 5.66 mmol) and HOBt.H$_2$O (0.866 g, 5.66 mmol) were added and the mixture was stirred at RT for 10 min.

(±)-6-Bromospiro[chroman-2,3'-piperidin]-4-one hydrochloride (Intermediate 6, 1.39 g, 4.12 mmol) was added and the mixture was stirred at RT for 18 h. The organic layer was then washed with 5% NaHCO$_3$ and with brine, dried over Na$_2$SO$_4$ and evaporated to dryness.

The crude mixture of the diastereoisomers was purified by silica gel chromatography (eluent: petroleum ether/EtOAc from 6:4 to 3:7). The more polar isomer (523 mg, 29%, $^1$H NMR (DMSO-d$_6$) δ (ppm): 7.67-7.85 (m, 2H), 7.30-7.66 (m, 5H), 6.73 (d, J=9.39 Hz, 1H), 6.35 (s, 1H), 4.46 (d, J=13.50 Hz, 1H), 3.62-4.02 (m, 1H), 2.87-3.19 (m, 2H), 2.80 (s, 2H), 2.03 (s, 3H), 1.41-1.94 (m, 2H), 0.73-1.31 (m, 2H)) was then dissolved in EtOH (25 ml) and 12 M HCl (25 ml). The resulting mixture was stirred at reflux overnight. Then EtOH was evaporated and the residue was basified with 20% NaOH and extracted with EtOAc. The organic phase was dried over Na$_2$SO$_4$ and evaporated to dryness to give (+)-6-bromospiro[chroman-2,3'-piperidin]-4-one (267 mg).

Y=81%

Optical rotation: α$_D$=+12.16 c=0.50 g/100 ml in MeOH (hydrochloride salt).

$^1$H NMR (DMSO-d$_6$) δ (ppm): 7.76 (d, J=2.35 Hz, 1H), 7.71 (dd, J=8.51, 2.64 Hz, 1H), 7.04 (d, J=8.80 Hz, 1H), 2.91 (d, J=16.73 Hz, 1H), 2.78 (d, J=17.02 Hz, 1H), 2.74-2.90 (m, 2H), 2.65-2.74 (m, 1H), 2.54-2.64 (m, 1H), 1.80-1.90 (m, 1H), 1.52-1.79 (m, 2H), 1.31-1.47 (m, 1H).

Intermediate 9: (E)-3-{8-Fluoro-4-oxo-spiro[chromane-2,4'-piperidine]-6-yl}-acrylic acid methyl ester

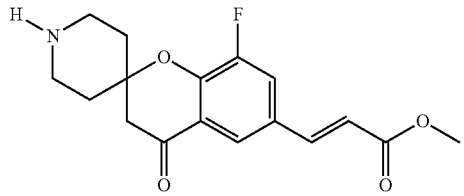 [SMILES: COC(=O)/C=C/c1cc(F)c2c(c1)C(=O)CC1(CCNCC1)O2]

Step A

A mixture of 5-bromo-3-fluoro-2-hydroxyacetophenone (4.30 g, 18.5 mmol), 1-BOC-piperidin-4-one (3.68 g, 18.5 mmol) and pyrrolidine (1.97 g, 27.7 mmol) in MeOH (50 ml) was heated to reflux for 6 h. The solvent was removed, the residue was then dissolved in AcOEt and rinsed with NaHCO₃ 5%. The organic phase was washed with brine, dried over Na₂SO₄ and evaporated. The crude mixture was purified by column chromatography (eluent: petroleum ether/EtOAc from 9:1 to 8:2) to give 8-fluoro-6-bromo-4-oxo-spiro[chromane-2,4'-piperidine]-1'-carboxylic acid tert-butyl ester (4.18 g).

Y=55%

¹H NMR (300 MHz, DMSO-d₆) δ (ppm): 7.90 (dd, J=10.12, 2.49 Hz, 1H), 7.63 (dd, J=2.35, 1.47 Hz, 1H), 3.55-3.83 (m, 2H), 3.02-3.16 (m, 2H), 2.96 (s, 2H), 1.83-1.98 (m, 2H), 1.53-1.74 (m, 2H), 1.40 (s, 9H).

Step B

8-Fluoro-6-bromo-4-oxo-spiro[chromane-2,4'-piperidine]-1-carboxylic acid tert-butyl ester (4.17 g, 10.1 mmol) was dissolved in DMF (30 ml). TEA (1.40 ml, 10.0 mmol) and methyl acrylate (2.60 g, 30.2 mmol) were added and the mixture was degassed with nitrogen. P(o-tol)₃ (0.123 g, 0.403 mmol) and Pd(OAc)₂ (45 mg, 0.20 mmol) were added and the mixture was heated to 100° C. Further Pd(OAc)₂ (45 mg, 0.20 mmol) was added over 5 h and then heating continued overnight. The resulting brown solution was partitioned between between Et₂O and H₂O and the organic layer was washed with brine, dried over Na₂SO₄ and evaporated to dryness. The crude product was purified by column chromatography (eluent: petroleum ether/EtOAc from 9:1 to 7:3) to give (E)-3-{1-tert-butoxycarbonyl-8-fluoro-4-oxo-spiro[chromane-2,4'-piperidine]-6-yl}-acrylic acid methyl ester (2.79 g).

Y=66%

¹H NMR (300 MHz, DMSO-d₆) δ (ppm): 8.08 (dd, J=12.03, 2.05 Hz, 1H), 7.83 (s, 1H), 7.66 (d, J=15.85 Hz, 1H), 6.65 (d, J=16.14 Hz, 1H), 3.73-3.82 (m, 2H), 3.72 (s, 3H), 3.00-3.19 (m, 2H), 2.97 (s, 2H), 1.86-1.97 (m, 2H), 1.58-1.77 (m, 2H), 1.41 (s, 9H).

Step C

A mixture of (E)-3-{1'-tert-butoxycarbonyl-8-fluoro-4-oxo-spiro[chromane-2,4'-piperidine]-6-yl}-acrylic acid methyl ester (2.78 g, 6.63 mmol) and 4 M HCl in dioxane (3 ml) in DCM (50 ml) was stirred at RT for 5 h. The solvent was removed, the residue was triturated in DCM and filtered to give the title compound as its hydrochloride salt (2.04 g).

Y=87%

¹H NMR (300 MHz, DMSO-d₆) δ (ppm): 9.08 (bs, 2H), 8.12 (dd, J=12.03, 2.05 Hz, 1H), 7.85 (s, 1H), 7.67 (d, J=15.85 Hz, 1H), 6.67 (d, J=15.85 Hz, 1H), 3.73 (s, 3H), 3.15-3.25 (m, 2H), 3.04 (s, 2H), 2.96-3.11 (m, 2H), 2.12-2.27 (m, 2H), 1.91-2.04 (m, 2H).

Intermediate 10: (E)-3-{8-Methyl-4-oxo-spiro[chromane-2,4'-piperidine]-6-yl}-acrylic acid methyl ester

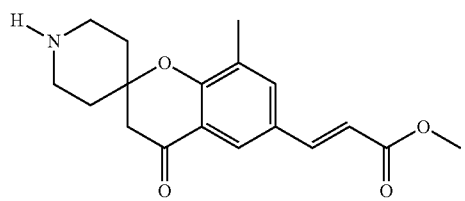 [SMILES: COC(=O)/C=C/c1cc(C)c2c(c1)C(=O)CC1(CCNCC1)O2]

The compound was prepared starting from 5-bromo-3-methyl-2-hydroxyacetophenone following the experimental procedure described for Intermediate 9. The title compound was obtained as its hydrochloride salt.

¹H NMR (300 MHz, DMSO-d₆) δ (ppm): 8.84 (bs, 2H), 7.96 (d, J=1.76 Hz, 1H), 7.85 (d, J=2.35 Hz, 1H), 7.64 (d, J=16.14 Hz, 1H), 6.57 (d, J=16.14 Hz, 1H), 3.72 (s, 3H), 2.99-3.25 (m, 4H), 2.94 (s, 2H), 2.30 (s, 3H), 2.05-2.24 (m, 2H), 1.83-2.04 (m, 2H).

Example 1

(±)-(E)-3-[4-oxo-spiro(chromane-2,3'-pyrrolidine)-6-yl]-N-hydroxy-acrylamide

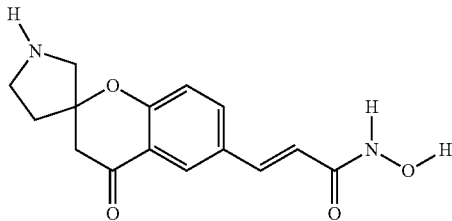 [SMILES: O=C(/C=C/c1ccc2c(c1)C(=O)CC1(CCNC1)O2)NO]

Step A

HCl 20% aq. (5 ml, 30 mmol) was added to a suspension of (±)-(E)-3-[1-tert-butoxycarbonyl-4-oxo-spiro(chromane-2,3'-pyrrolidine)-6-yl]-acrylic acid methyl ester (Intermediate 1, Step B) (464 mg, 1.2 mmol) in glacial AcOH (5 ml). The mixture was stirred at 85° C. for 3 h and then evaporated under vacuum to give (±)-(E)-3-[4-oxo-spiro(chromane-2,3'-pyrrolidine)-6-yl]-acrylic acid (370 mg) as a white solid (hydrochloride salt).

Y=quantitative

LC-MS: (ES+) MH⁺: 274

¹H NMR (DMSO-d₆) δ (ppm): 12.30 (bs, 1H), 9.79 (bs, 1H), 9.67 (bs, 1H), 7.87-8.19 (m, 2H), 7.61 (d, J=15.85 Hz, 1H), 7.08 (d, J=9.39 Hz, 1H), 6.48 (d, J=15.85 Hz, 1H), 3.24-3.66 (m, 4H), 3.21 (d, J=17.02 Hz, 1H), 3.11 (d, J=17.02 Hz, 1H), 2.22-2.43 (m, 1H), 2.10 (dt, J=13.86, 9.94 Hz, 1H).

Step B

TEA (0.50 ml, 3.6 mmol) was added to the suspension of (±)-(E)-3-[4-oxo-spiro(chromane-2,3'-pyrrolidine)-6-yl]-acrylic acid (370 mg, 1.20 mmol) in DCM (10 ml). After complete dissolution of the acid, BOC anhydride (314 mg, 1.44 mmol) was added. The mixture was stirred at RT for 1 h. The solution was poured into water (10 ml), neutralized with aqueous 5% citric acid solution and extracted with DCM (3 times 10 ml). The organic phase was dried over Na₂SO₄ and evaporated under vacuum. The crude product (406 mg) was used in the next step without purification.

Y=91%

LC-MS: (ES+) MH⁺-56: 318

¹H NMR (DMSO-d₆) δ (ppm): 7.78-8.20 (m, 2H), 7.57 (d, J=15.85 Hz, 1H), 7.11 (d, J=9.10 Hz, 1H), 6.46 (d, J=15.85 Hz, 1H), 3.61 (d, J=12.32 Hz, 1H), 3.25-3.55 (m, 3H), 3.15 (d, J=16.73 Hz, 1H), 2.98 (d, J=17.02 Hz, 1H), 2.11-2.28 (m, 1H), 1.88-2.11 (m, 1H), 1.27-1.52 (m, 9H).

Step C

TEA (0.271 ml, 1.95 mmol) was added to solution of (±)-(E)-3-[1'-tert-butoxycarbonyl-4-oxo-spiro(chromane-2,3'-pyrrolidine)-6-yl]-acrylic acid (484 mg, 1.29 mmol) in DCM (10 ml). The mixture was cooled down to 0° C., and EDC (372 mg, 1.95 mmol) and HOBt (263 mg, 1.95 mmol) were added. The mixture was stirred at 0° C. for 3 h, then NH₂OTHP (182 mg, 1.56 mmol) was added and the mixture was stirred at RT overnight. The solution was washed with aqueous 5% NaHCO$_3$ solution and brine. The organic layer was then dried over Na$_2$SO$_4$ and evaporated. The crude residue was purified by column chromatography (eluent: DCM/MeOH 98:2) to give (±)-(E)-3-[1'-tert-butoxycarbonyl-4-oxo-spiro(chromane-2,3'-pyrrolidine)-6-yl]-N-(tetrahydro-pyran-2-yloxy)-acrylamide (499 mg) as a light yellow solid.

Y=89%

LC-MS: (ES+) MH$^+$: 473

$^1$H NMR (DMSO-d$_6$) δ (ppm): 11.13 (bs, 1H), 7.94 (d, J=2.05 Hz, 1H), 7.81 (d, J=9.10 Hz, 1H), 7.49 (d, J=15.55 Hz, 1H), 7.12 (d, J=8.80 Hz, 1H), 6.48 (d, J=16.43 Hz, 1H), 4.91 (bs, 1H), 3.81-4.03 (m, 1H), 3.52-3.69 (m, 2H), 3.32-3.52 (m, 3H), 3.15 (d, J=17.02 Hz, 1H), 2.98 (d, J=17.31 Hz, 1H), 2.09-2.24 (m, 1H), 1.90-2.09 (m, 1H), 1.70 (bs, 3H), 1.54 (bs, 3H), 1.40 (m, 9H).

Step D

1 M HCl in Et$_2$O (5 ml, 5 mmol) was added dropwise to a solution of (±)-(E)-3-[1'-tert-butoxycarbonyl-4-oxo-spiro(chromane-2,3'-pyrrolidine)-6-yl]-N-(tetrahydro-pyran-2-yloxy)-acrylamide (280 mg, 0.59 mmol) in DCM (2 ml). The mixture was stirred at RT for 1 h. The precipitate was filtered off, washed with DCM, dried under vacuum and collected (108 mg) as a white solid (hydrochloride salt).

Y=57%

LC-MS: Method B, rt=0.91; (ES+) MH$^+$: 289

$^1$H NMR (DMSO-d$_6$) δ (ppm): 9.74 (bs, 1H), 9.61 (bs, 1H), 7.93 (d, J=2.05 Hz, 1H), 7.82 (dd, J=8.80, 2.05 Hz, 1H), 7.45 (d, J=15.55 Hz, 1H), 7.09 (d, J=8.80 Hz, 1H), 6.46 (d, J=15.55 Hz, 1H), 3.55 (dd, J=12.47, 5.72 Hz, 1H), 3.42 (bs, 2H), 3.24-3.37 (m, 1H), 3.20 (d, J=17.02 Hz, 1H), 3.10 (d, J=17.02 Hz, 1H), 2.21-2.43 (m, 1H), 2.09 (dt, J=14.09, 9.83 Hz, 1H).

Example 2

(±)-(E)-3-[1'-Benzyl-4-oxo-spiro(chromane-2,3'-pyrrolidine)-6-yl]-N-hydroxy-acrylamide

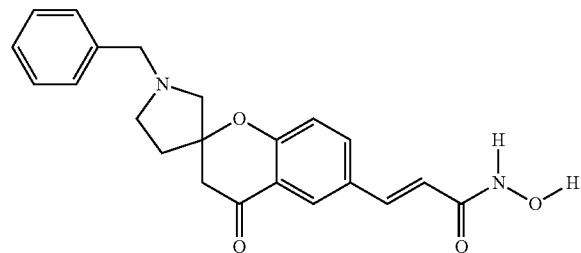 [SMILES: O=C(/C=C/c1ccc2c(c1)C(=O)CC1(CCN(Cc3ccccc3)C1)O2)NO]

Step A

A suspension of (±)-(E)-3-[4-oxo-spiro(chromane-2,3'-pyrrolidine)-6-yl]-acrylic acid methyl ester hydrochloride salt (440 mg, 1.36 mmol, Intermediate 1) in aqueous 10% NaHCO$_3$ solution was extracted with DCM (3×10 ml). The organic phase was dried over Na$_2$SO$_4$ and evaporated. The resulting oil was dissolved in DCM (15 ml), treated with benzaldehyde (0.166 ml, 1.63 mmol) and NaBH(OAc)$_3$ (433 mg, 2.04 mmol), and the resulting clear solution was stirred at RT for 2 h. Water was added to the mixture and the pH was brought to basic conditions with NH$_3$. The mixture was extracted with DCM (3×10 ml). The organic layer was dried, evaporated, and the crude residue was purified by column chromatography (eluent: petroleum ether/EtOAc 7:3) to give (±)-(E)-3-[1'-benzyl-4-oxo-spiro(chromane-2,3'-pyrrolidine)-6-yl]-acrylic acid methyl ester (482 mg) as a light yellow solid.

Y=94%

LC-MS: (ES+) MH$^+$: 378

$^1$H NMR (CDCl$_3$) δ (ppm): 8.02 (d, J=2.35 Hz, 1H), 7.65 (dd, J=8.80, 2.35 Hz, 1H), 7.65 (d, J=15.55 Hz, 1H), 7.13-7.39 (m, 5H), 7.03 (d, J=8.80 Hz, 1H), 6.39 (d, J=16.14 Hz, 1H), 3.82 (s, 3H), 3.71 (d, J=12.91 Hz, 1H), 3.66 (d, J=13.20 Hz, 1H), 2.95 (d, J=16.43 Hz, 1H), 2.89 (d, J=16.43 Hz, 1H), 2.80-2.97 (m, 2H), 2.63-2.80 (m, 2H), 2.26 (ddd, J=13.35, 7.78, 5.28 Hz, 1H), 1.92-2.12 (m, 1H).

Step B (±)-(E)-3-[1'-Benzyl-4-oxo-spiro(chromane-2,3'-pyrrolidine)-6-yl]-acrylic acid methyl ester (472 mg, 1.25 mmol) was hydrolyzed with aqueous 20% HCl solution and AcOH following the procedure described in Example 1, Step A, giving (±)-(E)-3-[1'-benzyl-4-oxo-spiro(chromane-2,3'-pyrrolidine)-6-yl]-acrylic acid (450 mg) as a white solid (hydrochloride salt).

Y=90%

LC-MS: (ES+) MH$^+$: 364

$^1$H NMR (DMSO-d$_6$, 353K) δ (ppm): 7.96 (d, J=2.35 Hz, 1H), 7.93 (dd, J=8.51, 2.35 Hz, 1H), 7.53-7.71 (m, 3H), 7.36-7.52 (m, 3H), 7.14 (d, J=8.51 Hz, 1H), 6.44 (d, J=16.14 Hz, 1H), 4.44 (d, J=13.50 Hz, 1H), 4.40 (d, J=13.79 Hz, 1H), 3.36-3.68 (m, 4H), 3.22 (d, J=17.02 Hz, 1H), 3.10 (d, J=17.02 Hz, 1H), 2.22-2.47 (m, 2H).

Step C (±)-(E)-3-[1'Benzyl-4-oxo-spiro(chromane-2,3'-pyrrolidine)-6-yl]-acrylic acid hydrochloride salt (450 mg, 1.12 mmol) was treated with NH$_2$OTHP following the procedure described in Example 1, Step C, giving (±)-(E)-3-[1'-benzyl-4-oxo-spiro(chromane-2,3'-pyrrolidine)-6-yl]-N-(tetrahydro-pyran-2-yloxy)-acrylamide (226 mg) as a light yellow solid.

Y=43%

LC-MS: (ES+) MH$^+$: 463

$^1$H NMR (DMSO-d$_6$) δ (ppm): 11.13 (bs, 1H), 7.90 (d, J=2.05 Hz, 1H), 7.67-7.84 (m, 1H), 7.47 (d, J=15.85 Hz, 1H), 7.16-7.39 (m, 5H), 7.10 (d, J=8.80 Hz, 1H), 6.46 (d, J=16.14 Hz, 1H), 4.79-5.00 (m, 1H), 3.86-4.10 (m, 1H), 3.62 (s, 2H), 3.47-3.58 (m, 1H), 3.01 (d, J=17.02 Hz, 1H), 2.95 (d, J=17.02 Hz, 1H), 2.55-2.88 (m, 4H), 1.88-2.18 (m, 2H), 1.47-1.83 (m, 6H).

Step D

1 M HCl in Et$_2$O (5 ml, 5 mmol) was added dropwise to a solution of (±)-(E)-3-[1'-benzyl-4-oxo-spiro(chromane-2,3'-pyrrolidine)-6-yl]-N-(tetrahydro-pyran-2-yloxy)-acrylamide (172 mg, 0.37 mmol) in DCM (3 ml). After 1 h stirring a white solid precipitated, which was then filtered off, washed with DCM, dried under vacuum and collected to give 83 mg of (±)-(E)-3-[1'-benzyl-4-oxo-spiro(chromane-2,3'-pyrrolidine)-6-yl]-N-hydroxy-acrylamide as its hydrochloride salt.

Y=54%

LC-MS: Method B, rt=1.13; (ES+) MH$^+$: 379

$^1$H NMR (DMSO-d$_6$) δ (ppm): 7.92 (d, J=2.35 Hz, 1H), 7.80 (dd, J=8.66, 2.20 Hz, 1H), 7.57-7.73 (m, 2H), 7.36-7.54 (m, 4H), 7.14 (d, J=8.51 Hz, 1H), 6.52 (d, J=15.85 Hz, 1H), 4.46 (d, J=12.91 Hz, 1H), 4.40 (d, J=13.50 Hz, 1H), 3.40-3.67 (m, 4H), 3.22 (d, J=17.02 Hz, 1H), 3.09 (d, J=17.02 Hz, 1H), 2.19-2.48 (m, 2H).

Example 3

(−)-(E)-3-[1'-Benzyl-4-oxo-spiro(chromane-2,3'-pyrrolidine)-6-yl]-N-hydroxy-acrylamide

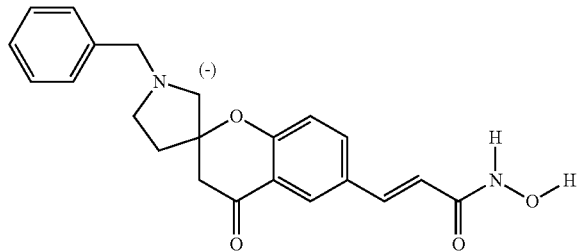 [SMILES: O=C(/C=C/c1ccc2c(c1)C(=O)CC1(CCN(Cc3ccccc3)C1)O2)NO]

Step A

TEA (1.89 ml, 13.6 mmol) was added to solution of (S)-2-(6-methoxynaphthalen-2-yl)propanoic acid (1.57 g, 6.81 mmol) in DCM (80 ml). The mixture was cooled down to 0° C., and EDC (1.95 g, 10.2 mmol) and HOBt (1.38 g, 10.2 mmol) were added. The mixture was stirred at 0° C. for 2 h, then (±)-(E)-3-[4-oxo-spiro(chromane-2,3'-pyrrolidine)-6-yl]-acrylic acid methyl ester hydrochloric salt (Intermediate 1, 2.20 g, 6.81 mmol) previous treated with TEA (0.947 ml, 6.81 mmol) in DCM (20 ml) was added and the mixture was stirred at RT overnight. The solution was washed with aqueous 5% NaHCO$_3$ solution and brine. The organic layer was then dried over Na$_2$SO$_4$ and evaporated. The crude residue was purified by column chromatography (eluent: DCM/i-PrOH 99:1) and the diastereoisomers were separated. The less polar one was re-crystallized from i-PrOH to give (+)-(E)-3-[1'-[(S)-2-(6-methoxynaphthalen-2-yl)propanoyl]-4-oxo-spiro(chromane-2,3'-pyrrolidine)-6-yl]-acrylic acid methyl ester (980 mg) as a white solid.

Y=29%

LC-MS: (ES+) MH$^+$: 500

Optical rotation: $\alpha_D$=+5.9°, c=1.025 g/100 ml in DCM $^1$H NMR (CDCl$_3$) δ (ppm): 8.01 (d, J=2.35 Hz, 1H), 7.48-7.82 (m, 5H), 7.38 (ddd, J=10.78, 8.73, 1.61 Hz, 1H), 7.10-7.25 (m, 2H), 7.01 and 6.59 (d, J=8.51 Hz, 1H), 6.41 (d, J=16.14 Hz, 1H), 4.02-4.17 (m, 1H), 3.96 (s, 3H), 3.82 (s, 3H), 3.65-3.91 (m, 3H), 3.28-3.57 (m, 1H), 2.95 and 2.79 (d, J=16.73 Hz, 1H), 2.86 (d, J=16.73 Hz, 1H), 2.15-2.39 (m, 1H), 1.69-2.15 (m, 1H), 1.56 (d, J=6.16 Hz, 3 H).

Step B

HCl 20% aq. (5 ml, 30 mmol) was added to a suspension of (+)-(E)-3-[1'-[(S)-2-(6-methoxynaphthalen-2-yl)propanoyl]-4-oxo-spiro(chromane-2,3'-pyrrolidine)-6-yl]-acrylic acid methyl ester (926 mg, 1.85 mmol) in glacial AcOH (5 ml). The mixture was stirred in the microwave oven at 120° C. for 3 h. Water (5 ml) was added and the reaction mixture was extracted three times with DCM. The aqueous phase was evaporated under vacuum. MeOH (25 ml) and a catalytic amount of H$_2$SO$_4$ were added and the mixture was heated to 70° C. overnight. The solution was poured into water and NH$_3$ was added to adjust the pH value to 9-10. The aqueous phase was extracted with DCM, dried over Na$_2$SO$_4$ and filtered. The solvent was evaporated to give (+)-(E)-3-[4-oxo-spiro(chromane-2,3'-pyrrolidine)-6-yl]-acrylic acid methyl ester (210 mg) as a yellow oil (free base).

Y=39.5%

LC-MS: (ES+) MH$^+$: 288

Optical rotation: $\alpha_D$=+1.97°, c=0.72 g/100 ml in DCM $^1$H NMR (DMSO-d$_5$) δ (ppm): 7.99 (d, J=2.05 Hz, 1H), 7.96 (dd, J=8.51, 2.35 Hz, 1H), 7.67 (d, J=16.14 Hz, 1H), 7.06 (d, J=8.51 Hz, 1H), 6.56 (d, J=16.14 Hz, 1H), 3.72 (s, 3H), 2.74-3.10 (m, 6H), 1.88-2.10 (m, 1H), 1.65-1.85 (m, 1H).

Step C (+)-(E)-3-[4-Oxo-spiro(chromane-2,3'-pyrrolidine)-6-yl]-acrylic acid methyl ester (180 mg, 0.63 mmol) was treated with benzaldehyde and NaBH(OAc)$_3$ according with procedure used for Example 2, Step A to give (+)-(E)-3-[1'-benzyl-4-oxo-spiro(chromane-2,3'-pyrrolidine)-6-yl]-acrylic acid methyl ester (180 mg).

Y=76%

LC-MS: (ES+) MH$^+$: 378

Optical rotation: $\alpha_D$=+1.68°, c=0.96 g/100 ml in DCM $^1$H NMR (DMSO-d$_6$) δ (ppm): 7.97 (d, J=2.35 Hz, 1H), 7.97 (dd, J=9.39, 2.35 Hz, 1H), 7.66 (d, J=16.14 Hz, 1H), 7.17-7.35 (m, 5H), 7.10 (d, J=9.10 Hz, 1H), 6.56 (d, J=16.14 Hz, 1H), 3.72 (s, 3H), 3.61 (s, 2H), 2.91-3.04 (m, 2H), 2.69-2.89 (m, 2H), 2.53-2.67 (m, 2H), 1.86-2.21 (m, 2H).

Step D (−)-(E)-3-[1'-Benzyl-4-oxo-spiro(chromane-2,3'-pyrrolidine)-6-yl]-acrylic acid methyl ester (130 mg, 0.34 mmol) was hydrolyzed using aqueous HCl (20%) solution and AcOH following the procedure described in Example 1, Step A, giving (−)-(E)-3-[1'-benzyl-4-oxo-spiro(chromane-2,3'-pyrrolidine)-6-yl]-acrylic acid (120 mg) as a white solid (hydrochloride salt).

Y=88%

LC-MS: (ES+) MH$^+$: 364

Optical rotation: $\alpha_D$=−3.4°, c=0.43 g/100 ml in MeOH $^1$H NMR (DMSO-d$_6$) δ (ppm): 11.01-11.75 (m, 1H), 7.91-8.12 (m, 2H), 7.53-7.71 (m, 3H), 7.37-7.53 (m, 3H), 6.95-7.26 (m, 1H), 6.30-6.57 (m, 1H), 4.29-4.58 (m, 2H), 2.91-3.67 (m, 6H), 1.98-2.45 (m, 2H).

Step E (−)-(E)-3-[1'-Benzyl-4-oxo-spiro(chromane-2,3'-pyrrolidine)-6-yl]-acrylic acid hydrochloride salt (110 mg, 0.275 mmol) was treated with NH$_2$OTHP following the procedure described in Example 1, Step C, giving (E)-3-[1'-benzyl-4-oxo-spiro(chromane-2,3'-pyrrolidine)-6-yl]-N-(tetrahydropyran-2-yloxy)-acrylamide (80 mg) as a light yellow solid.

Y=63%

LC-MS: (ES+) MH$^+$: 463

$^1$H NMR (DMSO-d$_6$) δ (ppm): 11.13 (bs, 1H), 7.90 (d, J=2.05 Hz, 1H), 7.67-7.84 (m, 1H), 7.47 (d, J=15.85 Hz, 1H), 7.16-7.39 (m, 5H), 7.10 (d, J=8.80 Hz, 1H), 6.46 (d, J=16.14 Hz, 1H), 4.79-5.00 (m, 1H), 3.86-4.10 (m, 1H), 3.62 (s, 2H), 3.47-3.58 (m, 1H), 3.01 (d, J=17.02 Hz, 1H), 2.95 (d, J=17.02 Hz, 1H), 2.55-2.88 (m, 4H), 1.88-2.18 (m, 2H), 1.47-1.83 (m, 6H).

Step F (−)-(E)-3-[1'-Benzyl-4-oxo-spiro(chromane-2,3'-pyrrolidine)-6-yl]-N-hydroxy acrylamide hydrochloride (31.3 mg) was obtained following the procedure described in Example 2, Step D, starting from 80 mg (0.17 mmol) of the THP protected hydroxamic acid.

Y=44%

Optical rotation: $\alpha_D$=−4.4°, c=0.27 g/100 ml in MeOH

LC-MS: Method F, rt=1.22; (ES+) MH$^+$: 379

$^1$H NMR (DMSO-d$_6$) δ (ppm): 7.92 (d, J=2.35 Hz, 1H), 7.80 (dd, J=8.36, 2.49 Hz, 1H), 7.34-7.61 (m, 6H), 7.12 (d, J=8.22 Hz, 1H), 6.51 (d, J=16.14 Hz, 1H), 4.34 (bs, 2H), 3.11-3.53 (m, 6H), 2.29-2.44 (m, 2H).

Example 4

(+)-(E)-3-[1'-Benzyl-4-oxo-spiro(chromane-2,3'-pyrrolidine)-6-yl]-N-hydroxy-acrylamide

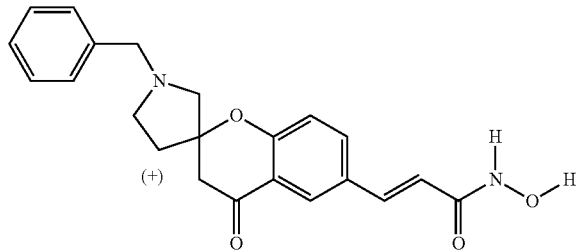 [SMILES: O=C(/C=C/c1ccc2c(c1)C(=O)CC1(CCN(Cc3ccccc3)C1)O2)NO]

Step A (−)-(E)-3-[1'-[(S)-2-(6-Methoxynaphthalen-2-yl)propanoyl]-4-oxo-spiro(chromane-2,3'-pyrrolidine)-6-yl]-acrylic acid methyl ester (630 mg) was obtained as a white solid as described in the procedure for Example 3, Step A.
Y=19%
LC-MS: (ES+) MH$^+$: 500
Optical rotation: $\alpha_D$=−14.58°, c=0.93 g/100 ml in DCM
$^1$H NMR (CDCl$_3$) δ (ppm): 7.32-8.17 (m, 5H), 6.94-7.23 (m, 3H), 6.77 (dd, J=8.80, 2.35 Hz, 1H), 6.40 and 6.21 (d, J=15.85 Hz, 1H), 6.12 (d, J=8.80 Hz, 1H), 4.00-4.21 (m, 1H), 3.94 (s, 3H), 3.85 (s, 3H), 3.67-3.84 (m, 2H), 3.29-3.63 (m, 2H), 2.97 (d, J=16.73 Hz, 1H), 2.69 (d, J=16.73 Hz, 1H), 2.20-2.46 (m, 1H), 1.70-2.12 (m, 1H), 1.45 (d, J=7.04 Hz, 3H).
Step B HCl 20% aq. (5 ml) was added to a suspension of (−)-(E)-3-[1'-[(S)-2-(6-methoxynaphthalen-2-yl)propanoyl]-4-oxo-spiro(chromane-2,3'-pyrrolidine)-6-yl]-acrylic acid methyl ester (600 mg, 1.20 mmol) in glacial AcOH (5 ml). The mixture was treated following the procedure used for Example 3, Step B to give (−)-(E)-3-[4-oxo-spiro(chromane-2,3'-pyrrolidine)-6-yl]-acrylic acid methyl ester (120 mg) as a white solid (free base).
Y=34.8%
LC-MS: (ES+) MH$^+$: 288
Optical rotation: $\alpha_D$=−1.077°, c=0.26 g/100 ml in DCM
$^1$H NMR (DMSO-d$_6$) δ (ppm): 7.99 (d, J=2.05 Hz, 1H), 7.96 (dd, J=8.51, 2.35 Hz, 1H), 7.67 (d, J=16.14 Hz, 1H), 7.06 (d, J=8.51 Hz, 1H), 6.56 (d, J=16.14 Hz, 1H), 3.72 (s, 3H), 2.74-3.10 (m, 6H), 1.88-2.10 (m, 1H), 1.65-1.85 (m, 1H).
Step C (−)-(E)-3-[4-Oxo-spiro(chromane-2,3'-pyrrolidine)-6-yl]-acrylic acid methyl ester (110 mg, 0.38 mmol) was treated with benzaldehyde and NaBH(OAc)$_3$ according to the procedure used for Example 2, Step A to give (+)-(E)-3-[1'benzyl-4-oxo-spiro(chromane-2,3'-pyrrolidine)-6-yl]-acrylic acid methyl ester (45 mg).
Y=31.4%
LC-MS: (ES+) MH$^+$: 378
Optical rotation: $\alpha_D$=−0.72°, c=0.25 g/100 ml in DCM
$^1$H NMR (DMSO-d$_6$) δ (ppm): 7.97 (d, J=2.35 Hz, 1H), 7.97 (dd, J=9.10, 2.35 Hz, 1H), 7.66 (d, J=16.14 Hz, 1H), 7.18-7.39 (m, 5H), 7.10 (d, J=9.10 Hz, 1H), 6.56 (d, J=15.85 Hz, 1H), 3.72 (s, 3H), 3.61 (s, 2H), 3.01 (d, J=16.43 Hz, 1H), 2.95 (d, J=16.73 Hz, 1H), 2.84 (d, J=10.56 Hz, 1H), 2.69-2.80 (m, 1H), 2.60 (d, J=10.56 Hz, 1H), 2.56-2.64 (m, 1H), 1.88-2.17 (m, 2H).

Step D (+)-(E)-3-[1'Benzyl-4-oxo-spiro(chromane-2,3'-pyrrolidine)-6-yl]-acrylic acid methyl ester (40 mg, 0.106 mmol) was hydrolyzed in aqueous 20% HCl solution and AcOH following the procedure described in Example 1, Step A, giving (+)-(E)-3-[1'-benzyl-4-oxo-spiro(chromane-2,3'-pyrrolidine)-6-yl]-acrylic acid (33 mg) as a white solid (hydrochloride salt).
Y=78%
LC-MS: (ES+) MH$^+$: 364
Optical rotation: $\alpha_D$=+10.08°, c=0.25 g/100 ml in MeOH
$^1$H NMR (DMSO-d$_6$) δ (ppm): 11.01-11.75 (m, 1H), 7.91-8.12 (m, 2H), 7.53-7.71 (m, 3H), 7.37-7.53 (m, 3H), 6.95-7.26 (m, 1H), 6.30-6.57 (m, 1H), 4.29-4.58 (m, 2H), 2.91-3.67 (m, 6H), 1.98-2.45 (m, 2H).
Step E (+)-(E)-3-[1'-Benzyl-4-oxo-spiro(chromane-2,3'-pyrrolidine)-6-yl]-acrylic acid hydrochloride salt (33 mg, 0.083 mmol) was reacted with NH$_2$OTHP following the procedure described in Example 1, Step C, giving (E)-3-[1'-benzyl-4-oxo-spiro(chromane-2,3'-pyrrolidine)-6-yl]-N-(tetrahydropyran-2-yloxy)-acrylamide (24 mg) as a light yellow solid.
Y=63%
LC-MS: (ES+) MH$^+$: 463
$^1$H NMR (DMSO-d$_6$) δ (ppm): 11.11 (bs, 1H), 7.89 (d, J=2.05 Hz, 1H), 7.70-7.86 (m, 1H), 7.46 (d, J=15.85 Hz, 1H), 7.18-7.37 (m, 5H), 7.10 (d, J=8.51 Hz, 1H), 6.46 (d, J=16.14 Hz, 1H), 4.90 (bs, 1H), 3.85-4.09 (m, 1H), 3.61 (s, 2H), 3.46-3.59 (m, 1H), 2.98 (s, 2H), 2.84 (d, J=10.56 Hz, 1H), 2.70-2.78 (m, 1H), 2.60 (d, J=10.27 Hz, 1H), 2.56-2.66 (m, 1H), 1.89-2.18 (m, 2H), 1.36-1.79 (m, 6H).
Step F (+)-(E)-3-[1'-Benzyl-4-oxo-spiro(chromane-2,3'-pyrrolidine)-6-yl]-N-hydroxy acrylamide (15.8 mg) was obtained as its hydrochloride salt following the procedure described in Example 2, Step D, starting from 24 mg (0.052 mmol) of the THP protected hydroxamic acid.
Y=75%
Optical rotation: $\alpha_D$=+10.27°, c=0.255 g/100 ml in MeOH
LC-MS: Method C, rt=3.05; (ES+) MH$^+$: 379
$^1$H NMR (DMSO-d$_6$) δ (ppm): 10.75-11.20 (m, 1H), 10.69 (s, 1H), 9.02 (bs, 1H), 7.92 (s, 1H), 7.76-7.87 (m, 1H), 7.36-7.68 (m, 6H), 6.98-7.28 (m, 1H), 6.44 (d, J=15.26 Hz, 1H), 4.24-4.63 (m, 2H), 3.37-3.84 (m, 4H), 2.94-3.22 (m, 2H), 1.99-2.34 (m, 2H).

Example 5

(±)-(E)-3-[1'Acetyl-4-oxo-spiro(chromane-2,3'-pyrrolidine)-6-yl]-N-hydroxy-acrylamide

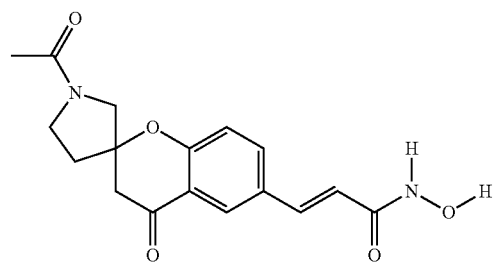 [SMILES: CC(=O)N1CCC2(CC(=O)c3cc(/C=C/C(=O)NO)ccc3O2)C1]

Step A

A suspension of (±)-(E)-3-[4-oxo-spiro(chromane-2,3'-pyrrolidine)-6-yl]-acrylic acid methyl ester hydrochloride salt (400 mg, 1.23 mmol, Intermediate 1) in DCM (15 ml) was treated with acetyl chloride (0.105 ml, 1.49 mmol) and DIPEA (0.264 ml, 1.49 mmol) and stirred at RT for 1 h. The solution was then evaporated under vacuum and the crude product was purified by chromatography column (eluent: DCM/MeOH 95:5) to give (±)-(E)-3-[1-acetyl-4-oxo-spiro (chromane-2,3'-pyrrolidine)-6-yl]-acrylic acid methyl ester as a white solid (240 mg).

Y=59%

LC-MS: (ES+) MH$^+$: 330

$^1$H NMR (CDCl$_3$) δ (ppm): 8.06 (d, J=1.76 Hz, 1H), 7.65-7.78 (m, 1H), 7.65 (d, J=16.14 Hz, 1H), 7.00 (d, J=8.51 Hz, 1H), 6.40 (d, J=16.14 Hz, 1H), 3.82 (s, 3 H), 3.34-4.13 (m, 4H), 2.82-3.12 (m, 2H), 2.29-2.57 (m, 1H), 2.11 (s, 3H), 1.87-2.09 (m, 1H).

Step B (±)-(E)-3-[1'-Acetyl-4-oxo-spiro(chromane-2,3'-pyrrolidine)-6-yl]-acrylic acid methyl ester (240 mg, 0.73 mmol) was hydrolyzed with HCl and AcOH following the procedure described in Example 1, Step A, giving (±)-(E)-3-[1'acetyl-4-oxo-spiro(chromane-2,3'-pyrrolidine)-6-yl]-acrylic acid as a white solid (135.5 mg, 0.43 mmol, 59%). The acid was treated with NH$_2$OTHP according to the procedure described in Example 1, Step C, giving (E)-3-[1'-acetyl-4-oxo-spiro (chromane-2,3'-pyrrolidine)-6-yl]-N-(tetrahydro-pyran-2-yloxy)-acrylamide as a light yellow solid (82 mg, 0.20 mmol, 46%). Finally, removal of THP protecting group following the procedure described in Example 2, Step D gave (±)-(E)-3-[1'-acetyl-4-oxo-spiro(chromane-2,3'-pyrrolidine)-6-yl]-N-hydroxy-acrylamide (64.2 mg, 97%) as a red solid.

Y=27% (over 3 steps)

LC-MS: Method B, rt=1.02; (ES+) MH$^+$: 331

$^1$H NMR (DMSO-d$_6$) δ (ppm): 7.83-8.04 (m, 1H), 7.69-7.83 (m, 1H), 7.43 (d, J=17.02 Hz, 1H), 6.88-7.18 (m, 1H), 6.43 (d, J=15.26 Hz, 1H), 3.72-4.03 (m, 3 H), 3.27-3.44 (m, 1H), 3.14 (d, J=16.73 Hz, 1H), 2.85-3.05 (m, 1H), 2.03-2.37 (m, 2H), 1.93 (s, 3H).

Example 6

(±)-(E)-3-[1-Benzoyl-4-oxo-spiro(chromane-2,3'-pyrrolidine)-6-yl]-N-hydroxy-acrylamide

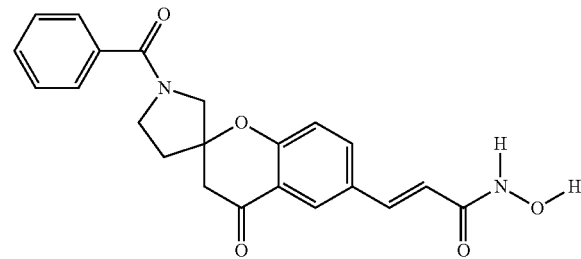 [SMILES: O=C(/C=C/c1ccc2c(c1)C(=O)CC1(CCN(C(=O)c3ccccc3)C1)O2)NO]

(±)-(E)-3-[1'-Benzoyl-4-oxo-spiro(chromane-2,3'-pyrrolidine)-6-yl]-acrylic acid methyl ester was obtained starting from Intermediate 1 (124 mg, 0.383 mmol), benzoyl chloride (44.3 μl, 0.383 mmol) and DIPEA (13.6 μl, 0.766 mmol), according to the procedure described in Example 5, Step A giving a white solid (145 mg, 0.37 mmol, 97%). The methyl ester group was hydrolyzed in aqueous HCl (25%) and AcOH following the procedure described in Example 1, Step A, giving (±)-(E)-3-[1'-benzoyl-4-oxo-spiro(chromane-2,3'-pyrrolidine)-6-yl]-acrylic acid as a white solid (111 mg, 0.294 mmol, 79%). The obtained acid (101 mg, 0.268 mmol) was treated with NH$_2$OTHP according to the procedure described in Example 1, Step C, giving (E)-3-[1'-benzoyl-4-oxo-spiro(chromane-2,3'-pyrrolidine)-6-yl]-N-(tetrahydro-pyran-2-yloxy)-acrylamide as a yellow solid (41 mg, 0.086 mmol, 32%). Finally, removal of THP protecting group following the procedure described in Example 1, Step D gave (±)-(E)-3-[1-benzoyl-4-oxo-spiro(chromane-2,3'-pyrrolidine)-6-yl]-N-hydroxy-acrylamide (10 mg, 30%) as a red solid.

Y=7% (over 4 steps)

LC-MS: Method A, rt=3.23 min; (ES+) MH$^+$: 393

$^1$H NMR (MeOD-d$_4$) δ (ppm): 8.00-8.05 (m, 1H), 7.77-7.83 (m, 1H), 7.44-7.59 (m, 6H), 7.11 (d, J=8.4, 1H), 6.44 (d, J=14.3, 1H), 3.65-4.08 (m, 4H), 2.94-3.21 (m, 2H), 2.09-2.45 (m, 2H).

Example 7

(±)-(E)-3-[1'-Methyl-4-oxo-spiro(chromane-2,3'-pyrrolidine)-6-yl]-N-hydroxy-acrylamide

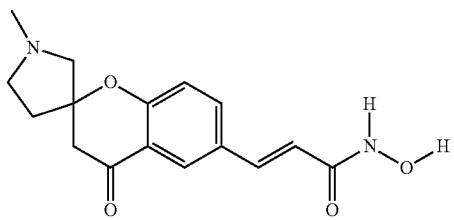 [SMILES: CN1CCC2(CC(=O)c3cc(/C=C/C(=O)NO)ccc3O2)C1]

Step A (±)-(E)-3-[1'-Methyl-4-oxo-spiro(chromane-2,3'-pyrrolidine)-6-yl]-acrylic acid methyl ester was synthesized by treating Intermediate 1 (253 mg, 0.78 mmol), with aqueous 37% formaldehyde solution. (0.069 ml, 0.94 mmol), and NaBH(OAc)$_3$ (252 mg, 1.17 mmol) according to the procedure for preparation of Example 2, Step A, to give the product as yellow solid (111 mg).

Y=47%

LC-MS: (ES+) MH$^+$: 302

$^1$H-NMR (CDCl$_3$) δ (ppm): 8.05 (d, J=2.35 Hz, 1H), 7.67 (dd, J=8.51, 2.35 Hz, 1H), 7.66 (d, J=15.55 Hz, 1H), 7.07 (d, J=8.51 Hz, 1H), 6.40 (d, J=16.14 Hz, 1H), 3.82 (s, 3H), 3.10 (d, J=10.56 Hz, 1H), 2.98 (d, J=16.43 Hz, 1H), 2.91 (d, J=16.43 Hz, 1H), 2.84-3.04 (m, 1H), 2.80 (bs, 2H), 2.50 (bs, 3H), 2.24-2.43 (m, 1H), 1.98-2.22 (m, 1H).

Step B (±)-(E)-3-[1'-Methyl-4-oxo-spiro(chromane-2,3'-pyrrolidine)-6-yl]-acrylic acid methyl ester (105 mg, 0.35 mmol) was hydrolyzed with HCl and AcOH following the procedure described in Example 1, Step A, giving (±)-(E)-3-[1'-methyl-4-oxo-spiro(chromane-2,3'-pyrrolidine)-6-yl]-acrylic acid (110 mg, 0.34 mmol, 98%) as a white solid (hydrochloride salt). The acid was treated with NH$_2$OTHP according to the procedure described in Example 1, Step C, to give (E)-3-[1'-methyl-4-oxo-spiro(chromane-2,3'-pyrrolidine)-6-yl]-N-(tetrahydro-pyran-2-yloxy)-acrylamide (90 mg, 0.23 mmol, 68%). Finally, removal of THP protecting group following the procedure described in Example 2, Step D and purification by preparative HPLC gave (±)-(E)-3-[1'-methyl-4-oxo-spiro(chromane-2,3'-pyrrolidine)-6-yl]-N-hydroxy acrylamide (30.5 mg, 31%) as its trifluoroacetic salt.

Y=21% (over 3 steps)

LC-MS: Method B, rt=1.30; (ES+) MH$^+$: 303

$^1$H NMR (DMSO-d$_6$) δ (ppm): 10.48 (br s, 1H), 10.05 (br s, 1H), 9.02 (br s, 1H), 7.89-7.97 (m, 1H), 7.78-7.89 (m, 1H), 7.46 (d, J=15.85 Hz, 1H), 7.15 (dd, J=15.11, 8.66 Hz, 1H), 6.47 (d, J=16.14 Hz, 1H), 3.62-3.99 (m, 2H), 3.00-3.59 (m, 4H), 2.83 (d, J=4.70 Hz, 3H), 1.99-2.46 (m, 2H).

Example 8

(±)-(E)-3-[1'-Ethyloxycarbonyl-4-oxo-spiro(chromane-2,3'-pyrrolidine)-6-yl]-N-hydroxy-acrylamide

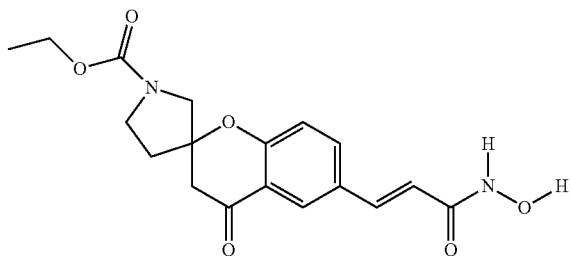 [SMILES: CCOC(=O)N1CCC2(CC(=O)c3cc(/C=C/C(=O)NO)ccc3O2)C1]

(±)-(E)-3-[1'-Ethyloxycarbonyl-4-oxo-spiro[chromane-2,4'-pyrrolidine]-6-yl]-acrylic acid methyl ester was obtained starting from Intermediate 1 (600 mg, 1.86 mmol) and ethyl chloro formate (0.212 ml, 2.23 mmol), according to the procedure described in Example 5, Step A giving a yellow solid (600 mg, 1.67 mmol, 90%). (±)-(E)-3-[1'-Ethyloxycarbonyl-4-oxo-spiro[chromane-2,4'-pyrrolidine]-6-yl]-acrylic acid methyl ester (600 mg, 1.67 mmol) was hydrolyzed using HCl and AcOH following the procedure described in Example 1, Step A, and the acid was purified by column chromatography (eluent DCM/MeOH 95:5) giving 550 mg (95%) of a white solid. The product (350 mg, 1.01 mmol) was treated with NH$_2$OTHP according to the procedure described in Example 1, Step C, giving (E)-3-[1'-ethyloxycarbonyl-4-oxo-spiro[chromane-2,4'-pyrrolidine]-6-yl]-N-(tetrahydro-pyran-2-yloxy)-acrylamide as a yellow solid (370 mg, 0.83 mmol, 82%). Finally, removal of THP protecting group following the procedure described in Example 1, Step D gave (±)-(E)-3-[1'-ethyloxycarbonyl-4-oxo-spiro[chromane-2,4'-pyrrolidine]-6-yl]-N-hydroxy-acrylamide (49 mg, 16%) as a light yellow solid.

Y=11% (over 4 steps)
LC-MS: Method D, rt=3.70; (ES+) MH$^+$: 361
$^1$H NMR (DMSO-d$_6$) δ (ppm): 10.66 (bs, 1H), 7.92 (d, J=2.05 Hz, 1H), 7.78 (dd, J=8.80, 2.05 Hz, 1H), 7.45 (d, J=15.85 Hz, 1H), 7.11 (d, J=8.80 Hz, 1H), 6.43 (d, J=15.85 Hz, 1H), 3.98-4.12 (m, 2H), 3.66 (dd, J=12.03, 1.47 Hz, 1H), 3.48-3.58 (m, 1H), 3.35-3.48 (m, 2H), 3.15 (d, J=16.73 Hz, 1H), 2.90-2.99 (m, 1H), 1.93-2.31 (m, 2H), 1.18 (dt, J=10.78, 7.08 Hz, 3H).

Example 9

(±)-(E)-3-[1'-(2-Phenyl-ethyl)-4-oxo-spiro(chromane-2,3'-pyrrolidine)-6-yl]-N-hydroxy-acrylamide

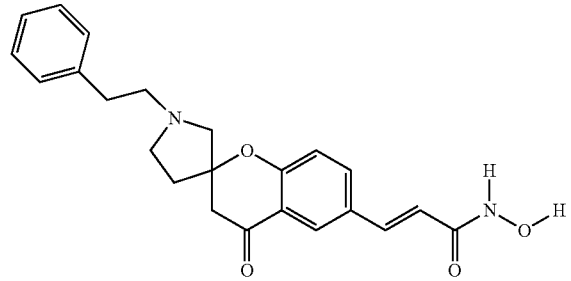 [SMILES: O=C(/C=C/c1ccc2c(c1)C(=O)CC1(CCN(CCc3ccccc3)C1)O2)NO]

Step A

A suspension of (E)-3-[4-oxo-spiro(chromane-2,3'-pyrrolidine)-6-yl]-acrylic acid methyl ester (500 mg, 1.55 mmol, Intermediate 1) in DCM (15 ml) was treated with DIPEA (0.33 ml, 1.86 mmol) and phenethyl bromide (0.251 ml, 1.86 mmol), and stirred at RT for 8 days. The mixture was concentrated and the crude residue was purified by column chromatography (eluent: petroleum ether/EtOAc 7:3) to give (±)-(E)-3-[1'-(2-phenyl-ethyl)-4-oxo-spiro(chromane-2,3'-pyrrolidine)-6-yl]-acrylic acid methyl ester a yellow solid (280 mg).

Y=46%
LC-MS: (ES+) MH$^+$: 392
$^1$H NMR (CDCl$_3$) δ (ppm): 8.05 (d, J=2.35 Hz, 1H), 7.67 (dd, J=8.80, 2.35 Hz, 1H), 7.66 (d, J=15.85 Hz, 1H), 7.12-7.39 (m, 5H), 7.06 (d, J=8.51 Hz, 1H), 6.40 (d, J=16.14 Hz, 1H), 3.82 (s, 3H), 3.09 (d, J=10.27 Hz, 1H), 2.84-3.03 (m, 4H), 2.52-2.84 (m, 5H), 2.18-2.42 (m, 1H), 1.84-2.16 (m, 1H).

Step B (±)-(E)-3-[1'-(2-Phenyl-ethyl)-4-oxo-spiro[chromane-2,4'-pyrrolidine]-6-yl]-acrylic acid methyl ester (280 mg, 0.71 mmol) was hydrolyzed with HCl and AcOH following the procedure described in Example 1, Step A, giving (±)-(E)-3-[1'-(2-phenyl-ethyl)-4-oxo-spiro[chromane-2,4'-pyrrolidine]-6-yl]-acrylic acid as a white solid (288 mg, 98%). The acid was treated with NH$_2$OTHP according to the procedure described in Example 1, Step C, giving (E)-3-[1'-(2-phenyl-ethyl)-4-oxo-spiro[chromane-2,4'-pyrrolidine]-6-yl]-N-(tetrahydro-pyran-2-yloxy)-acrylamide as a yellow solid (103 mg, 0.22 mmol, 31%). Finally, removal of THP protecting group following the procedure described in Example 1, Step D gave (±)-(E)-3-[1'-(2-phenyl-ethyl)-4-oxo-spiro[chromane-2,4'-pyrrolidine]-6-yl]-N-hydroxy-acrylamide hydrochloride (33.7 mg, 36%) as a white solid.

Y=11% (over 3 steps)
LC-MS: Method B, rt=1.25; (ES+) MH$^+$: 393
$^1$H NMR (DMSO-d$_6$+Na$_2$CO$_3$) δ (ppm): 7.83 (d, J=2.05 Hz, 1H), 7.74 (dd, J=8.51, 2.05 Hz, 1H), 7.12-7.38 (m, 6H), 7.05 (d, J=8.80 Hz, 1H), 6.39 (d, J=15.85 Hz, 1H), 2.95 (s, 2H), 2.87-3.03 (m, 1H), 2.76-2.87 (m, 1H), 2.54-2.76 (m, 6H), 2.02-2.15 (m, 1H), 1.85-2.01 (m, 1H).

Example 10

(±)-(E)-3-[1'(1-Methyl-1H-indol-3-ylmethyl)-4-oxo-spiro(chromane-2,3'-pyrrolidine)-6-yl]-N-hydroxy-acrylamide

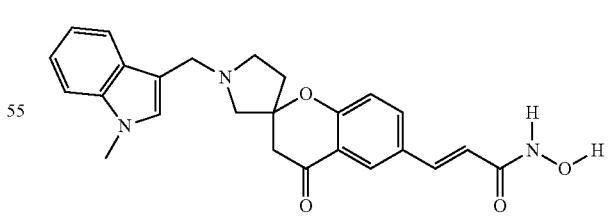

A suspension of (±)-(E)-3-[4-oxo-spiro(chromane-2,3'-pyrrolidine)-6-yl]acrylic acid methyl ester (284 mg, 0.88 mmol, Intermediate 1) in 1 M Na$_2$CO$_3$, was stirred for 10 min, then extracted with DCM and treated with N-methyl-indol-3-carbaldehyde (167 mg, 1.06 mmol) and NaBH(OAc)$_3$ (297 mg, 1.32 mmol) following the procedure described in Example 2, step A, giving (±)-(E)-3-[1'(1-methyl-1H-indol- 3-ylmethyl)-4-oxo-spiro(chromane-2,3'-pyrrolidine)-6-yl]-acrylic acid methyl ester (191 mg, 0.44 mmol, 42%) as a white solid. The resulting ester was hydrolyzed as described in Example 2, step B, giving (±)-(E)-3-[1'(1-methyl-1H-indol-3-ylmethyl)-4-oxo-spiro(chromane-2,3'-pyrrolidine)-6-yl]-acrylic acid (51 mg, 0.11 mmol, 25%) as an orange solid (hydrochloride salt). The product was suspended in DCM (3 ml), TEA (0.025 ml, 0.31 mmol) was added, and the clear solution was treated with NH$_2$OTHP following the procedure described in Example 2, step C, giving (E)-3-[1'-(1-methyl-1H-indol-3-ylmethyl)-4-oxo-spiro(chromane-2,3'-pyrrolidine)-6-yl]-N-(tetrahydro-pyran-2-yloxy)-acrylamide (53 mg, 0.10 mmol, 91%) as a light yellow solid. The compound was then dissolved in DCM (3 ml) and treated with 1 M HCl in diethyl ether (3 ml) as described in Example 2, step D, giving a light brown solid after aqueous workup and column chromatography (eluent: DCM/MeOH 9:1) (10 mg, 22%, free base)

Y=3% over 4 steps.

LC-MS: Method G, rt=2.23 min; (ES+) MH$^+$: 432

$^1$H NMR (300 MHz, DMSO-d$_6$) δ (ppm): 10.65 (br. s, 1H), 8.99 (br. s, 1H), 7.86 (d, J=2.05 Hz, 1H), 7.74 (dd, J=8.66, 2.20 Hz, 1H), 7.63 (d, J=7.63 Hz, 1H), 7.32-7.47 (m, 2H), 7.22 (s, 1H), 7.10-7.18 (m, 1H), 6.94-7.10 (m, 2H), 6.40 (d, J=15.55 Hz, 1H), 3.78 (br. s, 2H), 3.74 (s, 3H), 2.95 (s, 2H), 2.55-2.94 (m, 4H), 1.84-2.18 (m, 2H).

Example 11

(±)-(E)-3-[1'-(4-Fluoro-benzyl)-4-oxo-spiro(chromane-2,3'-pyrrolidine)-6-yl]-N-hydroxy-acrylamide

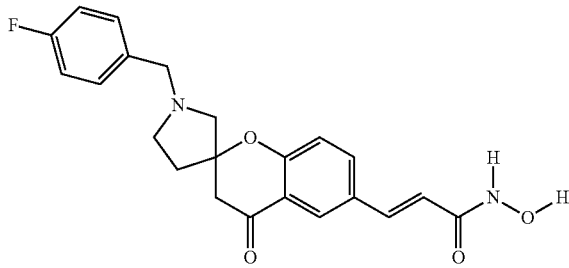 [SMILES: O=C(/C=C/c1ccc2c(c1)C(=O)CC1(CCN(Cc3ccc(F)cc3)C1)O2)NO]

A suspension of Intermediate 1 (250 mg, 0.77 mmol) in aqueous 10% NaHCO$_3$ solution was extracted with DCM (3×10 ml). The organic phase was dried over Na$_2$SO$_4$ and evaporated. The resulting solid was dissolved in DCM (10 ml), treated with 4-fluoro-benzaldehyde (0.090 ml, 0.85 mmol) and NaBH(OAc)$_3$ (245 mg, 1.15 mmol) as described in Example 2, Step A, to give (±)-(E)-3-[1'-(4-fluoro-benzyl)-4-oxo-spiro(chromane-2,3'-pyrrolidine)-6-yl]-acrylic acid methyl ester (300 mg, 0.76 mmol, 99%) as a light brown solid.

This ester was hydrolyzed with aqueous 20% HCl solution and AcOH following the procedure described in Example 1, Step A, giving (±)-(E)-3-[1'-(4-fluoro-benzyl)-4-oxo-spiro (chromane-2,3'-pyrrolidine)-6-yl]-acrylic acid (305 mg, 0.73 mmol, 96%) as a light brown solid (hydrochloride salt). This was treated with NH$_2$OTHP following the procedure described in Example 1, Step C, giving (±)-(E)-3-[1'-benzyl-4-oxo-spiro(chromane-2,3'-pyrrolidine)-6-yl]-N-(tetrahydro-pyran-2-yloxy)-acrylamide (288 mg, 0.60 mmol, 82%) as a light yellow solid. This was treated with HCl in diethyl ether as described in example 3, Step D, giving (±)-(E)-3-[1'-(4-fluoro-benzyl)-4-oxo-spiro(chromane-2,3'-pyrrolidine)-6-yl]-N-hydroxy-acrylamide (188 mg, 0.43 mmol, 74%) as a light pink solid (hydrochloride salt).

Y: 56% (over 4 steps).

LC-MS: Method F, rt=1.26; (ES+) MH$^+$: 397

$^1$H NMR (DMSO-d$_6$+Na$_2$CO$_3$) δ (ppm): 7.82 (s, 1H), 7.73 (dd, J=8.51, 2.05 Hz, 1H), 7.22-7.39 (m, 3H), 7.12 (m, 2H), 7.06 (d, J=8.51 Hz, 1H), 6.40 (d, J=15.85 Hz, 1H), 3.59 (s, 2H), 2.99 (d, J=16.43 Hz, 1H), 2.93 (d, J=17.02 Hz, 1H), 2.68-2.87 (m, 2H), 2.54-2.66 (m, 2H), 1.80-2.20 (m, 2H).

Example 12

(±)-(E)-3-[4-oxo-spiro(chromane-2,3'-piperidine)-6-yl]-N-hydroxy-acrylamide

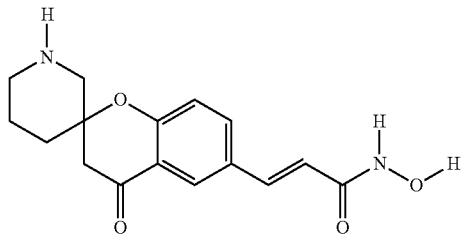 [SMILES: O=C(/C=C/c1ccc2c(c1)C(=O)CC1(CCCNC1)O2)NO]

Step A (±)-(E)-3-[1'-tert-butoxycarbonyl-4-oxo-spiro(chromane-2,3'-piperidine)-6-yl]-acrylic acid methyl ester (Intermediate 2, Step B) (500 mg, 1.25 mmol) was suspended in a dioxane/water 1:1 mixture (20 ml) and 1 M NaOH (1.62 ml) was added. The solution was stirred at RT overnight. After acidification with an aqueous solution containing 5% citric acid the product was collected by filtration and dried under vacuum (±)-(E)-3-[1'-tert-butoxycarbonyl-4-oxo-spiro(chromane-2,3'-piperidine)-6-yl]-acrylic acid (490 mg) as a white solid.

Y=quantitative

LC-MS: (ES+) MH$^+$: 388

$^1$H NMR (DMSO-d$_6$) δ (ppm): 12.30 (bs, 1H), 7.80-8.05 (m, 2H), 7.59 (d, J=15.85 Hz, 1H), 6.83-7.11 (m, 1H), 6.44 (d, J=16.14 Hz, 1H), 3.69-4.02 (m, 2H), 3.02-3.16 (m, 1H), 2.68-3.00 (m, 3H), 1.92-2.15 (m, 1H), 1.58-1.90 (m, 2H), 0.90-1.59 (m, 10H).

Step B

TEA (0.259 ml, 1.86 mmol) was added to solution of (±)-(E)-3-[1'-tert-butoxycarbonyl-4-oxo-spiro(chromane-2,3'-piperidine)-6-yl]-acrylic acid (481 mg, 1.24 mmol) in DCM (15 ml). The mixture was cooled down to 0° C., and EDC (356 mg, 1.86 mmol) and HOBt (251 mg, 1.86 mmol) were added. The mixture was stirred at 0° C. for 2 h, then NH$_2$OTHP (174 mg, 1.49 mmol) was added and the mixture was stirred at RT overnight. The solution was washed with aqueous 5% NaHCO$_3$ solution and brine. The organic layer was then dried over Na$_2$SO$_4$ and evaporated. The crude residue was purified by column chromatography (eluent: DCM/MeOH 98:2) to give (E)-3-[1'-tert-butoxycarbonyl-4-oxo-spiro(chromane-2,3'-piperidine)-6-yl]-N-(tetrahydro-pyran-2-yloxy)-acrylamide (410 mg).

Y=68%

LC-MS: (ES+) MH$^+$: 487

$^1$H NMR (DMSO-d$_6$) δ (ppm): 11.11 (bs, 1H), 7.92 (d, J=2.05 Hz, 1H), 7.70-7.87 (m, 1H), 7.48 (d, J=15.85 Hz, 1H), 6.87-7.14 (m, 1H), 6.48 (d, J=15.85 Hz, 1H), 4.91 (bs, 1 μl), 3.87-4.11 (m, 2H), 3.66-3.87 (m, 1H), 3.38-3.66 (m, 1H), 2.62-3.18 (m, 2H), 1.89-2.15 (m, 1H), 1.26-1.88 (m, 11H), 1.14 (bs, 9H).

Step C

1 M HCl in ether (5 ml, 5 mmol) was added dropwise to a solution of (E)-3-[1'-tert-butoxycarbonyl-4-oxo-spiro(chromane-2,3'-piperidine)-6-yl]-N-(tetrahydro-pyran-2-yloxy)-acrylamide (400 mg, 0.82 mmol) in DCM (5 ml). The mixture was stirred at RT for 1 h. The precipitate was filtered off, washed with DCM, dried under vacuum and collected (98.8 mg) as a white solid (hydrochloride salt).

Y=36%

LC-MS: Method B, rt=0.87; (ES+) MH+: 303

$^1$H NMR (DMSO-$d_6$) δ (ppm): 10.22 (s, 1H), 9.33-9.64 (m, 1H), 8.66-8.80 (m, 1 H), 7.92 (d, J=2.05 Hz, 1H), 7.84 (dd, J=8.66, 1.61 Hz, 1H), 7.45 (d, J=15.85 Hz, 1H), 7.15 (d, J=8.51 Hz, 1H), 6.45 (d, J=15.85 Hz, 1H), 3.44-3.62 (m, 1H), 3.10-3.33 (m, 2H), 3.01 (d, J=17.02 Hz, 1H), 2.85 (d, J=17.02 Hz, 1H), 2.76-2.94 (m, 1H), 1.99-2.16 (m, 1H), 1.63-1.96 (m, 3H).

Example 13

(±)-(E)-3-[1'Benzyl-4-oxo-spiro(chromane-2,3'-piperidine)-6-yl]-N-hydroxy-acrylamide

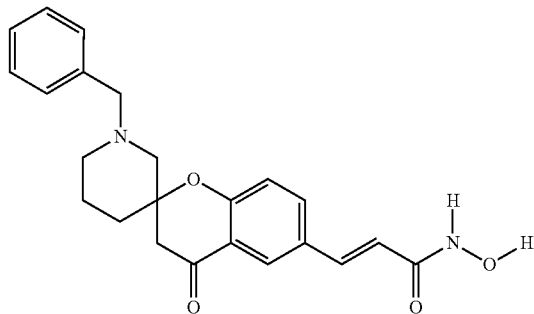 [SMILES: O=C(/C=C/c1ccc2c(c1)C(=O)CC1(CCCN(Cc3ccccc3)C1)O2)NO]

Step A

A suspension of Intermediate 2 (400 mg, 1.19 mmol) in NaHCO$_3$ (10% aqueous solution) was extracted 3 times with DCM (10 ml). The organic phase was dried over Na$_2$SO$_4$ and evaporated. The resulting oil was dissolved in DCM (10 ml), treated with benzaldehyde (0.145 ml, 1.42 mmol) and NaBH(OAc)$_3$ (383 mg, 1.78 mmol), and the resulting clear solution was stirred at RT for 2 h. Water was added to the mixture and the pH was adjusted to a basic value with NH$_3$. The mixture was extracted 3 times with DCM (10 ml). The organic layer was dried, evaporated, and the crude residue was purified by column chromatography (eluent: DCM:MeOH 98:2) to give (±)-(E)-3-[1'-benzyl-4-oxo-spiro(chromane-2,3'-piperidine)-6-yl]-acrylic acid methyl ester (300 mg) as a light yellow solid.

Y=64.5%

LC-MS: (ES+) MH+: 392

$^1$H NMR (CDCl$_3$) δ (ppm): 7.98 (d, J=2.35 Hz, 1H), 7.66 (dd, J=8.51, 2.35 Hz, 1H), 7.64 (d, J=16.14 Hz, 1H), 7.15-7.28 (m, 5H), 7.04 (d, J=8.51 Hz, 1H), 6.38 (d, J=15.85 Hz, 1H), 3.82 (s, 3H), 3.54 (bs, 2H), 2.94 (d, J=17.02 Hz, 1H), 2.87 (d, J=16.73 Hz, 1H), 2.57 (bs, 2H), 2.30-2.52 (m, 2H), 1.61-2.01 (m, 4H).

Step B (±)-(E)-3-[1'-Benzyl-4-oxo-spiro(chromane-2,3'-piperidine)-6-yl]-acrylic acid methyl ester (300 mg, 0.767 mmol) was hydrolyzed with aqueous 20% HCl solution and AcOH following the procedure described in Example 1, Step A, giving (±)-(E)-3-[1'-benzyl-4-oxo-spiro(chromane-2,3'-piperidine)-6-yl]-acrylic acid (250 mg) as a white solid (hydrochloride salt).

Y=79%

LC-MS: (ES+) MH+: 378

$^1$H NMR (DMSO-$d_6$) δ (ppm): 10.65 (bs, 1H), 8.02 (dd, J=8.66, 2.20 Hz, 1H), 7.91 (d, J=2.05 Hz, 1H), 7.60-7.68 (m, 2H), 7.59 (d, J=16.14 Hz, 1H), 7.37-7.52 (m, 3H), 7.32 (d, J=8.51 Hz, 1H), 6.47 (d, J=15.85 Hz, 1H), 4.44 (dd, J=12.62, 2.64 Hz, 1H), 4.22 (dd, J=12.91, 5.87 Hz, 1H), 3.37-3.66 (m, 2H), 3.05-3.29 (m, 1H), 2.98 (d, J=17.02 Hz, 1H), 2.85-2.94 (m, 1H), 2.79 (d, J=17.02 Hz, 1H), 1.98-2.25 (m, 2H), 1.71-1.81 (m, 1H), 1.61 (ddd, J=14.09, 13.50, 4.11 Hz, 1H).

Step C (±)-(E)-3-[1'-Benzyl-4-oxo-spiro(chromane-2,3'-piperidine)-6-yl]-acrylic acid (250 mg, 0.604 mmol) was reacted with NH$_2$OTHP following the procedure described in Example 12, Step C, giving (E)-3-[1'-benzyl-4-oxo-spiro(chromane-2,3'-piperidine)-6-yl]-N-(tetrahydro-pyran-2-yloxy)-acrylamide (270 mg) as a light yellow solid.

Y=94%

LC-MS: (ES+) MH+: 477

$^1$H NMR (DMSO-$d_6$) δ (ppm): 11.10 (bs, 1H), 7.83 (d, J=2.05 Hz, 1H), 7.79 (d, J=8.80 Hz, 1H), 7.46 (d, J=15.55 Hz, 1H), 7.14-7.31 (m, 5H), 7.10 (d, J=8.51 Hz, 1H), 6.45 (d, J=15.85 Hz, 1H), 4.84-4.99 (m, 1H), 3.95 (bs, 1H), 3.51-3.63 (m, 1H), 3.53 (d, J=13.79 Hz, 1H), 3.45 (d, J=13.79 Hz, 1H), 2.96 (d, J=16.73 Hz, 1H), 2.89 (d, J=17.02 Hz, 1H), 2.34-2.47 (m, 4H), 1.27-1.90 (m, 10H).

Step D

1 M HCl in Et$_2$O (5 ml, 5 mmol) was added dropwise to a solution of (E)-3-[1'-benzyl-4-oxo-spiro(chromane-2,3'-piperidine)-6-yl]-N-(tetrahydro-pyran-2-yloxy)-acrylamide (260 mg, 0.55 mmol) in DCM (3 ml). After 1 h a white solid precipitated, which was filtered, washed with DCM, dried under vacuum and purified by preparative HPLC to give 180 mg of (±)-(E)-3-[1'-benzyl-4-oxo-spiro(chromane-2,3'-piperidine)-6-yl]-N-hydroxy-acrylamide as its trifluoroacetic salt.

Y=65%

LC-MS: Method B, rt=1.11; (ES+) MH+: 393

$^1$H NMR (DMSO-$d_6$) δ (ppm): 10.69 (bs, 1H), 9.76 (bs, 1H), 7.89 (s, 1H), 7.84 (d, J=8.80 Hz, 1H), 7.32-7.65 (m, 6H), 7.14 (d, J=8.51 Hz, 1H), 6.43 (d, J=15.85 Hz, 1H), 4.19-4.50 (m, 2H), 3.46-3.69 (m, 2H), 3.11-3.31 (m, 1H), 3.01 (d, J=16.73 Hz, 1H), 2.85-3.00 (m, 1H), 2.80 (d, J=16.73 Hz, 1H), 2.02 (bs, 1H), 1.77-1.97 (m, 2H), 1.53-1.76 (m, 1H).

Example 14

(±)-(E)-3-[1'-Methyl-4-oxo-spiro(chromane-2,3'-piperidine)-6-yl]-N-hydroxy-acrylamide

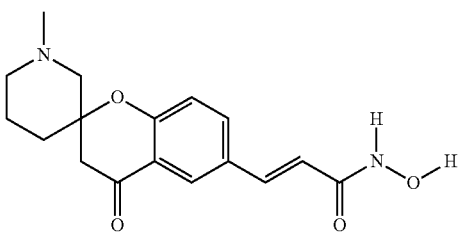 [SMILES: CN1CCCC2(CC(=O)c3cc(/C=C/C(=O)NO)ccc3O2)C1]

Step A (±)-(E)-3-[1'-Methyl-4-oxo-spiro(chromane-2,3'-piperidine)-6-yl]-acrylic acid methyl ester was synthesized starting from Intermediate 2 (800 mg, 2.37 mmol), according to the procedure for preparation of Example 13, Step A, using aqueous 37% formaldehyde solution (0.212 ml, 2.85 mmol), and NaBH(OAc)$_3$ (754 mg, 3.55 mmol) giving (±)-(E)-3-[1'-methyl-4-oxo-spiro(chromane-2,3'-piperidine)-6-yl]-acrylic acid methyl ester as yellow solid (720 mg).

Y=96%

LC-MS: (ES+) MH$^+$: 316

$^1$H NMR (DMSO-d$_6$) δ (ppm): 7.97 (d, J=2.35 Hz, 1H), 7.96 (dd, J=9.10, 2.35 Hz, 1H), 7.67 (d, J=16.14 Hz, 1H), 7.07 (d, J=9.39 Hz, 1H), 6.55 (d, J=15.85 Hz, 1H), 3.72 (s, 3H), 2.97 (d, J=16.73 Hz, 1H), 2.84 (d, J=17.02 Hz, 1H), 2.20-2.47 (m, 4H), 2.13 (s, 3H), 1.59-1.88 (m, 3H), 1.37-1.59 (m, 1H).

Step B (±)-(E)-3-[1-Methyl-4-oxo-spiro(chromane-2,3'-piperidine)-6-yl]-acrylic acid methyl ester (500 mg, 1.59 mmol) was hydrolyzed with HCl and AcOH following the procedure described in Example 1, Step A, giving (±)-(E)-3-[1'-methyl-4-oxo-spiro(chromane-2,3'-pyrrolidine)-6-yl]-acrylic acid (505 mg, 94%) as a white solid (hydrochloride salt). The acrylic acid (500 mg, 1.48 mmol) was treated with NH$_2$OTHP according to the procedure described in Example 12, Step C, giving (E)-3-[1'-methyl-4-oxo-spiro(chromane-2,3'-piperidine)-6-yl]-N-(tetrahydro-pyran-2-yloxy)-acrylamide (530 mg, 89.5%). Finally, removal of THP protecting group (520 mg, 1.30 mmol) following the procedure described in Example 13, Step D gave (±)-(E)-3-[1'-methyl-4-oxo-spiro (chromane-2,3'-piperidine)-6-yl]-N-hydroxy acrylamide (399.5 mg, 87%) as its hydrochloride salt.

Y=73% (over 3 steps)

LC-MS: Method E, rt=2.61; (ES+) MH$^+$: 317

$^1$H NMR (DMSO-d$_6$) δ (ppm): 10.28 (bs, 1H), 7.91 (d, J=1.76 Hz, 1H), 7.84 (dd, J=8.66, 1.91 Hz, 1H), 7.45 (d, J=15.85 Hz, 1H), 7.23 (d, J=8.51 Hz, 1H), 6.47 (d, J=15.55 Hz, 1H), 3.65-3.85 (m, 1H), 3.12-3.46 (m, 2H), 2.96 (d, J=17.02 Hz, 1H), 2.87 (d, J=17.02 Hz, 1H), 2.82-2.95 (m, 1H), 2.76 (d, J=4.70 Hz, 3H), 1.89-2.19 (m, 2H), 1.49-1.87 (m, 2H).

Example 15

(±)-(E)-3-[1'-Ethyloxycarbonyl-4-oxo-spiro(chromane-2,3'-piperidine)-6-yl]-N-hydroxy-acrylamide

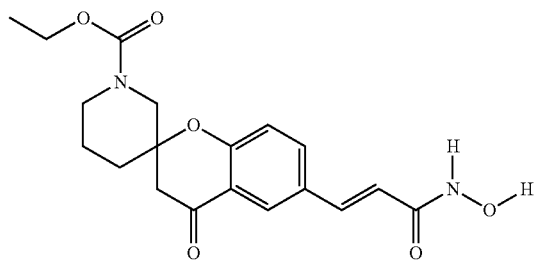 [SMILES: CCOC(=O)N1CCCC2(CC(=O)c3cc(/C=C/C(=O)NO)ccc3O2)C1]

(±)-(E)-3-[1'-Ethyloxycarbonyl-4-oxo-spiro(chromane-2, 3'-piperidine)-6-yl]-acrylic acid methyl ester was obtained starting from Intermediate 2 (350 mg, 1.04 mmol) and ethyl chloro formate (0.118 ml, 1.25 mmol), according to the procedure described in Example 5, Step A, giving a yellow solid (330 mg, 85%). (±)-(E)-3-[1'-Ethyloxycarbonyl-4-oxo-spiro (chromane-2,3'-piperidine)-6-yl]-acrylic acid methyl ester (280 mg, 0.75 mmol) was hydrolyzed using HCl and AcOH following the procedure described in Example 1, Step A, obtaining the acrylic acid as a white solid (220 mg, 82%). The acrylic acid (180 mg, 0.50 mmol) was treated with NH$_2$OTHP according to the procedure described in Example 12, Step C, giving (E)-3-[1'-ethyloxycarbonyl-4-oxo-spiro(chromane-2, 3'-piperidine)-6-yl]-N-(tetrahydro-pyran-2-yloxy)-acrylamide as a yellow solid (150 mg, 0.33 mmol, 65%). Finally, removal of THP protecting group (130 mg) following the procedure described in Example 12, Step D gave (±)-(E)-3-[1-ethyloxycarbonyl-4-oxo-spiro(chromane-2,3'-piperidine)-6-yl]-N-hydroxy-acrylamide (60 mg, 49%) as a light yellow solid.

Y=25.5% (over 4 steps)

LC-MS: Method F, rt=3.11; (ES+) MH$^+$: 375

$^1$H NMR (DMSO-d$_6$ 353K) δ (ppm): 7.89 (d, J=2.35 Hz, 1H), 7.75 (dd, J=8.51, 2.35 Hz, 1H), 7.44 (d, J=15.85 Hz, 1H), 6.99 (d, J=8.51 Hz, 1H), 6.49 (d, J=15.85 Hz, 1H), 3.72-4.13 (m, 4H), 3.06-3.25 (m, 2H), 2.86 (d, J=17.02 Hz, 1H), 2.79 (d, J=17.02 Hz, 1H), 1.94-2.11 (m, 1H), 1.66-1.83 (m, 2H), 1.43-1.63 (m, 1H), 1.05 (t, J=7.19 Hz, 3H).

Example 16

(±)-(E)-3-[1'-Acetyl-4-oxo-spiro(chromane-2,3'-piperidine)-6-yl]-N-hydroxy-acrylamide

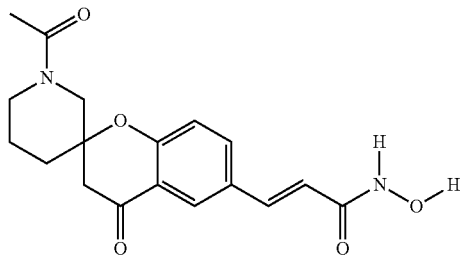 [SMILES: CC(=O)N1CCCC2(CC(=O)c3cc(/C=C/C(=O)NO)ccc3O2)C1]

Step A

Acetyl chloride (168 mg, 2.14 mmol) was added dropwise to a stirred solution of (±)-(E)-3-[4-oxo-spiro(chromane-2,3'-piperidine)-6-yl]-acrylic acid methyl ester (Intermediate 2, 600 mg, 1.78 mmol) and TEA (0.742 ml, 5.33 mmol) in DCM (30 ml). The resulting mixture was stirred overnight at RT, then washed with 5% NaHCO$_3$, brine and dried over Na$_2$SO$_4$. The crude mixture was purified by column chromatography (eluent: DCM/MeOH 99:1) to give (±)-(E)-3-[1'-acetyl-4-oxo-spiro(chromane-2,3'-piperidine)-6-yl]-acrylic acid methyl ester (609 mg).

Y=99%

LC-MS: (ES+) 344

$^1$H NMR (DMSO-d$_6$) δ (ppm): 7.91-8.07 (m, 2H), 7.67 (d, J=15.85 Hz, 1H), 7.02 (d, J=9.39 Hz, 1H), 6.57 (d, J=16.14 Hz, 1H), 4.11-4.28 (m, 1H), 3.72 (s, 3H), 3.52-4.02 (m, 1H), 3.07-3.40 (m, 2H), 2.66-3.02 (m, 2H), 1.38-2.11 (m, 7H).

Step B

A mixture of (±)-(E)-3-[1'-acetyl-4-oxo-spiro(chromane-2,3'-piperidine)-6-yl]-acrylic acid methyl ester (575 mg, 1.68 mmol) and 1 M NaOH (2.18 ml) in dioxane (20 ml) and water (10 ml) was stirred overnight at RT. The mixture was neutralized with 1 M HCl and concentrated under vacuum. The pH was brought to 4 with 1 M HCl and the mixture was extracted with DCM. The organic phase was dried over Na$_2$SO$_4$ and evaporated to dryness. The crude (±)-(E)-3-[1'-acetyl-4-oxo-spiro(chromane-2,3'-piperidine)-6-yl]-acrylic acid was used in the next step without further purification (618 mg)

LC-MS: (ES+) 330

$^1$H NMR (DMSO-d$_6$) δ (ppm): 12.31 (bs, 1H), 7.78-8.06 (m, 2H), 7.59 (d, J=16.14 Hz, 1H), 7.03 (d, J=9.10 Hz, 1H), 6.45 (d, J=16.14 Hz, 1H), 4.07-4.37 (m, 1H), 3.60-4.01 (m, 2H), 3.09-3.42 (m, 1H), 2.94 (d, J=17.02 Hz, 1H), 2.85 (d, J=17.02 Hz, 1H), 1.88-2.17 (m, 1H), 1.78 (s, 3H), 1.29-1.89 (m, 3H).

Step C (±)-(E)-3-[1'-Acetyl-4-oxo-spiro(chromane-2,3'-piperidine)-6-yl]-acrylic acid (crude compound from STEP B, 590 mg) was dissolved in DCM (30 ml) and TEA (0.498 ml, 3.59 mmol). EDC (513 mg, 2.68 mmol) and HOBt (362 mg, 2.68 mmol) were added and the mixture was stirred for 10 min at RT. NH$_2$OTHP (251 mg, 2.15 mmol) was added and the solution was stirred overnight at RT and was then partitioned between 5% NaHCO$_3$ and DCM. The organic layer was washed with brine, dried over Na$_2$SO$_4$ and evaporated to dryness. The crude mixture was purified by column chromatography (eluent: DCM/MeOH 99:1 to 97:3) to give (±)-(E)-3-[1'-acetyl-4-oxo-spiro(chromane-2,3'-piperidine)-6-yl]-N-(tetrahydro-pyran-2-yloxy)-acrylamide that was dissolved in DCM and treated with 4 M HCl in dioxane for 3 h. The precipitate was collected by filtration and washed with DCM to give (±)-(E)-3-[1'-acetyl-4-oxo-spiro(chromane-2,3'-piperidine)-6-yl]-N-hydroxy-acrylamide as pale yellow powder (404 mg).

Y=72% (STEP B and C)

LC-MS: Method H, rt=1.16; (ES+) MH$^+$: 345

$^1$H NMR (DMSO-d$_6$ 353K) δ (ppm): 7.90 (d, J=2.05 Hz, 1H), 7.75 (dd, J=8.51, 2.35 Hz, 1H), 7.43 (d, J=15.85 Hz, 1H), 7.01 (d, J=8.51 Hz, 1H), 6.50 (d, J=15.85 Hz, 1H), 4.01 (bs, 2H), 3.23-3.40 (m, 1H), 3.05 (bs, 1H), 2.88 (m, J=17.31 Hz, 1H), 2.81 (d, J=16.73 Hz, 1H), 1.39-2.21 (m, 7H).

Example 17

(−)-(E)-3-[1'-Benzyl-4-oxo-spiro(chromane-2,3'-piperidine)-6-yl]-N-hydroxy-acrylamide

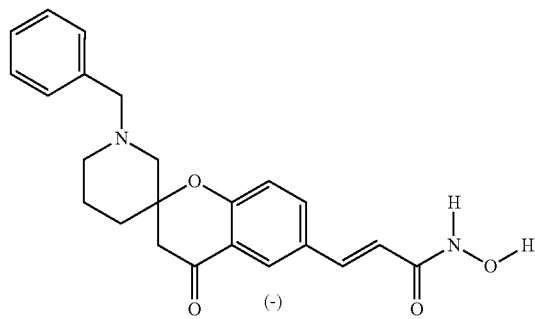 [SMILES: O=C(/C=C/c1ccc2c(c1)C(=O)CC1(CCCN(Cc3ccccc3)C1)O2)NO]

Step A (−)-6-Bromospiro[chroman-2,3'-piperidin]-4-one (Intermediate 7, 798 mg, 2.69 mmol) was dissolved in DCM (30 ml). TEA (0.939 ml, 6.74 mmol) and BOC anhydride (588 mg, 2.69 mmol) were added and the solution was stirred overnight at RT and then washed with 5% citric acid followed by 5% NaHCO$_3$. The organic layer was dried over Na$_2$SO$_4$ and evaporated to dryness. The crude product was purified by column chromatography (eluent: petroleum ether/EtOAc 6:4) to give (+)-6-bromo-4-oxo-spiro[chromane-2,3'-piperidine-6-yl]-1'-carboxylic acid tert-butyl ester (1.00 g)

Y=94%

LC-MS: (ES+) 395

Optical rotation: α$_D$=+20.67°, c=0.505 g/100 ml in MeOH $^1$H NMR (DMSO-d$_6$) δ (ppm): 7.79 (d, J=2.35 Hz, 1H), 7.74 (d, J=8.22 Hz, 1H), 6.67-7.10 (m, 1H), 3.59-3.99 (m, 2H), 2.61-3.18 (m, 4H), 1.90-2.07 (m, 1H), 1.63-1.83 (m, 2H), 1.48-1.55 (m, 1H), 1.47 (s, 9H).

Step B (+)-6-Bromo-4-oxo-spiro[chromane-2,3'-piperidine-6-yl]-1'-carboxylic acid tert-butyl ester (900 mg, 2.27 mmol) was dissolved in DMF (3 ml). Methyl acrylate (587 mg, 6.81 mmol) and TEA (0.950 ml, 6.81 mmol) were added and the mixture was degassed with nitrogen. P(o-tol)$_3$ (27.7 mg, 0.091 mmol) and Pd(OAc)$_2$ (10.2 mg, 0.045 mmol) were added and the mixture was heated at 100° C. under nitrogen for 3 h. Further Pd(OAc)$_2$ (10.2 mg, 0.045 mmol) was added and the solution was heated for additional 5 h and then partitioned between Et$_2$O and water. The aqueous phase was washed with Et$_2$O and the collected organic layer were rinsed with water, dried over Na$_2$SO$_4$ and evaporated to dryness. The crude product was purified by column chromatography (eluent:petroleum ether:EtOAc 9:1 to 7:3) to give (+)-(E)-3-[1'-tert-butoxycarbonyl-4-oxo-spiro(chromane-2,3'-piperidine)-6-yl]-acrylic acid methyl ester (734 mg)

Y=81%

LC-MS: (ES+) 402

Optical rotation: α$_D$=+22.40 c=0.25 g/100 ml in MeOH $^1$H NMR (DMSO-d$_6$) δ (ppm): 7.89-8.09 (m, 2H), 7.68 (d, J=16.14 Hz, 1H), 6.97-7.09 (m, 1H), 6.57 (d, J=16.14 Hz, 1H), 3.75-4.03 (m, 2H), 3.72 (s, 2H), 2.62-3.21 (m, 3H), 2.03 (bs, 1H), 1.65-1.87 (m, 2H), 1.28-1.62 (m, 3H), 1.00-1.26 (m, 9H).

Step C (+)-(E)-3-[1'-Tert-butoxycarbonyl-4-oxo-spiro(chromane-2,3'-piperidine)-6-yl]-acrylic acid methyl ester (710 mg, 1.77 mmol) was dissolved in DCM (50 ml). 4 M HCl in dioxane (2 ml) was added and the mixture was stirred at RT for 3 h. The precipitate was filtered, washed with DCM and dried to give (−)-(E)-3-[4-oxo-spiro(chromane-2,3'-piperidine)-6-yl]-acrylic acid methyl ester hydrochloride (516 mg)

Y=86%

LC-MS: (ES+) 302

Optical rotation: α$_D$=−43.67 c=0.24 g/100 ml in MeOH $^1$H NMR (DMSO-d$_6$) δ (ppm): 9.08 (bs, 2H), 8.05 (dd, J=8.80, 2.35 Hz, 1H), 8.02 (d, J=2.35 Hz, 1H), 7.69 (d, J=16.14 Hz, 1H), 7.15 (d, J=8.51 Hz, 1H), 6.59 (d, J=16.14 Hz, 1H), 3.73 (s, 3H), 3.42-3.56 (m, 1H), 3.13-3.27 (m, 2H), 3.02 (d, J=17.02 Hz, 1H), 2.86 (d, J=16.73 Hz, 1H), 2.78-2.88 (m, 1H), 1.59-2.11 (m, 4H).

Step D (−)-(E)-3-[4-Oxo-spiro(chromane-2,3'-piperidine)-6-yl]-acrylic acid methyl ester hydrochloride (505 mg, 1.49 mmol) was suspended in DCM (50 ml). TEA (0.208 ml, 1.49 mmol) was added and the pH was adjusted to 5 with AcOH. Benzaldehyde (190 mg, 1.794 mmol) and NaBH(OAc)$_3$ (475 mg, 2.24 mmol) were added and the mixture was stirred at RT for 3 h. The resulting solution was washed with 5% NaHCO$_3$ and brine, then dried over Na$_2$SO$_4$ and evaporated to dryness. The crude product was purified by column chromatography (eluent:petroleum ether:EtOAc 9:1 to 7:3) to give (−)-(E)-3-[1'-benzyl-4-oxo-spiro(chromane-2,3'-piperidine)-6-yl]-acrylic acid methyl ester (547 mg).

Y=93%

LC-MS: (ES+) 392

Optical rotation: α$_D$=−29.92 c=0.26 g/100 ml in MeOH $^1$H NMR (DMSO-d$_6$) δ (ppm): 7.98 (dd, J=8.80, 2.35 Hz, 1H), 7.90 (d, J=2.05 Hz, 1H), 7.65 (d, J=16.14 Hz, 1H), 7.14-7.28 (m, 5H), 7.10 (d, J=8.51 Hz, 1H), 6.54 (d, J=16.14 Hz, 1H), 3.72 (s, 3H), 3.53 (d, J=13.79 Hz, 1H), 3.45 (d, J=13.79 Hz, 1H), 2.96 (d, J=16.73 Hz, 1H), 2.89 (d, J=16.73 Hz, 1H), 2.53-2.59 (m, 1H), 2.38-2.46 (m, 3H), 1.65-1.91 (m, 3H), 1.41-1.61 (m, 1H).

Step E (−)-(E)-3-[1'-Benzyl-4-oxo-spiro(chromane-2,3'-piperidine)-6-yl]-acrylic acid methyl ester (525 mg, 1.34 mmol) was hydrolyzed with 1 M NaOH following the experimental procedure described for Example 16 STEP B, to give (−)-(E)-3-[1'-benzyl-4-oxo-spiro(chromane-2,3'-piperidine)-6-yl]-acrylic acid (435 mg).

Y=86%

LC-MS: (ES+) 378

Optical rotation: $\alpha_D$=−18.96 c=0.25 g/100 ml in MeOH $^1$H NMR (DMSO-d$_6$) δ (ppm): 12.29 (s, 1H), 7.94 (dd, J=8.66, 2.20 Hz, 1H), 7.86 (d, J=2.05 Hz, 1H), 7.57 (d, J=16.14 Hz, 1H), 7.15-7.29 (m, 5H), 7.09 (d, J=8.80 Hz, 1H), 6.43 (d, J=15.85 Hz, 1H), 3.53 (d, J=14.09 Hz, 1H), 3.45 (d, J=14.09 Hz, 1H), 2.96 (d, J=16.73 Hz, 1H), 2.89 (d, J=17.02 Hz, 1H), 2.54-2.61 (m, 1H), 2.33-2.46 (m, 3H), 1.69-1.93 (m, 3H), 1.48-1.65 (m, 1H).

Step F (−)-(E)-3-[1'-Benzyl-4-oxo-spiro(chromane-2,3'-piperidine)-6-yl]-acrylic acid (435 mg, 1.15 mmol) was treated with NH$_2$OTHP according to the procedure described in Example 16, Step C, giving the corresponding N-(tetrahydropyran-2-yloxy)-acrylamide and removal of THP protecting group following the procedure described in Example 16, Step C, gave (−)-(E)-3-[1'-benzyl-4-oxo-spiro(chromane-2,3'-piperidine)-6-yl]-N-hydroxy-acrylamide hydrochloride that was triturated in i-PrOH and filtered (81.5 mg).

Y=18%

LC-MS: Method C, rt=3.11; (ES+) MH$^+$: 393

Optical rotation: $\alpha_D$=−12.30 c=1 g/100 ml in MeOH $^1$H NMR (DMSO-d$_6$) δ (ppm): 10.71 (bs, 1H), 10.21 (bs, 1H), 7.78-8.12 (m, 2H), 7.35-7.76 (m, 6H), 7.25 (d, J=8.51 Hz, 1H), 6.44 (d, J=15.55 Hz, 1H), 4.36-4.53 (m, 1H), 4.26 (dd, J=12.91, 5.58 Hz, 1H), 3.46-3.59 (m, 2H), 3.10-3.28 (m, 1H), 2.99 (d, J=17.02 Hz, 1H), 2.86-2.95 (m, 1H), 2.79 (d, J=17.02 Hz, 1H), 1.87-2.18 (m, 2H), 1.71-1.87 (m, 1H), 1.51-1.71 (m, 1H).

Example 18

(+)-(E)-3-[1'-Benzyl-4-oxo-spiro(chromane-2,3'-piperidine)-6-yl]-N-hydroxy-acrylamide

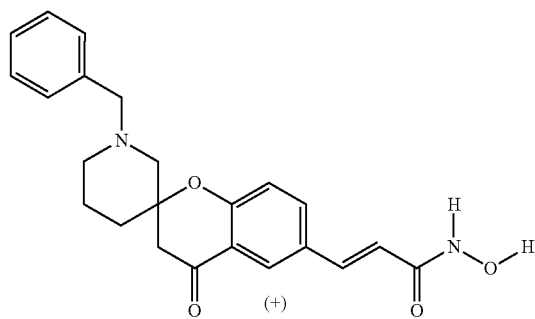 [SMILES: O=C(/C=C/c1ccc2c(c1)C(=O)CC1(CCCN(Cc3ccccc3)C1)O2)NO]

The title compound was obtained as hydrochloride salt starting from (+)-6-bromospiro[chroman-2,3'-piperidin]-4-one (Intermediate 8) following the experimental procedure described for Example 17. The title compound was obtained.

Optical rotation: $\alpha_D$=+9.12, c=1 g/100 ml in MeOH

LC-MS: Method F, rt=1.26; (ES+) MH$^+$: 393

$^1$H NMR (DMSO-d$_6$) δ (ppm): 10.46 (bs, 1H), 10.27 (bs, 1H), 7.80-7.89 (m, 2H), 7.55-7.72 (m, 2H), 7.35-7.54 (m, 4H), 7.29 (d, J=8.80 Hz, 1H), 6.45 (d, J=15.85 Hz, 1H), 4.43 (dd, J=12.76, 2.49 Hz, 1H), 4.24 (dd, J=13.06, 5.72 Hz, 1H), 3.37-3.55 (m, 2H), 3.08-3.23 (m, 1H), 2.98 (d, J=17.02 Hz, 1H), 2.85-2.94 (m, 1H), 2.79 (d, J=17.02 Hz, 1H), 1.92-2.22 (m, 2H), 1.69-1.84 (m, 1H), 1.46-1.69 (m, 1H).

Example 19

(±)-(E)-3-[1'(4-Fluoro-benzyl)-4-oxo-spiro(chromane-2,3'-piperidine)-6-yl]-N-hydroxy-acrylamide

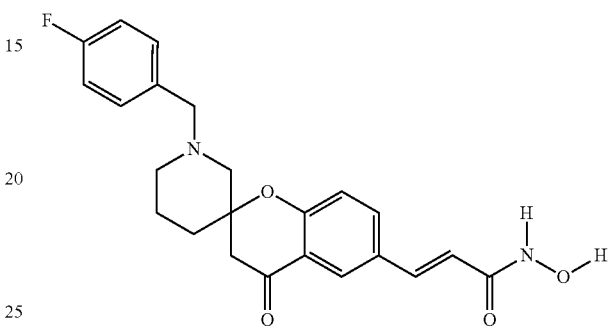

Step A (±)-(E)-3-[4-Oxo-spiro(chromane-2,3'-piperidine)-6-yl]-acrylic acid methyl ester hydrochloride (Intermediate 2, 600 mg, 1.78 mmol) was suspended in DCM (30 ml). TEA (0.248 ml, 1.78 mmol) was added and the pH was adjusted to 5 with AcOH. 4-Fluorobenzaldehyde (265 mg, 2.14 mmol) and NaBH(OAc)$_3$ (566 mg, 2.67 mmol) were added and the resulting mixture was stirred overnight at RT, then washed with 5% NaHCO$_3$, brine and dried over Na$_2$SO$_4$. The crude mixture was purified by column chromatography (eluent: DCM/MeOH 99:1) to give (±)-(E)-3-[1'-(4-fluoro-benzyl)-4-oxo-spiro(chromane-2,3'-piperidine)-6-yl]-acrylic acid methyl ester (660 mg).

Y=90%

LC-MS: (ES+) 410

$^1$H NMR (DMSO-d$_6$) δ (ppm): 7.97 (dd, J=8.51, 2.35 Hz, 1H), 7.91 (d, J=2.35 Hz, 1H), 7.65 (d, J=16.14 Hz, 1H), 7.18-7.32 (m, 2H), 7.09 (d, J=8.51 Hz, 1H), 6.95-7.06 (m, 2H), 6.55 (d, J=16.14 Hz, 1H), 3.72 (s, 3H), 3.50 (d, J=13.79 Hz, 1H), 3.43 (d, J=13.50 Hz, 1H), 2.95 (d, J=16.73 Hz, 1H), 2.89 (d, J=16.73 Hz, 1H), 2.53-2.58 (m, 1H), 2.31-2.46 (m, 3H), 1.65-1.92 (m, 3H), 1.40-1.63 (m, 1H).

Step B (±)-(E)-3-[1'-(4-Fluoro-benzyl)-4-oxo-spiro(chromane-2,3'-piperidine)-6-yl]-acrylic acid methyl ester (630 mg, 1.54 mmol) was treated with 1 M NaOH according to the procedure described in Example 16 STEP B to give (±)-(E)-3-[1'-(4-fluoro-benzyl)-4-oxo-spiro(chromane-2,3'-piperidine)-6-yl]-acrylic acid (516 mg, 85%).

The acid was treated with NH$_2$OTHP according to the procedure described in Example 16, Step C, giving (±)-(E)-3-[1'-(4-fluoro-benzyl)-4-oxo-spiro(chromane-2,3'-piperidine)-6-yl]-N-(tetrahydro-pyran-2-yloxy)-acrylamide as a yellow solid. Removal of the THP protecting group following the procedure described in Example 16, Step C, gave (±)-(E)-3-[1'-(4-fluoro-benzyl)-4-oxo-spiro(chromane-2,3'-piperidine)-6-yl]-N-hydroxy-acrylamide hydrochloride as a white solid (267 mg, 48% over three steps)

LC-MS: Method H, rt=1.17; (ES+) MH$^+$: 411

$^1$H NMR (DMSO-d$_6$) δ (ppm): 10.73 (bs, 1H), 10.50 (bs, 1H), 7.77-7.96 (m, 2H), 7.70 (m, 2H), 7.44 (d, J=15.55 Hz, 1H), 7.10-7.35 (m, 3H), 6.45 (d, J=15.55 Hz, 1H), 4.36-4.62 (m, 1H), 4.26 (dd, J=12.91, 5.58 Hz, 1H), 3.37-3.63 (m, 2H), 3.15 (t, J=11.74 Hz, 1H), 2.99 (d, J=17.02 Hz, 1H), 2.82-2.95 (m, 1H), 2.78 (d, J=17.02 Hz, 1H), 1.87-2.24 (m, 2H), 1.70-1.84 (m, 1H), 1.60 (td, J=13.72, 3.67 Hz, 1H).

Example 20

(±)-(E)-3-[1'-(2-Phenyl-ethyl)-4-oxo-spiro(chromane-2,3'-piperidine)-6-yl]-N-hydroxy-acrylamide

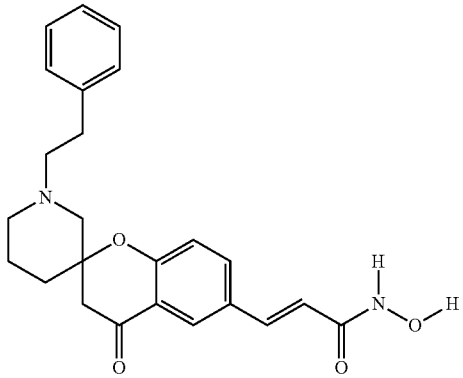 [SMILES: O=C(/C=C/c1ccc2c(c1)C(=O)CC1(CCCN(CCc3ccccc3)C1)O2)NO]

The title compound was obtained starting from (±)-(E)-3-[4-oxo-spiro(chromane-2,3'-piperidine)-6-yl]-acrylic acid methyl ester hydrochloride (Intermediate 2, 600 mg, 1.78 mmol) and phenyl acetaldehyde, following the experimental procedure described for Example 19. The title compound was purified by preparative LC-MS and obtained as its trifluoroacetate salt (67 mg, 7% over four steps)

LC-MS: Method H, rt=1.25; (ES+) MH$^+$: 407

$^1$H NMR (DMSO-d$_6$) δ (ppm): 10.70 (bs, 1H), 9.87 (bs, 1H), 7.94 (d, J=2.05 Hz, 1H), 7.86 (dd, J=8.51, 1.76 Hz, 1H), 7.47 (d, J=15.55 Hz, 1H), 7.17-7.40 (m, 6H), 6.46 (d, J=15.85 Hz, 1H), 3.89 (d, J=13.79 Hz, 1H), 3.53-3.63 (m, 1H), 3.25-3.38 (m, 4H), 2.95-3.15 (m, 3H), 2.87 (d, J=16.73 Hz, 1H), 1.93-2.18 (m, 2H), 1.52-1.88 (m, 2H).

Example 21

(±)-(E)-3-[1'-Benzoyl-4-oxo-spiro(chromane-2,3'-piperidine)-6-yl]-N-hydroxy-acrylamide

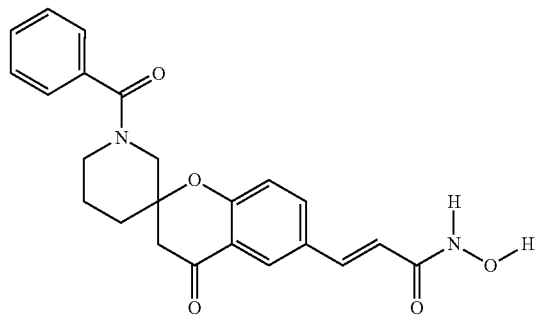 [SMILES: O=C(/C=C/c1ccc2c(c1)C(=O)CC1(CCCN(C(=O)c3ccccc3)C1)O2)NO]

The title compound was obtained starting from (±)-(E)-3-[4-oxo-spiro(chromane-2,3'-piperidine)-6-yl]-acrylic acid methyl ester hydrochloride (Intermediate 2, 600 mg, 1.78 mmol) and benzoyl chloride, following the experimental procedure described for Example 16. The title compound was obtained as pale yellow powder (401 mg, 55% over 4 steps).

LC-MS: Method H, rt=1.52; (ES+) MH$^+$: 407

$^1$H NMR (DMSO-d$_6$ 353K) δ (ppm): 7.82 (d, J=2.05 Hz, 1H), 7.75 (dd, J=8.66, 2.20 Hz, 1H), 7.56 (d, J=15.55 Hz, 1H), 7.24-7.39 (m, 5H), 7.08 (d, J=8.80 Hz, 1H), 6.49 (d, J=15.85 Hz, 1H), 4.08 (d, J=14.08 Hz, 1H), 3.82-4.02 (m, 1H), 3.32 (d, J=13.79 Hz, 1H), 3.00-3.18 (m, 1H), 2.67-2.96 (m, 2H), 2.03-2.21 (m, 1H), 1.70-1.98 (m, 2H), 1.47-1.70 (m, 1H).

Example 22

(±)-(E)-3-[4-oxo-spiro(chromane-2,4'-azepane)-6-yl]-N-hydroxy-acrylamide

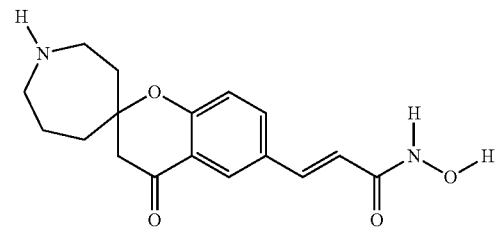 [SMILES: O=C(/C=C/c1ccc2c(c1)C(=O)CC1(CCCNCC1)O2)NO]

Step A

20% aqueous HCl (10 ml, 55 mmol) was added to a suspension of (±)-(E)-3-[1'-tert-butoxycarbonyl-4-oxo-spiro(chromane-2,4'-azepane)-6-yl]-acrylic acid methyl ester (Intermediate 3, Step B, 954 mg, 2.3 mmol) in glacial AcOH (10 ml). The mixture was stirred at 85° C. for 3 h and then evaporated under vacuum to give (±)-(E)-3-[4-oxo-spiro(chromane-2,4'-azepane)-6-yl]-acrylic acid (735 mg) as a white solid (hydrochloride salt).

Y=95%

LC-MS: (ES+) MH$^+$: 302

$^1$H NMR (CDCl$_3$) δ (ppm): 9.07 (bs, 2H), 7.98 (dd, J=8.51, 2.35 Hz, 1H), 7.95 (d, J=2.05 Hz, 1H), 7.59 (d, J=15.85 Hz, 1H), 7.14 (d, J=8.51 Hz, 1H), 6.46 (d, J=15.85 Hz, 1H), 3.00-3.33 (m, 4H), 2.95 (d, J=16.73 Hz, 1H), 2.89 (d, J=16.73 Hz, 1H), 2.06-2.36 (m, 3H), 1.84-2.05 (m, 2H), 1.62-1.84 (m, 1H).

Step B

TEA (2.49 ml, 17.9 mmol) was added to a suspension of (±)-(E)-3-[4-oxo-spiro(chromane-2,4'-azepane)-6-yl]-acrylic acid (670 mg, 1.99 mmol) in DCM (20 ml). BOC anhydride (520.6 mg, 2.39 mmol) was added after complete dissolution of the acid. The mixture was stirred at RT for 1 h, then poured into water (30 ml), neutralized with 5% aqueous citric acid solution and extracted with DCM (3 times 10 ml). The organic phase was dried over Na$_2$SO$_4$ and evaporated under vacuum. The crude product (750 mg) was used in the next step without purification.

Y=94%

LC-MS: (ES+) MH$^+$-100: 302

$^1$H NMR (DMSO-d$_6$) δ (ppm): 7.94 (dd, J=8.51, 2.05 Hz, 1H), 7.91 (d, J=2.05 Hz, 1H), 7.54 (d, J=15.85 Hz, 1H), 7.07 (d, J=8.51 Hz, 1H), 6.44 (d, J=16.14 Hz, 1H), 3.14-3.63 (m, 4H), 2.93 (d, J=17.02 Hz, 1H), 2.81 (d, J=16.73 Hz, 1H), 1.50-2.26 (m, 6H), 1.42 (s, 9H).

Step C

TEA (0.260 ml, 1.87 mmol) was added to solution of (±)-(E)-3-[1-tert-butoxycarbonyl-4-oxo-spiro(chromane-2,4'-azepane)-6-yl]-acrylic acid (500 mg, 1.25 mmol) in DCM (30 ml). The mixture was cooled down to 0° C., and EDC (357 mg, 1.87 mmol) and HOBt (252 mg, 1.87 mmol) were added. The mixture was stirred at 0° C. for 3 h, then NH$_2$OTHP (176 mg, 1.50 mmol) was added and the mixture was stirred at RT overnight. The solution was washed with a 5% aqueous NaHCO$_3$ solution and brine. The organic layer was then dried over Na$_2$SO$_4$ and evaporated. The crude residue was purified by column chromatography (eluent: DCM/MeOH 98:2) to give (E)-3-[1'-tert-butoxycarbonyl-4-oxo-spiro(chromane-2,4'-azepane)-6-yl]-N-(tetrahydro-pyran-2-yloxy)-acrylamide (307 mg).

Y=49%

LC-MS: (ES+) MH$^+$: 501

$^1$H NMR (DMSO-d$_6$) δ (ppm): 11.11 (bs, 1H), 7.90 (d, J=2.05 Hz, 1H), 7.80 (d, J=8.22 Hz, 1H), 7.48 (d, J=15.85 Hz, 1H), 7.08 (d, J=8.51 Hz, 1H), 6.47 (d, J=14.97 Hz, 1H), 4.91 (bs, 1H), 3.85-4.15 (m, 1H), 3.31-3.64 (m, 5H), 2.93 (d, J=17.31 Hz, 1H), 2.82 (d, J=16.73 Hz, 1H), 1.93-2.20 (m, 2H), 1.47-1.92 (m, 10 H), 1.42 (s, 9H).

Step D

1 M HCl in ether (10 ml, 10 mmol) was added dropwise to a solution of (E)-3-[1'-tert-butoxycarbonyl-4-oxo-spiro(chromane-2,4'-azepane)-6-yl]-N-(tetrahydro-pyran-2-yloxy)-acrylamide (307 mg, 0.61 mmol) in DCM (5 ml). The mixture was stirred at RT for 1 h. The precipitate was filtered off, washed with DCM, dried under vacuum and collected obtaining 202.4 mg of a white solid (hydrochloride salt).

Y=94%

LC-MS: Method B, rt=0.87; (ES+) MH$^+$: 317

$^1$H NMR (DMSO-d$_6$) δ (ppm): 9.24 (bs, 2H), 7.89 (d, J=2.05 Hz, 1H), 7.79 (dd, J=8.80, 2.05 Hz, 1H), 7.43 (d, J=15.85 Hz, 1H), 7.14 (d, J=8.51 Hz, 1H), 6.45 (d, J=15.85 Hz, 1H), 3.01-3.32 (m, 4H), 2.94 (d, J=17.02 Hz, 1H), 2.88 (d, J=16.73 Hz, 1H), 2.06-2.39 (m, 3H), 1.81-2.01 (m, 2H), 1.63-1.79 (m, 1H).

Example 23

(±)-(E)-3-[1'-Benzyl-4-oxo-spiro(chromane-2,4'-azepane)-6-yl]-N-hydroxy-acrylamide

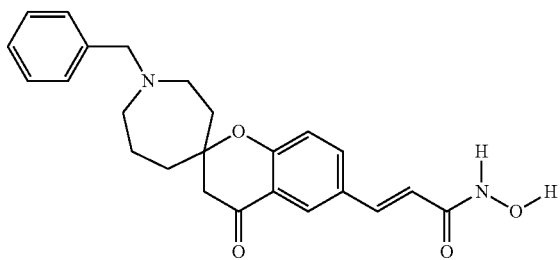 [SMILES: O=C(/C=C/c1ccc2c(c1)C(=O)CC1(CCCN(Cc3ccccc3)CC1)O2)NO]

Step A

A suspension of (±)-(E)-3-[4-oxo-spiro(chromane-2,4'-azepane)-6-yl]-acrylic acid methyl ester hydrochloride salt (500 mg, 1.43 mmol, Intermediate 3) in aqueous 10% NaHCO$_3$ solution was extracted with DCM (3 times 10 ml). The organic phase was dried over Na$_2$SO$_4$ and evaporated. The resulting oil was dissolved in DCM (15 ml), treated with benzaldehyde (0.174 ml, 1.71 mmol) and NaBH(OAc)$_3$ (455 mg, 2.14 mmol), and the resulting clear solution was stirred at RT for 2 h. Water was added to the mixture and the pH was adjusted to a basic pH value with NH$_3$. The mixture was extracted with DCM (3 times 10 ml). The organic layer was dried, evaporated, and the crude residue was purified by column chromatography (eluent: petroleum ether/EtOAc 7:3) to give (±)-(E)-3-[1'-benzyl-4-oxo-spiro(chromane-2,4'-azepane)-6-yl]-acrylic acid methyl ester (490 mg) as a light yellow solid.

Y=85%

LC-MS: (ES+) MH$^+$: 406

$^1$H NMR (CDCl$_3$) δ (ppm): 8.01 (d, J=2.35 Hz, 1H), 7.64 (dd, J=9.10, 2.64 Hz, 1H), 7.65 (d, J=15.85 Hz, 1H), 7.20-7.43 (m, 5H), 6.98 (d, J=8.80 Hz, 1H), 6.38 (d, J=15.85 Hz, 1H), 3.82 (s, 3H), 3.65 (bs, 2H), 2.83 (s, 2H), 2.63-2.81 (m, 3 H), 2.55 (bs, 1H), 2.08-2.29 (m, 2H), 1.90-2.05 (m, 2H), 1.79-1.90 (m, 1H), 1.61-1.73 (m, 1H).

Step B (±)-(E)-3-[1'-Benzyl-4-oxo-spiro(chromane-2,4'-azepane)-6-yl]-acrylic acid methyl ester (480 mg, 1.18 mmol) was hydrolyzed with aqueous 20% HCl solution and AcOH following the procedure described in Example 22, Step A, giving (±)-(E)-3-[1'-benzyl-4-oxo-spiro(chromane-2,4'-azepane)-6-yl]-acrylic acid (490 mg) as a white solid (hydrochloride salt).

Y=97%

LC-MS: (ES+) MH$^+$: 392

$^1$H NMR (DMSO-d$_6$) δ (ppm): 12.27 (bs, 1H), 10.60 (bs, 1H), 7.99 (dd, J=8.51, 2.35 Hz, 1H), 7.94 (d, J=1.76 Hz, 1H), 7.53-7.69 (m, 3H), 7.35-7.53 (m, 3H), 7.09 (d, J=8.80 Hz, 1H), 6.46 (d, J=16.14 Hz, 1H), 4.25-4.43 (m, 2H), 2.78-3.57, (m, 6H), 2.24-2.43 (m, 2H), 1.90-2.23 (m, 3H), 1.65-1.88 (m, 1H).

Step C (±)-(E)-3-[1'-Benzyl-4-oxo-spiro(chromane-2,4'-azepane)-6-yl]-acrylic acid (490 mg, 1.15 mmol) was reacted with NH$_2$OTHP following the procedure described in Example 22, Step C, giving (E)-3-[1'-benzyl-4-oxo-spiro(chromane-2,4'-azepane)-6-yl]-N-(tetrahydro-pyran-2-yloxy)-acrylamide (270 mg).

Y=48%

LC-MS: (ES+) MH$^+$: 491

$^1$H NMR (DMSO-d$_6$) δ (ppm): 11.10 (bs, 1H), 7.88 (d, J=2.35 Hz, 1H), 7.68-7.83 (m, 1H), 7.47 (d, J=15.85 Hz, 1H), 7.16-7.40 (m, 5H), 7.07 (d, J=8.51 Hz, 1H), 6.45 (d, J=15.55 Hz, 1H), 4.90 (bs, 1H), 3.84-4.08 (m, 1H), 3.60 (s, 2H), 3.46-3.58 (m, 1H), 2.94 (d, J=16.73 Hz, 1H), 2.88 (d, J=16.73 Hz, 1H), 2.53-2.77 (m, 4H), 1.85-2.15 (m, 4H), 1.47-1.80 (m, 8H).

Step D

1 M HCl in Et$_2$O (5 ml, 5 mmol) was added dropwise to a solution of (E)-3-[1'-benzyl-4-oxo-spiro(chromane-2,4'-azepane)-6-yl]-N-(tetrahydro-pyran-2-yloxy)-acrylamide (156 mg, 0.32 mmol) in DCM (3 ml). After 1 h stirring a white solid precipitated, which was then filtered off, washed with DCM, dried under vacuum and collected to give (±)-(E)-3-[1-benzyl-4-oxo-spiro(chromane-2,4'-azepane)-6-yl]-N-hydroxy-acrylamide (109 mg) as its hydrochloride salt.

Y=77%

LC-MS: Method B, rt=1.28; (ES+) MH$^+$: 407

$^1$H NMR (DMSO-d$_6$) δ (ppm): 10.93 (bs, 1H), 7.85-7.94 (m, 1H), 7.72-7.85 (m, 1 H), 7.54-7.72 (m, 2H), 7.32-7.54 (m, 4H), 7.10 (d, J=8.51 Hz, 1H), 6.44 (d, J=15.55 Hz, 1H), 4.22-4.45 (m, 2H), 2.76-3.67 (m, 6H), 2.11-2.44 (m, 3H), 1.96-2.11 (m, 2H), 1.71-1.88 (m, 1H).

Example 24

(±)-(E)-3-[1'-Acetyl-4-oxo-spiro(chromane-2,4'-azepane)-6-yl]-N-hydroxy-acrylamide

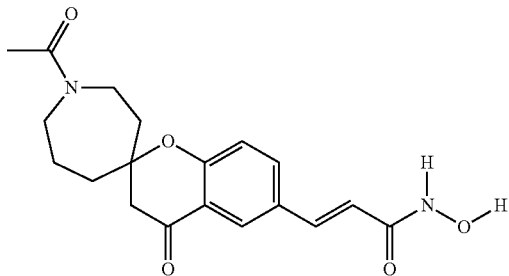 [SMILES: CC(=O)N1CCCC2(CC1)CC(=O)c1cc(/C=C/C(=O)NO)ccc1O2]

Step A

A suspension of (±)-(E)-3-[4-oxo-spiro(chromane-2,4'-azepane)-6-yl]acrylic acid methyl ester hydrochloride salt (500 mg, 1.43 mmol, Intermediate 3) in DCM (15 ml) was treated with acetyl chloride (0.121 ml, 1.72 mmol) and DIPEA (0.507 ml, 2.86 mmol) and was stirred at RT for 1. The solution was evaporated under vacuum and the crude product was purified by chromatography column (eluent: DCM/MeOH 95:5) to give (±)-(E)-3-[1'-acetyl-4-oxo-spiro(chromane-2,4'-azepane)-6-yl]-acrylic acid methyl ester (503 mg).

Y=98.5%

LC-MS: (ES+) MH$^+$: 358

$^1$H NMR (CDCl$_3$) δ (ppm): 8.04 (d, J=2.05 Hz, 1H), 7.65-7.73 (m, 1H), 7.66 (d, J=16.14 Hz, 1H), 7.02 (d, J=8.80 Hz, 1H), 6.40 (d, J=16.14 Hz, 1H), 3.82 (s, 3 H), 3.17-4.18 (m, 4H), 2.84 (d, J=16.73 Hz, 1H), 2.69 (d, J=16.73 Hz, 1H), 2.13 (s, 3H), 1.63-2.42 (m, 6H).

Step B (±)-(E)-3-[1'-Acetyl-4-oxo-spiro(chromane-2,4'-azepane)-6-yl]-acrylic acid methyl ester (500 mg, 1.40 mmol) was hydrolyzed with HCl and AcOH following the procedure described in Example 22, Step A, giving (E)-3-[1'-acetyl-4-oxo-spiro(chromane-2,4'-azepane)-6-yl]-acrylic acid as a white solid (475 mg, 98.9%). The acid was treated with NH$_2$OTHP according to the procedure described in Example 22, Step C, giving (E)-3-[1-acetyl-4-oxo-spiro(chromane-2,4'-azepane)-6-yl]-N-(tetrahydro-pyran-2-yloxy)-acrylamide (416 mg, 69.7%). Finally, removal of THP protecting group following the procedure described in Example 23, Step D gave (±)-(E)-3-[1'-acetyl-4-oxo-spiro(chromane-2,4'-azepane)-6-yl]-N-hydroxy-acrylamide (43 mg).

Y=15% (over 3 steps)

LC-MS: Method B, rt=1.23; (ES+) MH$^+$: 359

$^1$H NMR (DMSO-d$_6$) δ (ppm): 10.66 (s, 1H), 8.99 (s, 1H), 7.88 (s, 1H), 7.65-7.84 (m, 1H), 7.43 (d, J=15.85 Hz, 1H), 7.09 (d, J=8.51 Hz, 1H), 6.43 (d, J=15.85 Hz, 1H), 3.09-3.84 (m, 4H), 2.92 (d, J=16.73 Hz, 1H), 2.81 (d, J=16.73 Hz, 1H), 2.03-2.25 (m, 2H), 2.02 (s, 3H), 1.34-1.98 (m, 4H).

Example 25

(±)-(E)-3-[1'-Benzoyl-4-oxo-spiro(chromane-2,4'-azepane)-6-yl]-N-hydroxy-acrylamide

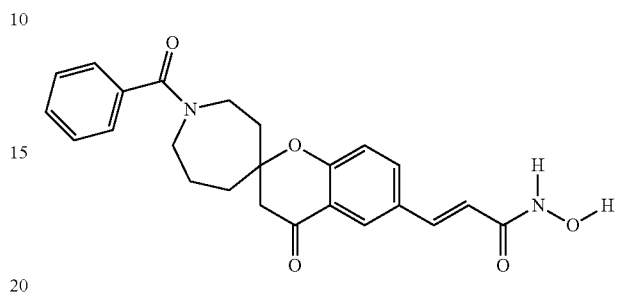

(±)-(E)-3-[1'-Benzoyl-4-oxo-spiro(chromane-2,4'-azepane)-6-yl]-acrylic acid methyl ester was obtained starting from hydrochloride salt of (±)-(E)-3-[4-oxo-spiro(chromane-2,4'-azepane)-6-yl]-acrylic acid methyl ester (300 mg, 0.85 mmol, Intermediate 3), benzoyl chloride (0.118 ml, 1.02 mmol) and DIPEA (0.303 ml, 1.70 mmol), according to the procedure described in Example 24, Step A, giving a light yellow solid (350 mg, 97.5%). The methyl ester group was hydrolyzed with aqueous 25% HCl solution and AcOH following the procedure described in Example 22, Step A, giving (±)-(E)-3-[1'-benzoyl-4-oxo-spiro(chromane-2,4'-azepane)-6-yl]-acrylic acid as a white solid (300 mg, 85.7%). The obtained acid was treated with NH$_2$OTHP according to the procedure described in Example 22, Step C, giving (E)-3-[1'-benzoyl-4-oxo-spiro(chromane-2,4'-azepane)-6-yl]-N-(tetrahydro-pyran-2-yloxy)-acrylamide (180 mg, 48%). Finally, removal of THP protecting group (160 mg) following the procedure described in Example 22, Step D gave (±)-(E)-3-[1'-benzoyl-4-oxo-spiro(chromane-2,4'-azepane)-6-yl]-N-hydroxy-acrylamide (76.4 mg) as a red solid.

Y=23% (over 4 steps)

LC-MS: Method D, rt=3.95; (ES+) MH$^+$: 421

$^1$H NMR (DMSO-d$_6$ 353 K) δ (ppm): 10.33 (bs, 1H), 8.60 (bs, 1H), 7.88 (d, J=2.05 Hz, 1H), 7.75 (dd, J=8.80, 2.35 Hz, 1H), 7.31-7.51 (m, 6H), 7.08 (d, J=8.51 Hz, 1H), 6.48 (d, J=16.14 Hz, 1H), 3.41-3.75 (m, 4H), 2.92 (d, J=16.73 Hz, 1H), 2.84 (d, J=16.73 Hz, 1H), 2.07-2.20 (m, 2H), 1.78-2.04 (m, 3H), 1.52-1.73 (m, 1 H).

Example 26

(±)-(E)-3-[1-Methyl-4-oxo-spiro(chromane-2,4'-azepane)-6-yl]-N-hydroxy-acrylamide

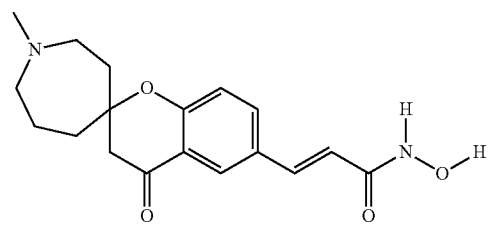 [SMILES: CN1CCCC2(CC1)CC(=O)c1cc(/C=C/C(=O)NO)ccc1O2]

Step A (±)-(E)-3-[1'-Methyl-4-oxo-spiro(chromane-2,4'-azepane)-6-yl]-acrylic acid methyl ester was synthesized starting from the hydrochloride salt of (±)-(E)-3-[4-oxo-spiro(chromane-2,4'-azepane)-6-yl]-acrylic acid methyl ester (500 mg, 1.43 mmol, Intermediate 3), according to the procedure for preparation of Example 23, Step A, using aqueous 37% formaldehyde solution (0.127 ml, 1.71 mmol), and NaBH(OAc)$_3$ (461 mg, 2.14 mmol) giving a yellow solid (374 mg).

Y=79%

LC-MS: (ES+) MH$^+$: 330

$^1$H NMR (DMSO-d$_6$) δ (ppm): 7.86-8.08 (m, 2H), 7.66 (d, J=16.14 Hz, 1H), 7.07 (d, J=9.10 Hz, 1H), 6.55 (d, J=16.14 Hz, 1H), 3.72 (s, 3H), 2.91 (d, J=16.73 Hz, 1H), 2.85 (d, J=16.73 Hz, 1H), 2.53-2.69 (m, 3H), 2.42 (ddd, J=13.20, 7.63, 2.05 Hz, 1H), 2.25 (s, 3H), 1.83-2.12 (m, 4H), 1.64-1.81 (m, 1H), 1.42-1.63 (m, 1H).

Step B (±)-(E)-3-[1'-Methyl-4-oxo-spiro(chromane-2,4'-azepane)-6-yl]-acrylic acid methyl ester (370 mg, 1.12 mmol) was hydrolyzed with HCl and AcOH according to the procedure for preparation of Example 23, Step B, giving (±)-(E)-3-[1'-methyl-4-oxo-spiro(chromane-2,4'-azepane)-6-yl]-acrylic acid (334 mg) as a white solid (hydrochloride salt).

Y=85%

LC-MS: (ES+) MH$^+$: 316

$^1$H NMR (DMSO-d$_6$) δ (ppm): 11.00 (bs, 1H), 7.83-8.05 (m, 2H), 7.59 (d, J=15.85 Hz, 1H), 7.12 (d, J=8.51 Hz, 1H), 6.46 (d, J=16.14 Hz, 1H), 3.32-3.62 (m, 2H), 3.01-3.32 (m, 2H), 2.81-3.00 (m, 2H), 2.74 (d, J=4.99 Hz, 3H), 1.60-2.43 (m, 6 H).

Step C (±)-(E)-3-[1'-Methyl-4-oxo-spiro(chromane-2,4'-azepane)-6-yl]-acrylic acid (330 mg, 0.94 mmol) was treated with NH$_2$OTHP according to the procedure described in Example 23, Step C, giving (±)-(E)-3-[1'-methyl-4-oxo-spiro(chromane-2,4'-azepane)-6-yl]-N-(tetrahydro-pyran-2-yloxy)-acrylamide as a yellow solid (220 mg).

Y=57%

LC-MS: (ES+) MH$^+$: 415

$^1$H NMR (DMSO-d$_6$) δ (ppm): 11.12 (bs, 1H), 7.89 (d, J=2.05 Hz, 1H), 7.78 (d, J=9.10 Hz, 1H), 7.47 (d, J=15.85 Hz, 1H), 7.07 (d, J=8.51 Hz, 1H), 6.46 (d, J=16.14 Hz, 1H), 4.91 (bs, 1H), 3.82-4.02 (m, 1H), 3.49-3.63 (m, 1H), 2.91 (d, J=16.73 Hz, 1H), 2.85 (d, J=16.73 Hz, 1H), 2.54-2.79 (m, 4H), 2.32 (s, 3H), 1.84-2.14 (m, 6H), 1.49-1.82 (m, 6H).

Step D (±)-(E)-3-[1'-Methyl-4-oxo-spiro(chromane-2,4'-azepane)-6-yl]-N-hydroxy acrylamide was synthesized starting from (E)-3-[1'-methyl-4-oxo-spiro(chromane-2,4'-azepane)-6-yl]-N-(tetrahydro-pyran-2-yloxy)-acrylamide (220 mg, 0.53 mmol) according to the procedure described in Example 23, Step D. After purification by preparative HPLC, the product was obtained as light red solid (58 mg) as its trifluoroacetic salt.

Y=25%

LC-MS: Method B, rt=0.86; (ES+) MH$^+$: 331

$^1$H NMR (DMSO-d$_6$+Na$_2$CO$_3$) δ (ppm): 7.81 (d, J=2.05 Hz, 1H), 7.68-7.77 (m, 1 H), 7.29 (d, J=15.85 Hz, 1H), 7.03 (d, J=8.80 Hz, 1H), 6.37 (d, J=15.85 Hz, 1H), 2.89 (d, J=16.73 Hz, 1H), 2.83 (d, J=16.73 Hz, 1H), 2.53-2.67 (m, 3H), 2.40 (ddd, J=13.35, 7.63, 1.91 Hz, 1H), 2.24 (s, 3H), 1.82-2.12 (m, 4H), 1.61-1.82 (m, 1H), 1.38-1.61 (m, 1H).

Example 27

(±)-(E)-3-[1'-Ethyloxycarbonyl-4-oxo-spiro(chromane-2,4'-azepane)-6-yl]-N-hydroxy-acrylamide

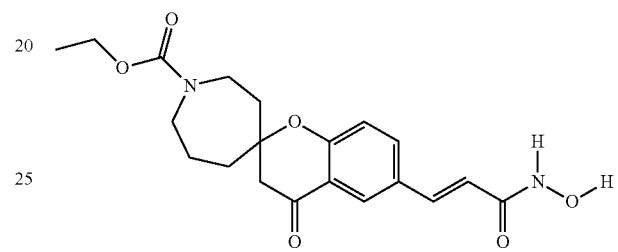

(±)-(E)-3-[1'-Ethyloxycarbonyl-4-oxo-spiro(chromane-2,4'-azepane)-6-yl]-acrylic acid methyl ester was obtained starting from the hydrochloride salt of (±)-(E)-3-[4-oxo-spiro(chromane-2,4'-azepane)-6-yl]-acrylic acid methyl ester (500 mg, 1.43 mmol, Intermediate 3) and ethyl chloro formate (0.163 ml, 1.70 mmol), according to the procedure described in Example 24, Step A, giving a yellow solid (540 mg, 97%). (±)-(E)-3-[1'-Ethyloxycarbonyl-4-oxo-spiro(chromane-2,4'-azepane)-6-yl]-acrylic acid methyl ester (530 mg, 1.37 mmol) was hydrolyzed using HCl and AcOH following the procedure described in Example 22, Step A. (±)-(E)-3-[1'-ethyloxycarbonyl-4-oxo-spiro(chromane-2,4'-azepane)-6-yl]-acrylic acid was obtained after column chromatography (eluent DCM/MeOH 9:1) as a white solid (101 mg, 21%). Hydrolysis of the carbamate function was not observed. The acrylic acid (100 mg, 0.26 mmol) was then treated with NH$_2$OTHP according to the procedure described in Example 22, Step C, giving (E)-3-[1'-ethyloxycarbonyl-4-oxo-spiro(chromane-2,4'-azepane)-6-yl]-N-(tetrahydro-pyran-2-yloxy)-acrylamide (82 mg, 65%). Finally, removal of THP protecting group following the procedure described in Example 22, Step D gave (±)-(E)-3-[1'ethyloxycarbonyl-4-oxo-spiro(chromane-2,4'-azepane)-6-yl]-N-hydroxy-acrylamide (12.8 mg) as a light yellow solid.

Y=2.5% (over 4 steps)

LC-MS: Method B, rt=1.81; (ES+) MH$^+$: 389

$^1$H NMR (DMSO-d$_6$) δ (ppm): 10.65 (bs, 1H), 7.88 (d, J=2.35 Hz, 1H), 7.78 (dd, J=8.51, 1.76 Hz, 1H), 7.43 (d, J=15.55 Hz, 1H), 7.07 (d, J=8.51 Hz, 1H), 6.41 (d, J=15.85 Hz, 1H), 4.06 (qd, J=7.04, 0.88 Hz, 2H), 3.23-3.49 (m, 4H), 2.92 (d, J=16.73 Hz, 1H), 2.81 (d, J=16.73 Hz, 1H), 1.96-2.20 (m, 2H), 1.77-1.93 (m, 2 H), 1.52-1.74 (m, 2H), 1.19 (td, J=6.82, 2.20 Hz, 3H).

Example 28

(±)-(E)-3-[1'(2-Phenyl-ethyl)-4-oxo-spiro(chromane-2,4'-azepane)-6-yl]-N-hydroxy-acrylamide

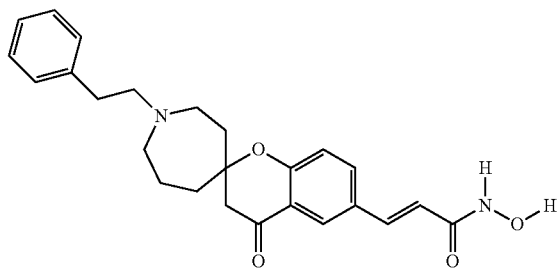 [SMILES: O=C(/C=C/c1ccc2c(c1)C(=O)CC1(CCCN(CCc3ccccc3)CC1)O2)NO]

(±)-(E)-3-[1'-(2-Phenyl-ethyl)-4-oxo-spiro(chromane-2,4'-azepane)-6-yl]-acrylic acid methyl ester was obtained starting from the hydrochloride salt of (±)-(E)-3-[4-oxo-spiro(chromane-2,4'-azepane)-6-yl]-acrylic acid methyl ester (1 g, 2.85 mmol, Intermediate 3) and phenethyl bromide (0.846 ml, 6.27 mmol), according to the procedure described in Example 24, Step A. The reaction was carried out for 15 days at RT and the methyl ester was obtained as a yellow solid (203 mg, 17%). (±)-(E)-3-[1'-(2-Phenyl-ethyl)-4-oxo-spiro(chromane-2,4'-azepane)-6-yl]-acrylic acid methyl ester (200 mg, 0.48 mmol) was hydrolyzed with HCl and AcOH following the procedure described in Example 22, Step A, giving (±)-(E)-3-[1'-(2-phenyl-ethyl)-4-oxo-spiro(chromane-2,4'-azepane)-6-yl]-acrylic acid as a white solid (197 mg, 93%). The acid was treated with NH$_2$OTHP according to the procedure described in Example 22, Step C, giving (E)-3-[1'(2-phenyl-ethyl)-4-oxo-spiro(chromane-2,4'-azepane)-6-yl]-N-(tetrahydro-pyran-2-yloxy)-acrylamide (183 mg, 83%). Finally, removal of THP protecting group following the procedure described in Example 22, Step D and purification using preparative HPLC gave (±)-(E)-3-[1'-(2-phenyl-ethyl)-4-oxo-spiro(chromane-2,4'-azepane)-6-yl]N-hydroxy-acrylamide (77.5 mg, 40%) as its trifluoroacetate salt.

Y=5% (over 4 steps).

LC-MS: Method B, rt=1.39; (ES+) MH$^+$: 421

$^1$H NMR (300 MHz, DMSO-d$_6$+Na$_2$CO$_3$) δ (ppm): 7.81 (d, J=1.47 Hz, 1H), 7.73 (dd, J=8.66, 1.91 Hz, 1H), 7.09-7.39 (m, 6H), 7.03 (d, J=8.80 Hz, 1H), 6.37 (d, J=15.55 Hz, 1H), 2.89 (d, J=16.73 Hz, 1H), 2.83 (d, J=16.73 Hz, 1H), 2.53-2.79 (m, 6H), 1.82-2.09 (m, 4H), 1.71-1.80 (m, 1H), 1.38-1.60 (m, 1H).

Example 29

(±)-(E)-3-[1'-(4-Fluoro-benzyl)-4-oxo-spiro(chromane-2,4'-azepane)-6-yl]-N-hydroxy-acrylamide

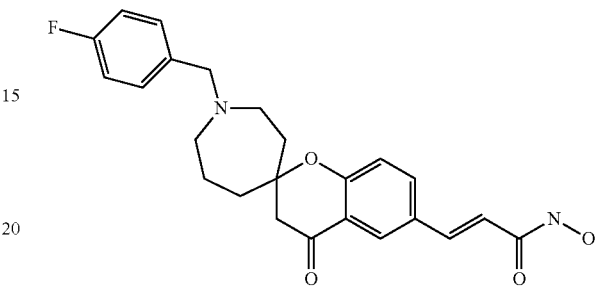

Step A (±)-(E)-3-[4-Oxo-spiro(chromane-2,4'-azepane)-6-yl]-acrylic acid methyl ester hydrochloride (Intermediate 3, 650 mg, 1.85 mmol) was suspended in DCM (100 ml). TEA (0.258 ml, 1.85 mmol) was added and the pH was adjusted to 5 with AcOH. 4-Fluorobenzaldehyde (275 mg, 2.22 mmol) and NaBH(OAc)$_3$ (587 mg, 2.77 mmol) were added and the mixture was stirred for 6 h at RT, then washed with a saturated NaHCO$_3$ solution brine, dried over Na$_2$SO$_4$ and evaporated to dryness. The crude mixture was purified by column chromatography (eluent DCM/MeOH 99:1) to give (±)-(E)-3-[1'(4-fluoro-benzyl)-4-oxo-spiro(chromane-2,4'-azepane)-6-yl]-acrylic acid methyl ester (550 mg)

Y=70%

LC-MS: (ES+) 424

$^1$H NMR (DMSO-d$_6$) δ (ppm): 7.95 (d, J=2.35 Hz, 1H), 7.96 (dd, J=9.10, 2.35 Hz, 1H), 7.65 (d, J=15.85 Hz, 1H), 7.25-7.41 (m, 2H), 7.09-7.18 (m, 2H), 7.06 (d, J=9.10 Hz, 1H), 6.54 (d, J=16.14 Hz, 1H), 3.71 (s, 3H), 3.57 (s, 2H), 2.93 (d, J=16.73 Hz, 1H), 2.87 (d, J=16.43 Hz, 1H), 2.54-2.77 (m, 4H), 1.83-2.16 (m, 4H), 1.65-1.83 (m, 1H), 1.44-1.65 (m, 1H).

Step B (±)-(E)-3-[1-(4-Fluoro-benzyl)-4-oxo-spiro(chromane-2,4'-azepane)-6-yl]-acrylic acid methyl ester (530 mg, 1.25 mmol) was treated with 1 M NaOH according to procedure described for Example 16 STEP B to give (±)-(E)-3-[1-(4-fluoro-benzyl)-4-oxo-spiro(chromane-2,4'-azepane)-6-yl]-acrylic acid (479 mg, 86%).

The acid was treated with NH$_2$OTHP according to the procedure described in Example 16, Step C, giving (±)-(E)-3-[1'(4-fluoro-benzyl)-4-oxo-spiro(chromane-2,4'-azepane)-6-yl]-N-(tetrahydro-pyran-2-yloxy)-acrylamide.

Removal of the THP protecting group following the procedure described in Example 16, Step C, gave (±)-(E)-3-[1'-(4-fluoro-benzyl)-4-oxo-spiro(chromane-2,4'-azepane)-6-yl]-N-hydroxy-acrylamide hydrochloride as pale yellow powder (117 mg, 20% over three steps)

LC-MS: Method F, rt=1.42; (ES+) MH$^+$: 425

$^1$H NMR (DMSO-d$_6$+Na$_2$CO$_3$) δ (ppm): 7.82 (s, 1H), 7.73 (dd, J=8.36, 1.32 Hz, 1H), 7.25-7.46 (m, 3H), 7.07-7.19 (m, 2H), 7.04 (d, J=8.51 Hz, 1H), 6.41 (d, J=15.85 Hz, 1H), 3.57 (s, 2H), 2.92 (d, J=16.73 Hz, 1H), 2.85 (d, J=16.73 Hz, 1H), 2.53-2.77 (m, 3H), 2.40-2.47 (m, 1H), 1.84-2.21 (m, 4H), 1.62-1.84 (m, 1H), 1.35-1.60 (m, 1H).

Example 30

(E)-3-[4-oxo-spiro(chromane-2,3'-azetidine)-6-yl]-N-hydroxy-acrylamide

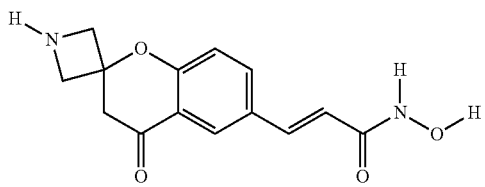 [SMILES: O=C(/C=C/c1ccc2c(c1)C(=O)CC1(CNC1)O2)NO]

Step A

1 M NaOH (1.60 ml) was added to a solution of (E)-3-[1'-tert-butoxycarbonyl-4-oxo-spiro(chromane-2,3'-azetidine)-6-yl]-acrylic acid methyl ester (Intermediate 4, Step B, 450 mg, 1.20 mmol) in water (11 ml) and dioxane (22 ml). The mixture was stirred at RT for 5 h. Aqueous HCl 10% was added until reaching pH 7, dioxane was removed under vacuum and the residue was diluted with water. The aqueous layer was acidified to pH 5 with 10% aqueous HCl and the product was extracted with DCM (3×30 ml). The collected organic phases were dried over $Na_2SO_4$ and concentrated to give (E)-3-[1'-tert-butoxycarbonyl-4-oxo-spiro(chromane-2,3'-azetidine)-6-yl]-acrylic acid (430 mg) as a yellow solid.

Y=100%

LC-MS: (ES+) MH$^+$-56: 304

$^1$H NMR (300 MHz, DMSO-d$_6$) δ (ppm): 2.33 (bs, 1H), 8.00 (dd, J=8.51, 2.05 Hz, 1H), 7.96 (d, J=2.35 Hz, 1H), 7.60 (d, J=16.14 Hz, 1H), 7.20 (d, J=8.51 Hz, 1H), 6.48 (d, J=16.14 Hz, 1H), 4.01 (d, J=9.68 Hz, 2H), 3.91 (d, J=9.39 Hz, 2H), 3.20 (s, 2H), 1.39 (s, 9H).

Step B

TEA (0.25 ml, 1.8 mmol) was added to a suspension of (E)-3-[1'-tert-butoxycarbonyl-4-oxo-spiro(chromane-2,3'-azetidine)-6-yl]-acrylic acid (430 mg, 1.20 mmol) in DCM (13 ml) and the reaction mixture was stirred at RT for 5 min. The resulting clear solution was cooled down to 0° C., EDC (344 mg, 1.80 mmol) and HOBt (243 mg, 1.80 mmol) were added and the mixture was stirred at 0° C. for 2 h. NH$_2$OTHP (168 mg, 1.43 mmol) was added and the mixture was stirred at RT overnight. The reaction mixture was washed with 5% aqueous NaHCO$_3$ solution and brine, the organic layer was dried over Na$_2$SO$_4$, filtered and evaporated. The crude residue was purified by column chromatography on silica gel (eluent: DCM/MeOH 98:2) to give (E)-3-[1'-tert-butoxycarbonyl-4-oxo-spiro(chromane-2,3'-azetidine)-6-yl]-N-(tetrahydro-pyran-2-yloxy)-acrylamide (0.40 g) as a pale yellow solid.

Y=73%

LC-MS: (ES+) M-83: 375

$^1$H NMR (300 MHz, DMSO-d$_6$) δ (ppm): 11.13 (bs, 1H), 7.93 (d, J=2.35 Hz, 1H), 7.84 (d, J=8.80 Hz, 1H), 7.50 (d, J=15.85 Hz, 1H), 7.21 (d, J=8.51 Hz, 1H), 6.50 (d, J=15.85 Hz, 1H), 4.91 (bs, 1H), 4.00 (d, J=9.39 Hz, 2H), 3.93-3.98 (m, 1H), 3.90 (d, J=9.39 Hz, 2H), 3.44-3.74 (m, 1H), 3.20 (s, 2H), 1.48-1.84 (m, 6H), 1.39 (s, 9H).

Step C

4 M HCl in dioxane (1.90 ml) was added dropwise to a solution of (E)-3-[1'-tert-butoxycarbonyl-4-oxo-spiro(chromane-2,3'-azetidine)-6-yl]-N-(tetrahydro-pyran-2-yloxy)-acrylamide (360 mg, 0.78 mmol) in DCM (14 ml). The mixture was stirred at RT overnight. The formed precipitate was filtered off, washed with DCM, dried under vacuum to give (E)-3-[4-oxo-spiro(chromane-2,3'-azetidine)-6-yl]-N-hydroxy-acrylamide (154 mg, hydrochloride salt) as a white solid.

Y=65%, purity=100%

LC-MS: Method C, rt=1.27; (ES+) MH$^+$: 275

$^1$H NMR (300 MHz, DMSO-d$_6$) δ (ppm): 10.71 (bs, 1H), 9.42 (bs, 1H), 9.24 (bs, 1 H), 7.92 (d, J=2.05 Hz, 1H), 7.86 (dd, J=8.80, 2.05 Hz, 1H), 7.46 (d, J=15.85 Hz, 1H), 7.21 (d, J=8.80 Hz, 1H), 6.46 (d, J=15.55 Hz, 1H), 4.03-4.33 (m, 4H), 3.31 (s, 2H).

Example 31

(E)-3-[1'-Benzyl-4-oxo-spiro(chromane-2,3'-azetidine)-6-yl]-N-hydroxy-acrylamide

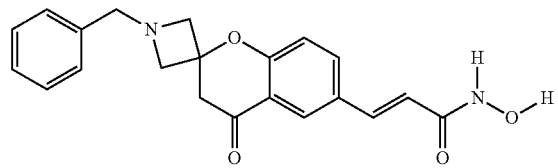 [SMILES: O=C(/C=C/c1ccc2c(c1)C(=O)CC1(CN(Cc3ccccc3)C1)O2)NO]

Step A

A suspension of Intermediate 4 (500 mg, 1.62 mmol) in aqueous 10% NaHCO$_3$ solution was extracted with DCM (3×10 ml). The organic phases were collected, dried over Na$_2$SO$_4$, filtered and evaporated to give the corresponding free base as pale yellow oil. The oil was dissolved in DCM (16 ml), treated with benzaldehyde (0.34 ml, 3.2 mmol) and NaBH(OAc)$_3$ (515 mg, 2.43 mmol) and the mixture was stirred at RT for 2 h. Water was added and the pH value was adjusted to 8 with aqueous NH$_3$. The mixture was extracted with DCM (3×10 ml) and the combined organic layers were dried over Na$_2$SO$_4$, filtered and evaporated, to give the (E)-3-[1'-benzyl-4-oxo-spiro(chromane-2,3'-azetidine)-6-yl]-acrylic acid methyl ester (560 mg) as a light yellow oil.

Y=95%

LC-MS: (ES+) MH$^+$:364

$^1$H NMR (300 MHz, DMSO-d$_6$) δ (ppm) 7.95-8.05 (m, 2H), 7.67 (d, J=16.14 Hz, 1H), 7.20-7.39 (m, 5H), 7.17 (d, J=8.80 Hz, 1H), 6.58 (d, J=15.85 Hz, 1H), 3.72 (s, 3H), 3.66 (s, 2H), 3.37 (d, J=8.80 Hz, 2H), 3.24 (d, J=8.80 Hz, 2H), 3.14 (s, 2H).

Step B (E)-3-[1'-Benzyl-4-oxo-spiro(chromane-2,3'-azetidine)-6-yl]-acrylic acid methyl ester (540 mg, 1.48 mmol) was dissolved in acetic acid (10 ml), then 6 M HCl (10 ml) was added and the resulting suspension was heated to 85° C. for 4 h. The solvents were evaporated and the residue was dried under vacuum, giving (E)-3-[1'-benzyl-4-oxo-spiro(chromane-2,3'-azetidine)-6-yl]-acrylic acid (490 mg, hydrochloride salt) as a light yellow solid.

Y=86%

LC-MS: (ES+) MH$^+$: 350

$^1$H NMR (300 MHz, DMSO-d$_6$+Na$_2$CO$_3$) δ (ppm) 7.78 (dd, J=8.51, 2.05 Hz, 1H), 7.74 (d, J=2.05 Hz, 1H), 7.19-7.44 (m, 5H), 7.12 (d, J=16.14 Hz, 1H), 7.09 (d, J=8.51 Hz, 1H), 6.33 (d, J=15.85 Hz, 1H), 3.66 (s, 2H), 3.35-3.39 (m, 2H), 3.22 (d, J=8.51 Hz, 2H), 3.10 (s, 2H).

Step C

A suspension of (E)-3-[1'-benzyl-4-oxo-spiro(chromane-2,3'-azetidine)-6-yl]-acrylic acid (490 g, 1.30 mmol) in DCM (6.5 ml) was treated with TEA (0.12 ml, 0.90 mmol) and then with EDC (172 mg, 0.900 mmol), HOBt (122 mg, 0.904 mmol) and NH$_2$OTHP (82 mg, 0.72 mmol) following the procedure described in Example 30, Step B, giving (E)-3-[1'-benzyl-4-oxo-spiro(chromane-2,3'-azetidine)-6-yl]-N-(tetrahydro-pyran-2-yloxy)-acrylamide (380 g) as a white solid.

Y=65%

LC-MS: (ES+) MH$^+$: 449

$^1$H NMR (300 MHz, DMSO-d$_6$) δ (ppm) 11.12 (bs, 1H), 7.90 (d, J=2.35 Hz, 1H), 7.81 (d, J=8.80 Hz, 1H), 7.47 (d, J=15.85 Hz, 1H), 7.20-7.37 (m, 5H), 7.17 (d, J=8.80 Hz, 1H), 6.48 (d, J=15.55 Hz, 1H), 4.91 (t, J=3.08 Hz, 1H), 3.87-4.02 (m, 1H), 3.67 (s, 2H), 3.45-3.61 (m, 1H), 3.37 (d, J=8.80 Hz, 2H), 3.23 (d, J=8.80 Hz, 2H), 3.13 (s, 2H), 1.45-1.78 (m, 6H).

Step D

1 M HCl in Et$_2$O (5.0 ml) was added dropwise to a solution of (E)-3-[1'-benzyl-4-oxo-spiro(chromane-2,3'-azetidine)-6-yl]-N-(tetrahydro-pyran-2-yloxy)-acrylamide (360 g, 0.80 mmol) in DCM (4 ml). The mixture was stirred at RT overnight. The formed precipitate was filtered off, washed with DCM, dried under vacuum and purified by preparative HPLC to give (E)-3-[1'-benzyl-4-oxo-spiro(chromane-2,3'-azetidine)-6-yl]-N-hydroxy-acrylamide (290 mg, trifluoroacetate salt) as a white solid.

Y=76%, purity 97.3%

LC-MS: Method H, rt=1.10; (ES+) MH$^+$: 365

$^1$H NMR (300 MHz, DMSO-d$_6$) δ (ppm) 11.11 (bs, 1H), 10.70 (bs, 1H), 7.91 (d, J=2.05 Hz, 1H), 7.85 (d, J=8.22 Hz, 1H), 7.40-7.59 (m, 6H), 7.06-7.32 (m, 1H), 6.45 (d, J=15.85 Hz, 1H), 4.46 (bs, 2H), 4.10-4.42 (m, 4H), 3.34 (s, 2H).

Example 32

(E)-3-[1'(2-Phenyl-ethyl)-4-oxo-spiro(chromane-2,3'-azetidine)-6-yl]-N-hydroxy-acrylamide

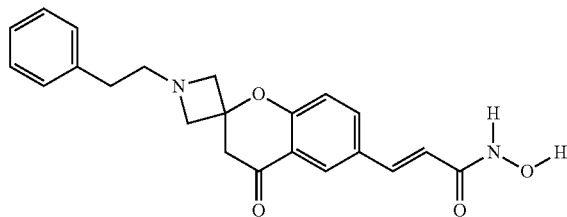 [SMILES: O=C(/C=C/c1ccc2c(c1)C(=O)CC1(CN(CCc3ccccc3)C1)O2)NO]

Step A (E)-3-[1'-(2-Phenyl-ethyl)-4-oxo-spiro(chromane-2,3'-azetidine)-6-yl]acrylic acid methyl ester was synthesized starting from Intermediate 4 (350 mg, 1.13 mmol), according to the procedure described in Example 31, Step A, using phenylacetaldehyde (0.25 ml, 2.3 mmol) and NaBH(OAc)$_3$ (360 mg, 1.69 mmol). The product was obtained as a yellow solid (378 mg).

Y=89%

LC-MS: (ES+) MH$^+$: 378

$^1$H NMR (300 MHz, DMSO-d$_6$) δ (ppm) 7.89-8.17 (m, 2H), 7.67 (d, J=16.14 Hz, 1H), 7.05-7.35 (m, 6H), 6.58 (d, J=16.14 Hz, 1H), 3.72 (s, 3H), 3.37 (d, J=8.80 Hz, 2H), 3.18 (d, J=8.51 Hz, 2H), 3.11 (s, 2H), 2.64-2.81 (m, 2H), 2.53-2.64 (m, 2H).

Step B (E)-3-[1'-(2-Phenyl-ethyl)-4-oxo-spiro(chromane-2,3'-azetidine)-6-yl]-acrylic acid methyl ester (350 mg, 0.93 mmol) was hydrolyzed with AcOH (6 ml) and aqueous 20% HCl solution (6 ml) following the procedure described in Example 31, Step B, giving (E)-3-[1'-(2-phenyl-ethyl)-4-oxo-spiro(chromane-2,3'-azetidine)-6-yl]-acrylic acid (320 mg, hydrochloride salt) as a yellow solid.

Y=86%

LC-MS: (ES+) MH$^+$: 364

$^1$H NMR (300 MHz, DMSO-d$_6$) δ (ppm) 11.08 (bs, 1H), 8.01-8.09 (m, 1H), 7.99 (d, J=2.05 Hz, 1H), 7.62 (d, J=16.14 Hz, 1H), 7.12-7.43 (m, 6H), 6.50 (d, J=15.85 Hz, 1H), 4.06-4.67 (m, 4H), 3.33-3.68 (m, 4H), 2.76-2.98 (m, 2H).

Step C

A suspension of (E)-3-[1-(2-phenyl-ethyl)-4-oxo-spiro (chromane-2,3'-azetidine)-6-yl]-acrylic acid (320 mg, 0.80 mmol) in DCM (10 ml) was treated with TEA (0.18 ml, 1.3 mmol) and then with EDC (252 mg, 1.32 mmol), HOBt (178 mg, 1.32 mmol) and NH$_2$OTHP (124 mg, 1.06 mmol) following the procedure described in Example 30, Step B, giving (E)-3-[1'(2-phenyl-ethyl)-4-oxo-spiro(chromane-2,3'-azetidine)-6-yl]-N-(tetrahydro-pyran-2-yloxy)-acrylamide (203 mg) as a white solid.

Y=55%

LC-MS: (ES+) MH$^+$: 463

$^1$H NMR (300 MHz, DMSO-d$_6$) δ (ppm) 11.12 (bs, 1H), 7.91 (d, J=2.35 Hz, 1H), 7.71-7.87 (m, 1H), 7.48 (d, J=16.14 Hz, 1H), 7.09-7.33 (m, 6H), 6.48 (d, J=15.26 Hz, 1H), 4.91 (bs, 1H), 3.78-4.06 (m, 1H), 3.45-3.64 (m, 1H), 3.37 (d, J=8.51 Hz, 2H), 3.18 (d, J=8.51 Hz, 2H), 3.10 (s, 2H), 2.66-2.76 (m, 2H), 2.54-2.61 (m, 2H), 1.32-1.91 (m, 6H).

Step D (E)-3-[1'-(2-Phenyl-ethyl)-4-oxo-spiro(chromane-2,3'-azetidine)-6-yl]-N-(tetrahydro-pyran-2-yloxy)-acrylamide (180 mg, 0.39 mmol) in DCM (7 ml) was treated with 4 M HCl in dioxane (1 ml) as described in Example 30, Step C, giving (E)-3-[1'-(2-phenyl-ethyl)-4-oxo-spiro(chromane-2,3'-azetidine)-6-yl]-N-hydroxy-acrylamide (131 mg, hydrochloride salt) as a white solid.

Y=83%, purity 95.2%

LC-MS: Method F, rt=1.28; (ES+) MH$^+$: 379

$^1$H NMR (300 MHz, DMSO-d$_6$) δ (ppm) 11.16 (bs, 1H), 10.70 (bs, 1H), 7.92 (d, J=2.05 Hz, 1H), 7.76-7.90 (m, 1H), 7.47 (d, J=15.55 Hz, 1H), 7.07-7.40 (m, 6H), 6.47 (d, J=15.85 Hz, 1H), 4.35-4.55 (m, 2H), 4.26-4.35 (m, 2H), 3.44-3.63 (m, 2 H), 3.19-3.43 (m, 2H), 2.75-2.98 (m, 2H).

Example 33

(E)-3-[1'-(4-Fluoro-benzyl)-4-oxo-spiro(chromane-2,3'-azetidine)-6-yl]-N-hydroxy-acrylamide

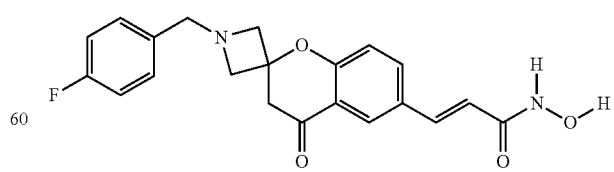

Step A (E)-3-[1'-(4-Fluoro-benzyl)-4-oxo-spiro(chromane-2,3'-azetidine)-6-yl]-acrylic acid methyl ester was synthesized starting from Intermediate 4 (350 mg, 1.13 mmol), according to the procedure described in Example 31, Step A, using 4-fluorobenzaldehyde (0.24 ml, 2.26 mmol) and NaBH(OAc)$_3$ (360 mg, 1.69 mmol). The product was obtained as a yellow solid (390 mg).

Y=91%

LC-MS: (ES+) MH$^+$: 382

$^1$H NMR (300 MHz, DMSO-d$_6$) δ (ppm) 8.00 (dd, J=8.22, 2.35 Hz, 1H), 7.98 (d, J=2.35 Hz, 1H), 7.67 (d, J=16.14 Hz, 1H), 7.24-7.38 (m, 2H), 7.17 (d, J=8.51 Hz, 1H), 7.03-7.15 (m, 2H), 6.58 (d, J=15.85 Hz, 1H), 3.72 (s, 3H), 3.65 (s, 2 H), 3.37 (d, J=8.80 Hz, 2H), 3.23 (d, J=8.80 Hz, 2H), 3.13 (s, 2H).

Step B (E)-3-[1'-(4-Fluoro-benzyl)-4-oxo-spiro(chromane-2,3'-azetidine)-6-yl]-acrylic acid methyl ester (360 mg, 0.94 mmol) was hydrolyzed with AcOH (6 ml) and aqueous 20% HCl (6 ml) following the procedure described in Example 31, Step B, giving (E)-3-[1'-(4-fluoro-benzyl)-4-oxo-spiro(chromane-2,3'-azetidine)-6-yl]-acrylic acid (300 mg, hydrochloride salt) as a pale yellow solid.

Y=79%

LC-MS: (ES+) MH$^+$: 368

$^1$H NMR (300 MHz, DMSO-d$_6$) δ (ppm) 12.38 (bs, 1H), 11.38 (bs, 1H), 7.95-8.07 (m, 2H), 7.61 (d, J=16.14 Hz, 1H), 7.54-7.63 (m, 2H), 7.13-7.34 (m, 3H), 6.49 (d, J=15.85 Hz, 1H), 3.99-4.66 (m, 6H), 3.35-3.67 (m, 2H).

Step C

A suspension of (E)-3-[1'-(4-fluoro-benzyl)-4-oxo-spiro(chromane-2,3'-azetidine)-6-yl]-acrylic acid (300 mg, 0.74 mmol) in DCM (9 ml) was treated with TEA (0.17 ml, 1.2 mmol) and then with EDC (235 mg, 1.23 mmol), HOBt (166 mg, 1.23 mmol) and NH$_2$OTHP (115 mg, 0.982 mmol) following the procedure described in Example 30, Step B, giving (E)-3-[1'-(4-fluoro-benzyl)-4-oxo-spiro(chromane-2,3'-azetidine)-6-yl]-N-(tetrahydro-pyran-2-yloxy)-acrylamide (280 mg) as a light yellow solid.

Y=81%

LC-MS: (ES+) MH$^+$: 467

$^1$H NMR (300 MHz, DMSO-d$_6$) δ (ppm) 11.12 (bs, 1H), 7.90 (d, J=2.05 Hz, 1H), 7.81 (d, J=8.51 Hz, 1H), 7.47 (d, J=15.85 Hz, 1H), 7.26-7.37 (m, 2H), 7.17 (d, J=8.51 Hz, 1H), 7.05-7.15 (m, 2H), 6.48 (d, J=14.97 Hz, 1H), 4.90 (bs, 1H), 3.75-4.11 (m, 1H), 3.65 (s, 2H), 3.45-3.59 (m, 1H), 3.36 (d, J=8.51 Hz, 2H), 3.23 (d, J=8.51 Hz, 2H), 3.13 (s, 2H), 1.26-1.88 (m, 6H).

Step D (E)-3-[1'-(4-Fluoro-benzyl)-4-oxo-spiro(chromane-2,3'-azetidine)-6-yl]-N-(tetrahydro-pyran-2-yloxy)-acrylamide (260 mg, 0.56 mmol) in DCM (10 ml) was treated with 4 M HCl in dioxane (1 ml) as described in Example 30, Step C, giving (E)-3-[1'-(4-fluoro-benzyl)-4-oxo-spiro(chromane-2, 3'-azetidine)-6-yl]-N-hydroxy-acrylamide (143 mg, hydrochloride salt) as as a light yellow solid.

Y=61%, purity 95.3%

LC-MS: Method H, rt=1.04; (ES+) MH$^+$: 382

$^1$H NMR (300 MHz, DMSO-d$_6$) δ (ppm) 11.21-11.83 (m, 1H), 10.72 (bs, 1H), 7.91 (d, J=2.05 Hz, 1H), 7.79-7.88 (m, 1H) 7.53-7.72 (m, 2H), 7.46 (d, J=15.85 Hz, 1H), 7.23-7.37 (m, 2H), 7.10-7.22 (m, 1H), 6.46 (d, J=15.85 Hz, 1H), 4.12-4.54 (m, 6H), 3.14-3.49 (m, 2H).

Example 34

(E)-3-[1'-Methyl-4-oxo-spiro(chromane-2,3'-azetidine)-6-yl]-N-hydroxy-acrylamide

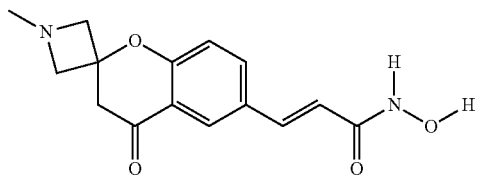 [SMILES: CN1CC2(CC(=O)c3cc(/C=C/C(=O)NO)ccc3O2)C1]

Step A (E)-3-[1'-Methyl-4-oxo-spiro(chromane-2,3'-azetidine)-6-yl]-acrylic acid methyl ester was synthesized starting from Intermediate 4 (500 mg, 1.62 mmol), according to the procedure for preparation of Example 31, Step A, using aqueous 37% formaldehyde solution (0.088 ml, 3.2 mmol), and NaBH(OAc)$_3$ (515 mg, 2.43 mmol). The product was obtained as pale yellow oil (430 mg).

Y=92%

LC-MS: (ES+) MH$^+$: 288

$^1$H NMR (300 MHz, DMSO-d$_6$) δ (ppm) 7.84-8.12 (m, 2H), 7.67 (d, J=16.14 Hz, 1H), 7.16 (d, J=8.80 Hz, 1H), 6.58 (d, J=16.14 Hz, 1H), 3.72 (s, 3H), 3.37 (d, J=8.80 Hz, 2H), 3.15 (d, J=8.80 Hz, 2H), 3.11 (s, 2H), 2.30 (s, 3H).

Step B (E)-3-[1'-Methyl-4-oxo-spiro(chromane-2,3'-azetidine)-6-yl]-acrylic acid methyl ester (410 mg, 1.53 mmol) was hydrolyzed with AcOH (10 ml) and aqueous 20% HCl (10 ml) following the procedure described in Example 31, Step B, giving (E)-3-[1'-methyl-4-oxo-spiro(chromane-2,3'-azetidine)-6-yl]-acrylic acid (400 mg, hydrochloride salt) as a pale yellow oil.

Y=85%

LC-MS: (ES+) MH$^+$: 274

$^1$H NMR (300 MHz, DMSO-d$_6$) δ (ppm) 12.38 (bs, 1H), 10.98 (bs, 1H), 8.04 (dd, J=8.80, 2.35 Hz, 1H), 7.99 (d, J=2.05 Hz, 1H), 7.62 (d, J=16.14 Hz, 1H), 7.21 (d, J=8.51 Hz, 1H), 6.50 (d, J=16.14 Hz, 1H), 4.17-4.50 (m, 4H), 3.35 (s, 2H), 2.90 (bs, 3H).

Step C

A suspension of (E)-3-[1'-methyl-4-oxo-spiro(chromane-2,3'-azetidine)-6-yl]-acrylic acid (400 mg, 1.29 mmol) in DCM (16 ml) was treated with TEA (0.30 ml, 2.2 mmol) and then with EDC (420 mg, 2.20 mmol), HOBt (297 mg, 2.20 mmol) and NH$_2$OTHP (204 mg, 1.75 mmol) following the procedure described in Example 30, Step B, giving (E)-3-[1'-methyl-4-oxo-spiro(chromane-2,3'-azetidine)-6-yl]-N-(tetrahydro-pyran-2-yloxy)-acrylamide (340 mg) as a light yellow solid.

Y=71%

LC-MS: (ES+) MH$^+$: 373

$^1$H NMR (300 MHz, DMSO-d$_6$) δ (ppm) 11.12 (bs, 1H), 7.90 (d, J=2.35 Hz, 1H), 7.69-7.86 (m, 1H), 7.48 (d, J=15.85 Hz, 1H), 7.16 (d, J=8.80 Hz, 1H), 6.48 (d, J=15.85 Hz, 1H), 4.91 (bs, 1H), 3.80-4.10 (m, 1H), 3.45-3.63 (m, 1H), 3.37 (d, J=8.51 Hz, 2H), 3.15 (d, J=8.80 Hz, 2H), 3.11 (s, 2H), 2.30 (s, 3H), 1.41-1.89 (m, 6H).

Step D (E)-3-[1'-Methyl-4-oxo-spiro(chromane-2,3'-azetidine)-6-yl]-N-(tetrahydro-pyran-2-yloxy)-acrylamide (320 mg, 0.86 mmol) in DCM (4 ml) was treated with 1 M HCl in Et$_2$O (4 ml) as described in Example 31, Step C, giving (E)-3-[1'-methyl-4-oxo-spiro(chromane-2,3'-azetidine)-6-yl]-N-hydroxy-acrylamide (209 mg, hydrochloride salt) as a white solid.

Y=75%, purity 98%

LC-MS: Method E, rt=2.00; (ES+) MH$^+$: 288

$^1$H NMR (300 MHz, DMSO-d$_6$) δ (ppm) 10.88 (bs, 1H), 10.72 (bs, 1H), 9.02 (bs, 1H), 7.92 (d, J=2.05 Hz, 1H), 7.86 (dd, J=8.80, 2.05 Hz, 1H), 7.46 (d, J=15.85 Hz, 1H), 7.22 (d, J=8.80 Hz, 1H), 6.46 (d, J=15.85 Hz, 1H), 4.17-4.50 (m, 4H), 3.33 (s, 2H), 2.92 (bs, 3H).

Example 35

(E)-3-{1'-[2-(4-Fluoro-phenyl)-ethyl]-4-oxo-spiro(chromane-2,3'-azetidine)-6-yl}-N-hydroxy-acrylamide

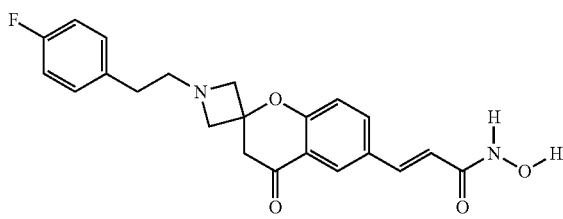 [SMILES: O=C(/C=C/c1ccc2c(c1)C(=O)CC1(CN(CCc3ccc(F)cc3)C1)O2)NO]

Step A

K$_2$CO$_3$ (285 mg, 2.06 mmol) and 1-(2-bromoethyl)-4-fluorobenzene (0.43 ml, 3.1 mmol) were added to a suspension of Intermediate 4 (320 mg, 1.04 mmol) in acetonitrile (30 ml) and the mixture was stirred at 70° C. for 54 h. The solvent was evaporated and the residue was partitioned between water and DCM. The organic phase was dried over Na$_2$SO$_4$, filtered and evaporated. The crude residue was purified by column chromatography on silica gel (eluent:petroleum ether:EtOAc 6:4) to give (E)-3-{1'-[2-(4-fluoro-phenyl)-ethyl]-4-oxo-spiro(chromane-2,3'-azetidine)-6-yl}-acrylic acid methyl ester (120 mg) as a brown oil.

Y=30%

LC-MS: (ES+) MH$^+$: 396

$^1$H NMR (300 MHz, Chloroform-d) δ (ppm) 8.03 (d, J=2.35 Hz, 1H), 7.68 (dd, J=8.51, 2.35 Hz, 1H), 7.65 (d, J=15.26 Hz, 1H), 7.12-7.24 (m, 2H), 7.08 (d, J=8.51 Hz, 1H), 6.94-7.04 (m, 2H), 6.40 (d, J=16.14 Hz, 1H), 3.82 (s, 3H), 3.27-3.71 (m, 4H) 3.15 (bs, 2H), 2.49-3.03 (m, 4H).

Step B (E)-3-{1'-[2-(4-Fluoro-phenyl)-ethyl]-4-oxo-spiro(chromane-2,3'-azetidine)-6-yl}-acrylic acid methyl ester (120 mg, 0.30 mmol) was hydrolyzed in AcOH (10 ml) and 20% aqueous HCl solution (10 ml) following the procedure described in Example 31, Step B, giving (E)-3-{1'-[2-(4-fluoro-phenyl)-ethyl]-4-oxo-spiro(chromane-2,3'-azetidine)-6-yl}-acrylic acid as a yellow solid. [LC-MS: (ES+) MH$^+$: 382]. The obtained acid was suspended in DCM (5 ml), treated with TEA (0.06 ml, 0.4 mmol) and then with EDC (86 mg, 0.45 mmol), HOBt (61 mg, 0.45 mmol) and NH$_2$OTHP (42 mg, 0.36 mmol) following the procedure described in Example 30, Step B, giving (E)-3-{1'-[2-(4-fluoro-phenyl)-ethyl]-4-oxo-spiro(chromane-2,3'-azetidine)-6-yl}-N-(tetrahydro-pyran-2-yloxy)-acrylamide (88 mg) as a light yellow solid.

Y=61% over 2 steps

LC-MS: (ES+) MH$^+$: 481

$^1$H NMR (300 MHz, DMSO-d$_6$) δ (ppm) 11.13 (bs, 1H), 7.91 (d, J=2.05 Hz, 1H), 7.72-7.87 (m, 1H), 7.48 (d, J=16.14 Hz, 1H), 7.20-7.30 (m, 2H), 7.16 (d, J=8.51 Hz, 1H), 6.98-7.13 (m, 2H), 6.48 (d, J=15.85 Hz, 1H), 4.91 (bs, 1H), 3.85-4.03 (m, 1H), 3.51-3.60 (m, 1H), 3.37 (d, J=8.80 Hz, 2H), 3.18 (d, J=8.51 Hz, 2H), 3.10 (s, 2H), 2.63-2.74 (m, 2H), 2.54-2.60 (m, 2H), 1.37-1.77 (m, 6H).

Step C (E)-3-{1'-[2-(4-Fluoro-phenyl)-ethyl]-4-oxo-spiro(chromane-2,3'-azetidine)-6-yl}-N-(tetrahydro-pyran-2-yloxy)-acrylamide (85 mg, 0.18 mmol) in DCM (8 ml) was treated with 4 M HCl in dioxane (1 ml) as described in Example 30, Step C, giving (E)-3-{1'-[2-(4-fluoro-phenyl)-ethyl]-4-oxo-spiro(chromane-2,3'-azetidine)-6-yl}-N-hydroxy-acrylamide (65 mg, hydrochloride salt) as as a light brown solid.

Y=83%, purity 87%

LC-MS: Method C, rt=3.40; (ES+) MH$^+$: 397

$^1$H NMR (300 MHz, DMSO-d$_6$) δ (ppm) 11.17 (bs, 1H), 10.72 (bs, 1H), 7.92 (d, J=2.05 Hz, 1H), 7.76-7.90 (m, 1H), 7.47 (d, J=15.85 Hz, 1H), 7.26-7.40 (m, 2H), 7.03-7.25 (m, 3H), 6.47 (d, J=16.14 Hz, 1H), 4.02-4.56 (m, 4H), 3.16-3.48 (m, 4 H), 2.76-2.94 (m, 2H).

Example 36

(E)-3-[1'Acetyl-4-oxo-spiro(chromane-2,3'-azetidine)-6-yl]-N-hydroxy-acrylamide

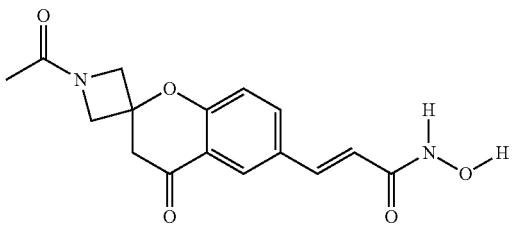 [SMILES: CC(=O)N1CC2(CC(=O)c3cc(/C=C/C(=O)NO)ccc3O2)C1]

Step A

A suspension of Intermediate 4 (280 mg, 0.90 mmol) in DCM (7.5 ml) was treated with DIPEA (0.32 ml, 1.8 mmol) and acetyl chloride (0.09 ml, 1.35 mmol). The reaction mixture was stirred at RT for 1 h and the solution was then evaporated under vacuum to give (E)-3-[1'-acetyl-4-oxo-spiro(chromane-2,3'-azetidine)-6-yl]-acrylic acid methyl ester as a light brown solid (280 mg).

Y=99%

LC-MS: (ES+) MH$^+$: 316

$^1$H NMR (300 MHz, DMSO-d$_6$) δ (ppm) 7.93-8.09 (m, 2H), 7.69 (d, J=16.14 Hz, 1H), 7.22 (d, J=8.80 Hz, 1H), 6.61 (d, J=15.85 Hz, 1H), 4.10-4.34 (m, 2H), 3.83-4.05 (m, 2H), 3.72 (s, 3H), 3.22 (s, 2H), 1.78 (s, 3H).

Step B (E)-3-[1'-Acetyl-4-oxo-spiro(chromane-2,3'-azetidine)-6-yl]-acrylic acid methyl ester (270 mg, 0.85 mmol) was hydrolyzed with 1 M NaOH (1.1 ml) following the procedure described in Example 30, Step A, giving (E)-3-[1'-acetyl-4-oxo-spiro(chromane-2,3'-azetidine)-6-yl]-acrylic acid (120 mg, hydrochloride salt) as a brown solid.

Y=42%

LC-MS: (ES+) MH⁺: 302

$^1$H NMR (300 MHz, DMSO-d$_6$) δ (ppm) 12.33 (bs, 1H), 8.01 (dd, J=8.80, 2.35 Hz, 1H), 7.98 (d, J=2.05 Hz, 1H), 7.61 (d, J=15.85 Hz, 2H), 7.21 (d, J=8.51 Hz, 1H), 6.49 (d, J=16.14 Hz, 1H), 4.14-4.33 (m, 2H), 3.87-4.05 (m, 2H), 3.22 (s, 2H), 1.78 (s, 3H).

Step C

A suspension of (E)-3-[1'-acetyl-4-oxo-spiro(chromane-2,3'-azetidine)-6-yl]-acrylic acid (100 mg, 0.30 mmol) in DCM (3 ml) was treated with TEA (0.060 ml, 0.49 mmol) and then with EDC (94 mg, 0.49 mmol), HOBt (67 mg, 0.49 mmol) and NH$_2$OTHP (50 mg, 0.43 mmol) following the procedure described in Example 30, Step B, giving (E)-3-[1'-acetyl-4-oxo-spiro(chromane-2,3'-azetidine)-6-yl]-N-(tetrahydro-pyran-2-yloxy)-acrylamide (36 mg) as a white solid.

Y=30%

LC-MS: (ES+) MH⁺: 401

$^1$H NMR (300 MHz, DMSO-d$_6$) δ (ppm) 11.14 (bs, 1H), 7.94 (d, J=2.05 Hz, 1H), 7.80-7.88 (m, 1H), 7.50 (d, J=15.85 Hz, 1H), 7.22 (d, J=8.51 Hz, 1H), 6.50 (d, J=15.85 Hz, 1H), 4.91 (bs, 1H), 4.10-4.33 (m, 2H), 3.85-4.06 (m, 3H), 3.47-3.65 (m, 1H), 3.22 (s, 2H), 1.78 (s, 3H), 1.46-1.75 (m, 6H).

Step D (E)-3-[1'-Acetyl-4-oxo-spiro(chromane-2,3'-azetidine)-6-yl]-N-(tetrahydro-pyran-2-yloxy)-acrylamide (35 mg, 0.088 mmol) in DCM (5 ml) was treated with 4 M HCl in dioxane (0.4 ml) as described in Example 30, Step C, giving (E)-3-[1'-acetyl-4-oxo-spiro(chromane-2,3'-azetidine)-6-yl]-N-hydroxy-acrylamide (27 mg, hydrochloride salt) as a light brown solid.

Y=85%, purity 90%

LC-MS: Method C, rt=2.75; (ES+) MH⁺: 317

$^1$H NMR (300 MHz, DMSO-d$_6$) δ (ppm) 10.68 (bs, 1H), 7.92 (d, J=2.05 Hz, 1H), 7.75-7.89 (m, 1H), 7.46 (d, J=15.85 Hz, 1H), 7.21 (d, J=8.51 Hz, 1H), 6.45 (d, J=16.14 Hz, 1H), 4.10-4.34 (m, 2H), 3.79-4.02 (m, 2H), 3.16-3.30 (m, 2H), 1.79 (s, 3H).

Example 37

(E)-3-[1'-Benzoyl-4-oxo-spiro(chromane-2,3'-azetidine)-6-yl]-N-hydroxy-acrylamide

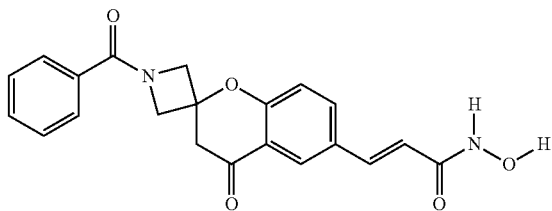 [SMILES: O=C(/C=C/c1ccc2c(c1)C(=O)CC1(CN(C(=O)c3ccccc3)C1)O2)NO]

Step A

A suspension of Intermediate 4 (280 mg, 0.90 mmol) in DCM (7.5 ml) was treated with benzoyl chloride (0.16 ml, 1.4 mmol) and DIPEA (0.32 ml, 1.8 mmol) as described in Example 36, Step A, giving (E)-3-[1'-benzoyl-4-oxo-spiro(chromane-2,3'-azetidine)-6-yl]-acrylic acid methyl ester as a white solid (330 mg).

Y=97%

LC-MS: (ES+) MH⁺: 378

$^1$H NMR (300 MHz, DMSO-d$_6$) δ (ppm) 8.04 (dd, J=8.51, 2.35 Hz, 1H), 8.02 (d, J=2.35 Hz, 1H), 7.63-7.76 (m, 3H), 7.38-7.56 (m, 3H), 7.23 (d, J=8.51 Hz, 1H), 6.60 (d, J=16.14 Hz, 1H), 4.06-4.57 (m, 4H), 3.72 (s, 3H), 3.27 (s, 2H).

Step B (E)-3-[1'-Benzoyl-4-oxo-spiro(chromane-2,3'-azetidine)-6-yl]-acrylic acid methyl ester (380 mg, 1.0 mmol) was hydrolyzed with 1 M NaOH following the procedure described in Example 30, Step A, giving (E)-3-[1'-benzoyl-4-oxo-spiro(chromane-2,3'-azetidine)-6-yl]-acrylic acid (220 mg, hydrochloride salt) as a light brown solid.

Y=55%

LC-MS: (ES+) MH⁺: 364

$^1$H NMR (300 MHz, DMSO-d$_6$) δ (ppm) 12.38 (bs, 1H), 8.01 (dd, J=8.51, 2.05 Hz, 1H), 7.97 (d, J=2.05 Hz, 1H), 7.64-7.70 (m, 2H), 7.61 (d, J=15.85 Hz, 1H), 7.39-7.56 (m, 3H), 7.23 (d, J=8.51 Hz, 1H), 6.48 (d, J=15.85 Hz, 1H), 4.33-4.60 (m, 2H), 3.99-4.33 (m, 2H), 3.27 (s, 2H).

Step C

A suspension of (E)-3-[1'-benzoyl-4-oxo-spiro(chromane-2,3'-azetidine)-6-yl]-acrylic acid (200 mg, 0.50 mmol) in DCM (5 ml) was treated with TEA (0.11 ml, 0.82 mmol) and then with EDC (158 mg, 0.827 mmol), HOBt (107 mg, 0.793 mmol) and NH$_2$OTHP (74 mg, 0.63 mmol) following the procedure described in Example 30, Step B, giving (E)-3-[1'-benzoyl-4-oxo-spiro(chromane-2,3'-azetidine)-6-yl]-N-(tetrahydro-pyran-2-yloxy)-acrylamide (120 mg) as a light yellow solid.

Y=52%

LC-MS: (ES+) MH⁺: 463

$^1$H NMR (300 MHz, DMSO-d$_6$) δ (ppm) 11.14 (bs, 1H), 7.93 (d, J=2.35 Hz, 1H), 7.85 (d, J=8.80 Hz, 1H), 7.60-7.70 (m, 2H), 7.37-7.56 (m, 4H), 7.23 (d, J=8.51 Hz, 1H), 6.50 (d, J=16.14 Hz, 1H), 4.91 (bs, 1H), 3.79-4.61 (m, 5H), 3.45-3.65 (m, 1H), 3.27 (s, 2H), 1.39-1.83 (m, 6H).

Step D (E)-3-[1'-Benzoyl-4-oxo-spiro(chromane-2,3'-azetidine)-6-yl]-N-(tetrahydro-pyran-2-yloxy)-acrylamide (110 mg, 0.23 mmol) in DCM (8 ml) was treated with 4 M HCl in dioxane (1 ml) as described in Example 30, Step C, giving (E)-3-[1'-benzoyl-4-oxo-spiro(chromane-2,3'-azetidine)-6-yl]-N-hydroxy-acrylamide (62 mg, hydrochloride salt) as a as a pale yellow solid.

Y=65%, purity 95%

LC-MS: Method C, rt=3.71; (ES+) MH⁺: 379

$^1$H NMR (300 MHz, DMSO-d$_6$) δ (ppm) 10.67 (s, 1H), 9.01 (bs, 1H), 7.92 (d, J=2.05 Hz, 1H), 7.83 (dd, J=8.95, 1.91 Hz, 1H), 7.60-7.70 (m, 2H), 7.38-7.58 (m, 4H), 7.23 (d, J=8.51 Hz, 1H), 6.44 (d, J=15.85 Hz, 1H), 3.80-4.75 (m, 4H), 3.26 (s, 2H).

Example 38

(E)-3-[1'-Ethyloxycarbonyl-4-oxo-spiro(chromane-2,3'-azetidine)-6-yl]-N-hydroxy-acrylamide

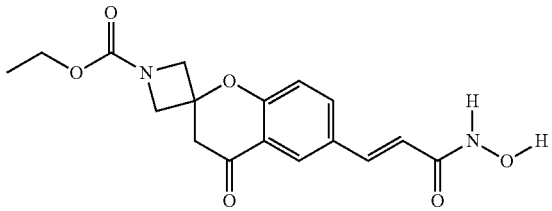 [SMILES: CCOC(=O)N1CC2(CC(=O)c3cc(/C=C/C(=O)NO)ccc3O2)C1]

Step A

A suspension of Intermediate 4 (280 mg, 0.90 mmol) in DCM (7.5 ml) was treated with ethyl chloroformate (0.13 ml, 1.4 mmol) and DIPEA (0.32 ml, 1.8 mmol) as described in Example 36, Step A, giving (E)-3-[1'-ethyloxycarbonyl-4-oxo-spiro(chromane-2,3'-azetidine)-6-yl]-acrylic acid methyl ester as a light brown solid (310 mg).

Y=100%

LC-MS: (ES+) MH+: 346

$^1$H NMR (300 MHz, DMSO-$d_6$) δ (ppm) 8.03 (dd, J=8.51, 2.35 Hz, 1H), 8.01 (d, J=2.05 Hz, 1H), 7.69 (d, J=16.14 Hz, 1H), 7.21 (d, J=8.51 Hz, 1H), 6.60 (d, J=16.14 Hz, 1H), 4.07 (d, J=9.39 Hz, 2H), 4.03 (q, J=7.34 Hz, 2H), 3.97 (d, J=8.51 Hz, 2H), 3.72 (s, 3H), 3.22 (s, 2H), 1.16 (t, J=7.04 Hz, 3H).

Step B (E)-3-[1'-Ethyloxycarbonyl-4-oxo-spiro(chromane-2,3'-azetidine)-6-yl]-acrylic acid methyl ester (300 mg, 0.86 mmol) was hydrolyzed with 1 M NaOH following the procedure described in Example 30, Step A, giving (E)-3-[1'-ethyloxycarbonyl-4-oxo-spiro(chromane-2,3'-azetidine)-6-yl]-acrylic acid (200 mg, hydrochloride salt) as a yellow solid.

Y=62%

LC-MS: (ES+) MH+: 332

$^1$H NMR (300 MHz, DMSO-$d_6$) δ (ppm) 12.32 (bs, 1H), 8.00 (dd, J=8.51, 2.35 Hz, 1H), 7.96 (d, J=2.05 Hz, 1H), 7.60 (d, J=16.14 Hz, 1H), 7.21 (d, J=8.51 Hz, 1H), 6.48 (d, J=16.14 Hz, 1H), 4.07 (d, J=9.39 Hz, 2H), 4.03 (q, J=7.04 Hz, 2H), 3.96 (d, J=9.68 Hz, 2H), 3.22 (s, 2H), 1.16 (t, J=7.04 Hz, 3H).

Step C (E)-3-[1'-Ethyloxycarbonyl-4-oxo-spiro(chromane-2,3'-azetidine)-6-yl]-acrylic acid (200 mg, 0.54 mmol) in DCM (5 ml) was treated with TEA (0.12 ml, 0.90 mmol) and then with EDC (172 mg, 0.900 mmol), HOBt (121 mg, 0.896 mmol) and NH$_2$OTHP (84 mg, 0.72 mmol) following the procedure described in Example 30, Step B, giving (E)-3-[1'-ethyloxycarbonyl-4-oxo-spiro(chromane-2,3'-azetidine)-6-yl]-N-(tetrahydro-pyran-2-yloxy)-acrylamide (140 mg) as a light yellow solid.

Y=60%

LC-MS: (ES+) MH+: 431

$^1$H NMR (300 MHz, DMSO-$d_6$) δ (ppm) 11.14 (bs, 1H), 7.93 (d, J=2.05 Hz, 1H), 7.84 (d, J=9.10 Hz, 1H), 7.50 (d, J=15.85 Hz, 1H), 7.22 (d, J=8.80 Hz, 1H), 6.50 (d, J=16.43 Hz, 1H), 4.91 (bs, 1H), 4.05-4.15 (m, 2H), 4.03 (q, J=7.04 Hz, 2H), 3.85-3.99 (m, 3H), 3.49-3.61 (m, 1H), 3.22 (s, 2H), 1.40-1.79 (m, 6H), 1.16 (t, J=7.04 Hz, 3H).

Step D (E)-3-[1'-Ethyloxycarbonyl-4-oxo-spiro(chromane-2,3'-azetidine)-6-yl]-N-(tetrahydro-pyran-2-yloxy)-acrylamide (110 mg, 0.26 mmol) in DCM (8 ml) was treated with 4 M HCl in dioxane (1 ml) as described in Example 30, Step C, giving (E)-3-[1'-ethyloxycarbony-4-oxo-spiro(chromane-2,3'-azetidine)-6-yl]-N-hydroxy-acrylamide (54 mg, hydrochloride salt) as a white solid.

Y=54%, purity 92%

LC-MS: Method C, rt=3.63; (ES+) MH+: 347

$^1$H NMR (300 MHz, DMSO-$d_6$) δ (ppm) 10.68 (bs, 1H), 7.91 (d, J=2.05 Hz, 1H), 7.82 (dd, J=8.66, 1.91 Hz, 1H), 7.45 (d, J=15.85 Hz, 1H), 7.21 (d, J=8.51 Hz, 1H), 6.44 (d, J=15.55 Hz, 1H), 4.07 (d, J=9.39 Hz, 2H), 4.03 (q, J=7.04 Hz, 2H), 3.96 (d, J=9.39 Hz, 2H), 3.22 (s, 2H), 1.16 (t, J=7.04 Hz, 3H).

Example 39

(±)-(E)-3-{3,4-Dihydro-4-oxo-spiro[2H-(1,3)-benzoxazine-2,3'-piperidin]-6-yl}-N-hydroxy-acrylamide

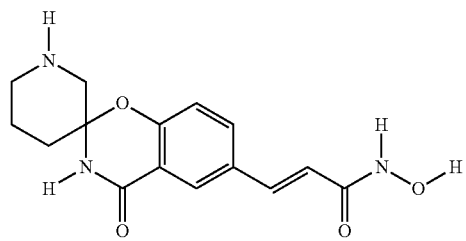 [SMILES: O=C(/C=C/c1ccc2c(c1)C(=O)NC1(CCCNC1)O2)NO]

Step A

A solution of (±)-(E)-3-{1'-tert-butoxycarbonyl-3,4-dihydro-4-oxo-spiro[2H-(1,3)-benzoxazine-2,3'-piperidin]-6-yl}-acrylic acid methyl ester (Intermediate 5, Step B, 270 mg, 0.67 mmol) in water (3 ml) and dioxane (6 ml) was treated with 1 M NaOH (0.75 ml) as described in Example 30, Step A to give (±)-(E)-3-{1'-tert-butoxycarbonyl-3,4-dihydro-4-oxo-spiro[2H-(1,3)-benzoxazine-2,3'-piperidin]-6-yl}-acrylic acid (240 mg) as a yellow solid.

Y=92%

LC-MS: (ES+) MH+-56: 333

$^1$H NMR (300 MHz, DMSO-$d_6$) δ (ppm): 10.82 (bs, 1H), 8.10 (d, J=2.05 Hz, 1H), 7.85-7.99 (m, 1H), 7.72 (d, J=16.14 Hz, 1H), 6.91-7.25 (m, 1H), 6.52 (d, J=16.14 Hz, 1H), 4.13-4.33 (m, 1H), 3.84-4.00 (m, 1H), 2.63-3.36 (m, 2H), 2.14-2.31 (m, 1H), 1.66-2.01 (m, 3H), 1.26 (bs, 9H).

Step B

A suspension of (±)-(E)-3-{1'-tert-butoxycarbonyl-3,4-dihydro-4-oxo-spiro[2H-(1,3)-benzoxazine-2,3'-piperidin]-6-yl}-acrylic acid (220 mg, 0.57 mmol) in DCM (5 ml) was treated with TEA (0.12 ml, 0.90 mmol) and then with EDC (162 mg, 0.848 mmol), HOBt (114 mg, 0.844 mmol) and NH$_2$OTHP (78 mg, 0.67 mmol) following the procedure described in Example 30, Step B, giving (±)-(E)-3-{t-tert-butoxycarbonyl-3,4-dihydro-4-oxo-spiro[2H-(1,3)-benzoxazine-2,3'-piperidin]-6-yl}-N-(tetrahydro-pyran-2-yloxy)-acrylamide (100 mg) as a light yellow solid.

Y=37%

LC-MS: (ES+) MH+: 488

$^1$H NMR (300 MHz, DMSO-$d_6$) δ (ppm): 11.13 (bs, 1H), 8.86 (bs, 1H), 7.96 (d, J=1.47 Hz, 1H), 7.69-7.83 (m, 1H), 7.49 (d, J=15.85 Hz, 1H), 6.77-7.14 (m, 1H), 6.49 (d, J=15.85 Hz, 1H), 4.91 (bs, 1H), 3.89-4.21 (m, 2H), 3.69-3.85 (m, 1H), 3.46-3.66 (m, 1H), 2.78-3.17 (m, 2H), 2.02-2.18 (m, 1H), 1.79-1.94 (m, 1H), 1.30-1.78 (m, 8H), 1.16 (bs, 9H).

Step C

A solution of (±)-(E)-3-{1'-tert-butoxycarbonyl-3,4-dihydro-4-oxo-spiro[2H-(1,3)-benzoxazine-2,3'-piperidin]-6-yl}-N-(tetrahydro-pyran-2-yloxy)-acrylamide (360 mg, 0.74 mmol) in DCM (14 ml) was treated with 4 M HCl in dioxane (1.9 ml) as described in Example 30, STEP C to give (±)-(E)-3-{3,4-dihydro-4-oxo-spiro[2H-(1,3)-benzoxazine-2,3'-piperidin]-6-yl}-N-hydroxy-acrylamide (154 mg, hydrochloride salt) as a white solid.

Y=61%, purity=95%

LC-MS: Method C rt=2.26; (ES+) MH⁺: 304

¹H NMR (300 MHz, DMSO-d₆) δ (ppm): 10.72 (bs, 1H), 9.44 (d, J=9.68 Hz, 1H), 9.03 (s, 1H), 8.71-8.95 (m, 1H), 7.95 (d, J=2.05 Hz, 1H), 7.77 (dd, J=8.51, 2.05 Hz, 1H), 7.46 (d, J=16.14 Hz, 1H), 7.17 (d, J=8.51 Hz, 1H), 6.46 (d, J=15.85 Hz, 1H), 3.59-3.65 (m, 1H), 3.12-3.29 (m, 1H), 2.82-3.12 (m, 2H), 2.07-2.23 (m, 1H), 1.77-2.07 (m, 3H).

Example 40

(±)-(E)-3-{1'-Benzyl-3,4-dihydro-4-oxo-spiro[2H-(1,3)-benzoxazine-2,3'-piperidin]-6-yl}-N-hydroxy-acrylamide

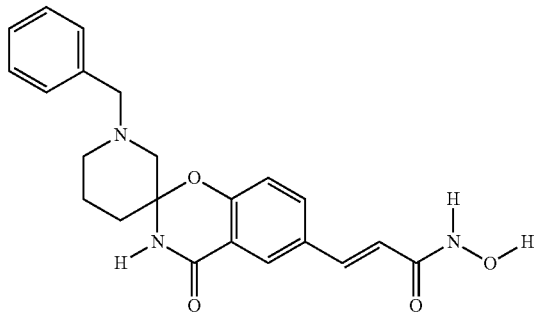 [SMILES: O=C(/C=C/c1ccc2c(c1)C(=O)NC1(CCCN(Cc3ccccc3)C1)O2)NO]

Step A 0.5 M NaOH in MeOH (0.8 ml) was added to a suspension of (±)-(E)-3-{3,4-dihydro-4-oxo-spiro[2H-(1,3)-benzoxazine-2,3'-piperidin]-6-yl}-acrylic acid methyl ester (280 mg, 0.83 mmol, Intermediate 5, hydrochloride salt) in MeOH (5 ml) and the mixture was stirred for 10 min. The resulting clear solution was treated with benzaldehyde (0.10 ml, 0.99 mmol) and NaBH₃CN (63 mg, 1.0 mmol), and stirred at RT for 2 h. The reaction mixture was evaporated to dryness, diluted with water and the product extracted with DCM (3 times 10 ml). The combined organic layers were dried over Na₂SO₄, filtered and evaporated to give the (±)-(E)-3-{1'-benzyl-3,4-dihydro-4-oxo-spiro[2H-(1,3)-benzoxazine-2,3'-piperidin]-6-yl}-acrylic acid methyl ester (257 mg) as a brown solid.

Y=79%

LC-MS: (ES+) MH⁺: 393

¹H NMR (300 MHz, DMSO-d₆) δ (ppm) 8.69 (s, 1H), 7.94 (d, J=2.05 Hz, 1H), 7.92 (dd, J=8.51, 2.35 Hz, 1H), 7.66 (d, J=16.14 Hz, 1H), 7.00-7.43 (m, 6H), 6.55 (d, J=16.14 Hz, 1H), 3.72 (s, 3H), 3.57 (d, J=13.79 Hz, 1H), 3.40 (d, J=13.79 Hz, 1H), 2.77-2.88 (m, 1H), 2.55-2.68 (m, 1H), 2.14-2.25 (m, 2H), 1.52-2.02 (m, 4H).

Step B

A solution of (±)-(E)-3-{1'-benzyl-3,4-dihydro-4-oxo-spiro[2H-(1,3)-benzoxazine-2,3'-piperidin]-6-yl}-acrylic acid methyl ester (240 mg, 0.61 mmol) in water (5 ml) and dioxane (10 ml) was treated with 1 M NaOH (0.80 ml) as described in Example 30, Step A, to give (±)-(E)-3-{1'-benzyl-3,4-dihydro-4-oxo-spiro[2H-(1,3)-benzoxazine-2,3'-piperidin]-6-yl}-acrylic acid (hydrochloride salt, 240 mg) as a brown oil.

Y=95%

LC-MS: (ES+) MH⁺: 379

¹H NMR (300 MHz, DMSO-d₆) δ (ppm) 12.25 (bs, 1H), 8.67 (s, 1H), 7.81-7.92 (m, 2H), 7.57 (d, J=16.14 Hz, 1H), 7.02-7.38 (m, 6H), 6.43 (d, J=16.14 Hz, 1H), 3.57 (d, J=13.50 Hz, 1H), 3.41 (d, J=13.79 Hz, 1H), 2.74-2.93 (m, 1H), 2.56-2.68 (m, 1H), 2.11-2.32 (m, 2H), 1.56-2.08 (m, 4H).

Step C

A suspension of (±)-(E)-3-{1'-benzyl-3,4-dihydro-4-oxo-spiro[2H-(1,3)-benzoxazine-2,3'-piperidin]-6-yl}-acrylic acid (230 mg, 0.55 mmol) in DCM (6 ml) was treated with TEA (0.12 ml, 0.90 mmol) and then with EDC (172 mg, 0.900 mmol), HOBt (121 mg, 0.896 mmol) and NH₂OTHP (84 mg, 0.72 mmol) following the procedure described in Example 30, Step B, giving (±)-(E)-3-{1'-benzyl-3,4-dihydro-4-oxo-spiro[2H-(1,3)-benzoxazine-2,3'-piperidin]-6-yl}-N-(tetrahydro-pyran-2-yloxy)-acrylamide (120 mg) as a light yellow solid.

Y=46%

LC-MS: (ES+) MH⁺: 478

¹H NMR (300 MHz, DMSO-d₆) δ (ppm) 11.13 (bs, 1H), 8.65 (s, 1H), 7.86 (d, J=2.05 Hz, 1H), 7.66-7.78 (m, 1H), 7.46 (d, J=15.85 Hz, 1H), 7.14-7.36 (m, 5H), 7.11 (d, J=8.51 Hz, 1H), 6.46 (d, J=15.85 Hz, 1H), 4.91 (bs, 1H), 3.86-4.03 (m, 1H), 3.57 (d, J=13.50 Hz, 1H), 3.49-3.58 (m, 1H), 3.41 (d, J=13.79 Hz, 1H), 2.82 (d, J=12.03 Hz, 1H), 2.56-2.67 (m, 1H), 2.11-2.27 (m, 1H), 1.37-1.98 (m, 11H).

Step D (±)-(E)-3-{1'-Benzyl-3,4-dihydro-4-oxo-spiro[2H-(1,3)-benzoxazine-2,3'-piperidin]-6-yl}-N-(tetrahydro-pyran-2-yloxy)-acrylamide (120 mg, 0.25 mmol) in DCM (7 ml) was treated with 4 M HCl in dioxane (1.0 ml) as described in Example 30, STEP C to give (±)-(E)-3-{1'-benzyl-3,4-dihydro-4-oxo-spiro[2H-(1,3)-benzoxazine-2,3'-piperidin]-6-yl}-N-hydroxy-acrylamide (80 mg, hydrochloride salt) as a white solid.

Y=75%), purity 97.5%

LC-MS: Method F, rt=1.12; (ES+) MH⁺: 394

¹H NMR (300 MHz, DMSO-d₆) δ (ppm) 10.47 (bs, 1H), 10.21 (s, 1H), 9.02 (s, 1H), 7.85 (s, 1H), 7.71-7.82 (m, 1H), 7.18-7.61 (m, 7H), 6.44 (d, J=15.55 Hz, 1H), 4.30-4.52 (m, 1H), 4.16-4.30 (m, 1H), 3.29-3.63 (m, 2H), 2.80-3.12 (m, 2H), 2.04-2.31 (m, 2H), 1.60-2.04 (m, 2H).

Example 41

(±)-(E)-3-{1-Methyl-3,4-dihydro-4-oxo-spiro[2H-(1,3)-benzoxazine-2,3'-piperidin]-6-yl}-N-hydroxy-acrylamide

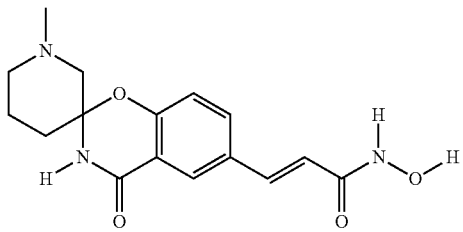 [SMILES: CN1CCCC2(C1)NC(=O)c1cc(/C=C/C(=O)NO)ccc1O2]

Step A (±)-(E)-3-{1'-Methyl-3,4-dihydro-4-oxo-spiro[2H-(1,3)-benzoxazine-2,3'-piperidin]-6-yl}-acrylic acid methyl ester was synthesized starting from Intermediate 5 (300 mg, 0.88 mmol), according to the procedure described in Example 40, Step A, using formaldehyde (0.85 ml, 1.1 mmol) and NaBH₃CN (68 mg, 1.1 mmol). The product was obtained as a white solid (240 mg).

Y=86%

LC-MS: (ES+) MH⁺: 317

¹H NMR (300 MHz, DMSO-d₆) δ (ppm) 8.67 (s, 1H), 8.02 (d, J=2.05 Hz, 1H), 7.89 (dd, J=8.66, 2.20 Hz, 1H), 7.67 (d, J=16.43 Hz, 1H), 7.05 (d, J=8.51 Hz, 1H), 6.56 (d, J=15.85 Hz, 1H), 3.72 (s, 3H), 2.77 (d, J=11.74 Hz, 1H), 2.16-2.26 (m, 1H), 2.12 (s, 3H), 2.01-2.10 (m, 1H), 1.87-1.99 (m, 1H), 1.41-1.83 (m, 4H).

Step B

A solution of (±)-(E)-3-{1'-methyl-3,4-dihydro-4-oxo-spiro[2H-(1,3)-benzoxazine-2,3'-piperidin]-6-yl}-acrylic acid methyl ester (220 mg, 0.70 mmol) in water (8 ml) and dioxane (16 ml) was treated with 1 M NaOH (0.90 ml) as described in Example 30, Step A to give (±)-(E)-3-{1'-methyl-3,4-dihydro-4-oxo-spiro[2H-(1,3)-benzoxazine-2,3'-piperidin]-6-yl}-acrylic acid (208 mg) as a yellow solid.

Y=88%

LC-MS: (ES+) MH⁺: 303

¹H NMR (300 MHz, DMSO-d₆) δ (ppm) 7.54-8.26 (m, 3H), 7.03-7.34 (m, 1H), 6.54 (bs, 1H), 3.74-4.06 (m, 1H), 3.47-3.67 (m, 1H), 3.05-3.27 (m, 2H), 2.92 (s, 3H), 2.15-2.51 (m, 2H), 1.70-2.14 (m, 2H).

Step C

A suspension of (±)-(E)-3-{1'-methyl-3,4-dihydro-4-oxo-spiro[2H-(1,3)-benzoxazine-2,3'-piperidin]-6-yl}-acrylic acid (208 mg, 0.61 mmol) in DCM (7 ml) was treated with TEA (0.14 ml, 1.0 mmol) and then with EDC (196 mg, 1.03 mmol), HOBt (140 mg, 1.03 mmol) and NH₂OTHP (97 mg, 0.82 mmol) following the procedure described in Example 30, Step B, giving (±)-(E)-3-{1'-methyl-3,4-dihydro-4-oxo-spiro[2H-(1,3)-benzoxazine-2,3'-piperidin]-6-yl}-N-(tetrahydro-pyran-2-yloxy)-acrylamide (217 mg) as a light yellow solid.

Y=89%

LC-MS: ES+) MH⁺: 402

¹H NMR (300 MHz, DMSO-d₆) δ (ppm) 11.12 (bs, 1H), 8.64 (s, 1H), 7.94 (d, J=2.05 Hz, 1H), 7.64-7.77 (m, 1H), 7.48 (d, J=16.14 Hz, 1H), 7.05 (d, J=8.51 Hz, 1H), 6.47 (d, J=15.55 Hz, 1H), 4.91 (bs, 1H), 3.83-4.09 (m, 1H), 3.47-3.65 (m, 1H), 2.77 (d, J=12.32 Hz, 1H), 2.22 (d, J=12.03 Hz, 1H), 2.12 (s, 3H), 2.02-2.10 (m, 1H), 1.86-1.98 (m, 1H), 1.46-1.82 (m, 10H).

Step D

A solution of (±)-(E)-3-{1'-methyl-3,4-dihydro-4-oxo-spiro[2H-(1,3)-benzoxazine-2,3'-piperidin]-6-yl}-N-(tetrahydro-pyran-2-yloxy)-acrylamide (210 mg, 0.52 mmol) in DCM (6 ml) was treated with 4 M HCl in dioxane (1.0 ml) as described in Example 30, STEP C to give (±)-(E)-3-{1'-methyl-3,4-dihydro-4-oxo-spiro[2H-(1,3)-benzoxazine-2,3'-piperidin]-6-yl}-N-hydroxy-acrylamide (106 mg, hydrochloride salt) as a yellow solid.

Y=58%, purity 98%

LC-MS: Method C, rt=2.23; (ES+) MH⁺: 318

¹H NMR (300 MHz, DMSO-d₆) δ (ppm) 10.74 (bs, 1H), 10.22 (bs, 1H), 9.15 (s, 1 H), 7.94 (d, J=2.05 Hz, 1H), 7.77 (dd, J=8.51, 1.76 Hz, 1H), 7.46 (d, J=15.85 Hz, 1H), 7.25 (d, J=8.51 Hz, 1H), 6.46 (d, J=15.85 Hz, 1H), 3.79-3.91 (m, 1H), 3.25-3.47 (m, 1H), 3.06 (dd, J=13.06, 10.71 Hz, 1H), 2.88-3.01 (m, 1H), 2.73 (d, J=4.40 Hz, 3H), 1.65-2.23 (m, 4H).

Example 42

(±)-(E)-3-{1'-(4-Fluoro-benzyl)-3,4-dihydro-4-oxo-spiro[2H-(1,3)-benzoxazine-2,3'-piperidin]-6-yl}-N-hydroxy-acrylamide

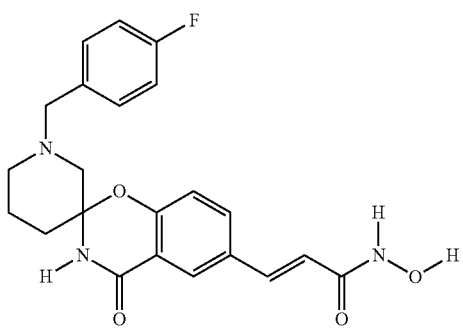 [SMILES: O=C(/C=C/c1ccc2c(c1)C(=O)NC1(CCCN(Cc3ccc(F)cc3)C1)O2)NO]

Step A (±)-(E)-3-{1'-(4-Fluoro-benzyl)-3,4-dihydro-4-oxo-spiro[2H-(1,3)-benzoxazine-2,3'-piperidin]-6-yl}-acrylic acid methyl ester was synthesized starting from Intermediate 5 (339 mg, 1.00 mmol), according to the procedure described in Example 40, Step A, using 4-fluorobenzaldehyde (0.13 ml, 1.2 mmol) and NaBH₃CN (76 mg, 1.2 mmol). The product was obtained as a white solid (320 mg).

Y=78%

LC-MS: (ES+) MH⁺: 411

¹H NMR (300 MHz, DMSO-d₆) δ (ppm) 8.69 (s, 1H), 7.95 (d, J=2.35 Hz, 1H), 7.91 (dd, J=8.22, 2.35 Hz, 1H), 7.66 (d, J=16.43 Hz, 1H), 7.26 (m, 2H), 7.10 (d, J=8.51 Hz, 1H), 6.93-7.06 (m, 2H), 6.55 (d, J=16.14 Hz, 1H), 3.72 (s, 3H), 3.54 (d, J=13.20 Hz, 1H), 3.39 (d, J=13.79 Hz, 1H), 2.79 (d, J=12.91 Hz, 1H), 2.55-2.68 (m, 1H), 2.10-2.33 (m, 2H), 1.56-2.05 (m, 4H).

Step B

A solution of (±)-(E)-3-{1'-(4-fluoro-benzyl)-3,4-dihydro-4-oxo-spiro[2H-(1,3)-benzoxazine-2,3'-piperidin]-6-yl}-acrylic acid methyl ester (300 mg, 0.73 mmol) in water (2.5 ml) and dioxane (5 ml) was treated with 1 M NaOH (0.95 ml) as described in Example 30, Step A to give (±)-(E)-3-{1'-(4-fluoro-benzyl)-3,4-dihydro-4-oxo-spiro[2H-(1,3)-benzoxazine-2,3'-piperidin]-6-yl}-acrylic acid as a white solid [LC-MS: (ES+) MH⁺: 397]. The obtained acrylic acid was suspended in DCM (5 ml), treated with TEA (0.15 ml, 1.1 mmol) and then with EDC (208 mg, 1.09 mmol), HOBt (147 mg, 1.09 mmol) and NH₂OTHP (102 mg, 0.87 mmol) following the procedure described in Example 30, Step B, giving (±)-(E)-3-{t-(4-fluoro-benzyl)-3,4-dihydro-4-oxo-spiro[2H-(1,3)-benzoxazine-2,3'-piperidin]-6-yl}-N-(tetrahydro-pyran-2-yloxy)-acrylamide (60 mg) as a light yellow solid.

Y=17% over 2 step

LC-MS: (ES+) MH⁺: 496

¹H NMR (300 MHz, DMSO-d₆) δ (ppm) 11.12 (bs, 1H), 8.66 (s, 1H), 7.87 (d, J=2.05 Hz, 1H), 7.73 (dd, J=7.78, 1.32 Hz, 1H), 7.47 (d, J=15.85 Hz, 1H), 7.26 (m, 2H), 7.09 (d, J=8.51 Hz, 1H), 7.01 (m, 2H), 6.46 (d, J=16.14 Hz, 1H), 4.91 (bs, 1H), 3.84-4.07 (m, 1H), 3.50-3.65 (m, 1H), 3.55 (d, J=13.50 Hz, 1H), 3.40 (d, J=13.79 Hz, 1H), 2.80 (d, J=11.15

Hz, 1H), 2.55-2.67 (m, 1H), 2.22 (d, J=11.74 Hz, 1H), 2.14-2.23 (m, 1H), 1.43-2.03 (m, 10H).

Step D

A solution of (±)-(E)-3-{1'-(4-fluoro-benzyl)-3,4-dihydro-4-oxo-spiro[2H-(1,3)-benzoxazine-2,3'-piperidin]-6-yl}-N-(tetrahydro-pyran-2-yloxy)-acrylamide (45 mg, 0.091 mmol) in DCM (5 ml) was treated with 4 M HCl in dioxane (0.5 ml) as described in Example 30, STEP C to give (±)-(E)-3-{1'-(4-fluoro-benzyl)-3,4-dihydro-4-oxo-spiro[2H-(1,3)-benzoxazine-2,3'-piperidin]-6-yl}-N-hydroxy-acrylamide (25 mg, hydrochloride salt) as a white solid.

Y=61%, purity 93%

LC-MS: Method C, rt=2.95; (ES+) MH+: 412

$^1$H NMR (300 MHz, DMSO-$d_6$) δ (ppm) 10.72 (bs, 1H), 10.33 (bs, 1H), 9.01 (s, 1 H), 7.87 (s, 1H), 7.77 (dd, J=8.66, 1.91 Hz, 1H), 7.59 (m, 2H), 7.45 (d, J=15.55 Hz, 1H), 7.28 (d, J=8.51 Hz, 1H), 7.21 (m, 2H), 6.44 (d, J=16.14 Hz, 1H), 4.31-4.47 (m, 1H), 4.17-4.31 (m, 1H), 3.30-3.56 (m, 2H), 2.78-3.05 (m, 2H), 2.01-2.25 (m, 2H), 1.71-2.00 (m, 2H).

Example 43

(±)-(E)-3-{1'-(2-Phenyl-ethyl)-3,4-dihydro-4-oxo-spiro[2H-(1,3)-benzoxazine-2,3'-piperidin]-6-yl}-N-hydroxy-acrylamide

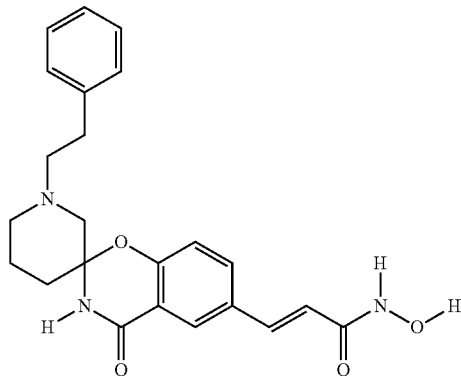 [SMILES: O=C(/C=C/c1ccc2c(c1)C(=O)NC1(CCCN(CCc3ccccc3)C1)O2)NO]

Step A (±)-(E)-3-{1'-(2-Phenyl-ethyl)-3,4-dihydro-4-oxo-spiro[2H-(1,3)-benzoxazine-2,3'-piperidin]-6-yl}-acrylic acid methyl ester was synthesized starting from Intermediate 5 (339 mg, 1.00 mmol), according to the procedure described in Example 40, Step A, using phenylacetaldehyde (0.13 ml, 1.2 mmol) and NaBH$_3$CN (63 mg, 1.2 mmol). The product was obtained as a yellow solid (320 mg).

Y=79%

LC-MS: (ES+) MH+: 407

$^1$H NMR (300 MHz, DMSO-$d_6$) δ (ppm) 8.61 (s, 1H), 8.02 (d, J=2.05 Hz, 1H), 7.91 (dd, J=8.66, 2.20 Hz, 1H), 7.68 (d, J=16.14 Hz, 1H), 7.08-7.31 (m, 5H), 7.02 (d, J=8.51 Hz, 1H), 6.57 (d, J=16.14 Hz, 1H), 3.72 (s, 3H), 2.95 (d, J=11.44 Hz, 1H), 2.54-2.77 (m, 5H), 2.13-2.43 (m, 2H), 1.49-2.06 (m, 4H).

Step B

A solution of (±)-(E)-3-{1'-(2-phenyl-ethyl)-3,4-dihydro-4-oxo-spiro[2H-(1,3)-benzoxazine-2,3'-piperidin]-6-yl}-acrylic acid methyl ester (300 mg, 0.73 mmol) in water (2.5 ml) and dioxane (5 ml) was treated with 1 M NaOH (0.96 ml) as described in Example 30, Step A to give (±)-(E)-3-{1'-(2-phenyl-ethyl)-3,4-dihydro-4-oxo-spiro[2H-(1,3)-benzoxazine-2,3'-piperidin]-6-yl}-acrylic acid as a white said [LC-MS: (ES+) MH+: 393]. The acrylic acid was suspended in DCM (5 ml), treated with TEA (0.15 ml, 1.1 mmol) and then with EDC (208 mg, 1.09 mmol), HOBt (147 mg, 1.09 mmol) and NH$_2$OTHP (102 mg, 0.871 mmol) following the procedure described in Example 30, Step B, giving (±)-(E)-3-{1'-(2-phenyl-ethyl)-3,4-dihydro-4-oxo-spiro[2H-(1,3)-benzoxazine-2,3'-piperidin]-6-yl}-N-(tetrahydro-pyran-2-yloxy)-acrylamide (165 mg) as a light yellow solid.

Y=46% over 2 steps.

LC-MS: (ES+) MH+: 492

$^1$H NMR (300 MHz, DMSO-$d_6$) δ (ppm) 11.13 (bs, 1H), 8.57 (s, 1H), 7.95 (d, J=2.35 Hz, 1H), 7.61-7.82 (m, 1H), 7.49 (d, J=15.55 Hz, 1H), 7.08-7.29 (m, 5H), 7.01 (d, J=8.22 Hz, 1H), 6.48 (d, J=16.14 Hz, 1H), 4.91 (bs, 1H), 3.83-4.14 (m, 1 H), 3.44-3.70 (m, 1H), 2.95 (d, J=11.74 Hz, 1H), 2.54-2.71 (m, 5H), 2.33 (d, J=11.74 Hz, 1H), 2.12-2.25 (m, 1H), 1.88-2.01 (m, 1H), 1.30-1.83 (m, 9H).

Step D (±)-(E)-3-{1'-(2-Phenyl-ethyl)-3,4-dihydro-4-oxo-spiro[2H-(1,3)-benzoxazine-2,3'-piperidin]-6-yl}-N-(tetrahydro-pyran-2-yloxy)-acrylamide (150 mg, 0.30 mmol) in DCM (5 ml) was treated with 4 M HCl in dioxane (1 ml) as described in Example 30, STEP C to give (±)-(E)-3-{1'-(2-phenyl-ethyl)-3,4-dihydro-4-oxo-spiro[2H-(1,3)-benzoxazine-2,3'-piperidin]-6-yl}-N-hydroxy-acrylamide (90 mg) as a pale yellow solid (hydrochloride salt).

Y=68%, purity 96%

LC-MS: Method C, rt=3.09; (ES+) MH+: 408

$^1$H NMR (300 MHz, DMSO-$d_6$) δ (ppm) 10.71 (bs, 1H), 10.29 (bs, 1H), 9.13 (s, 1 H), 7.95 (d, J=2.05 Hz, 1H), 7.79 (dd, J=8.22, 1.76 Hz, 1H), 7.48 (d, J=15.55 Hz, 1H), 7.32 (d, J=8.51 Hz, 1H), 7.11-7.30 (m, 5H), 6.47 (d, J=15.85 Hz, 1H), 3.89 (d, J=12.62 Hz, 1H), 3.52 (d, J=11.44 Hz, 1H), 3.21-3.37 (m, 2H), 2.77-3.21 (m, 4H), 2.08-2.33 (m, 2H), 1.71-2.08 (m, 2H).

Example 44

(E)-3-[1'-(1-Methyl-1H-indol-3-ylmethyl)-4-oxo-spiro(chromane-2,3'-azetidine)-6-yl]-N-hydroxy-acrylamide

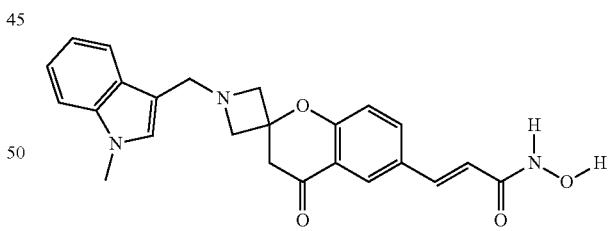

Step A

TEA (0.11 ml, 0.77 mmol) was added to a suspension of Intermediate 4 (240 mg, 0.77 mmol) in DCM (10 ml). The mixture was stirred at RT for 10 min and then the pH value was adjusted to 5 with AcOH. The mixture was treated with N-methyl-indol-3-carbaldehyde (148 mg, 0.93 mmol) and NaBH(OAc)$_3$ (197 mg, 0.93 mmol) following the procedure described in Example 31, Step A, giving (E)-3-[1'-(1-methyl-1H-indol-3-ylmethyl)-4-oxo-spiro(chromane-2,3'-azetidine)-6-yl]-acrylic acid methyl ester (220 mg) as a light orange oil.

Y=69%

LC-MS: (ES+) MH+: 417

¹H-NMR (300 MHz, DMSO-d₆) δ (ppm) 7.93-8.07 (m, 2H), 7.66 (d, J=16.14 Hz, 1H), 7.54-7.61 (m, 1H), 7.37 (d, J=8.22 Hz, 1H), 7.22 (s, 1H), 7.07-7.18 (m, 2H), 7.02 (ddd, J=7.85, 6.97, 1.03 Hz, 1H), 6.57 (d, J=15.85 Hz, 1H), 3.78 (s, 2H), 3.73 (s, 3H), 3.72 (s, 3H), 3.35 (d, J=8.51 Hz, 2H), 3.21 (d, J=8.80 Hz, 2H), 3.11 (s, 2H).

Step B (E)-3-[1'-(1-Methyl-1H-Indol-3-ylmethyl)-4-oxo-spiro(chromane-2,3'-azetidine)-6-yl]-acrylic acid methyl ester (220 mg, 0.53 mmol) was hydrolyzed with 1 M NaOH (0.68 ml) following the procedure described in Example 30, Step A, giving (E)-3-[1'-(1-methyl-1H-indol-3-ylmethyl)-4-oxo-spiro(chromane-2,3'-azetidine)-6-yl]-acrylic acid (180 mg) as a brown solid.

Y=85%

LC-MS: (ES+) MH⁺-143: 259

¹H-NMR (300 MHz, DMSO-d₆) δ (ppm) 12.28 (bs, 1H), 7.96 (dd, J=8.51, 2.35 Hz, 1H), 7.94 (d, J=2.05 Hz, 1H), 7.59-7.66 (m, 1H), 7.59 (d, J=15.85 Hz, 1H), 7.39 (d, J=8.22 Hz, 1H), 7.28 (bs, 1H), 6.99-7.20 (m, 3H), 6.46 (d, J=15.85 Hz, 1H), 3.81-3.99 (m, 2H), 3.74 (s, 3H), 3.36-3.54 (m, 4H), 3.14 (s, 2H).

Step C

A suspension of (E)-3-[1'-(1-methyl-1H-indol-3-ylmethyl)-4-oxo-spiro(chromane-2,3'-azetidine)-6-yl]-acrylic acid (180 mg, 0.447 mmol) in DCM (5 ml) was treated with TEA (0.09 ml, 0.67 mmol) and then with EDC (128 mg, 0.67 mmol), HOBt (90 mg, 0.67 mmol) and NH₂OTHP (67 mg, 0.57 mmol) following the procedure described in Example 30, Step B, giving (E)-3-[1'(1-methyl-1H-indol-3-ylmethyl)-4-oxo-spiro(chromane-2,3'-azetidine)-6-yl]-N-(tetrahydro-pyran-2-yloxy)-acrylamide (102 mg) as a white solid.

Y=45%

LC-MS: (ES+) MH⁺: 502

¹H-NMR (300 MHz, DMSO-d₆) δ (ppm) 11.13 (bs, 1H), 7.90 (d, J=2.35 Hz, 1H), 7.80 (d, J=7.63 Hz, 1H), 7.59 (d, J=7.63 Hz, 1H), 7.47 (d, J=15.85 Hz, 1H), 7.37 (d, J=8.22 Hz, 1H), 7.23 (s, 1H), 7.09-7.18 (m, 2H), 6.88-7.06 (m, 1H), 6.47 (d, J=16.14 Hz, 1H), 4.90 (bs, 1H), 3.84-4.06 (m, 1H), 3.79 (s, 2H), 3.73 (s, 3H), 3.48-3.62 (m, 1H), 3.36 (d, J=8.22 Hz, 2H), 3.21 (d, J=8.22 Hz, 2H), 3.11 (s, 2 H), 1.39-1.89 (m, 6H).

Step D (E)-3-[1'-(1-Methyl-1H-indol-3-ylmethyl)-4-oxo-spiro(chromane-2,3'-azetidine)-6-yl]-N-(tetrahydro-pyran-2-yloxy)acrylamide (102 mg, 0.203 mmol) in DCM (5 ml) was treated with 4 M HCl in dioxane (1 ml) as described in Example 30, Step C, giving (E)-3-[1'-(1-methyl-1H-indol-3-ylmethyl)-4-oxo-spiro(chromane-2,3'-azetidine)-6-yl]-N-hyroxy-acrylamide (85 mg, hydrochloride salt) as a light brown solid.

Y=94%, purity 96%

LC-MS: Method H, rt=1.62; (ES+) MH⁺: 418

¹H-NMR (300 MHz, DMSO-d₆) δ (ppm) 10.94 (bs, 1H), 10.72 (s, 1H), 9.02 (bs, 1 H), 7.73-7.97 (m, 3H), 7.37-7.69 (m, 3H), 7.19-7.31 (m, 1H), 7.04-7.19 (m, 2H), 6.45 (d, J=15.85 Hz, 1H), 4.54-4.71 (m, 2H), 4.34-4.50 (m, 1H), 4.25-4.34 (m, 2 H), 4.08-4.25 (m, 1H), 3.81 (s, 3H), 3.33 (bs, 2H).

Example 45

(±)-(E)-3-[1'-(1-Methyl-1H-indol-3-ylmethyl)-4-oxo-spiro(chromane-2,3'-piperidine)-6-yl]-N-hydroxy-acrylamide

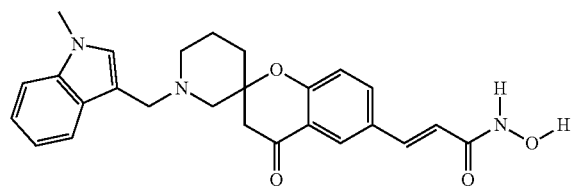 [SMILES: Cn1cc(CN2CCCC3(CC(=O)c4cc(/C=C/C(=O)NO)ccc4O3)C2)c2ccccc21]

Step A

TEA (0.14 ml, 1.0 mmol) was added to suspension of Intermediate 2 (290 mg, 0.86 mmol) in DCM (10 ml). The mixture was stirred at RT for 10 min and then the pH value was adjusted to 5 with AcOH. The mixture was treated with N-methyl-indol-3-carbaldehyde (164 mg, 1.03 mmol) and NaBH(OAc)₃ (219 mg, 1.03 mmol) following the procedure described in Example 31, A, giving (E)-3-[1'-(1-methyl-1H-indol-3-ylmethyl)-4-oxo-spiro(chromane-2,3'-piperidine)-6-yl]-acrylic acid methyl ester (380 mg) as a light orange solid.

Y=100%

LC-MS: (ES+) MH⁺: 445

¹H-NMR (300 MHz, DMSO-d₆) δ (ppm) 7.97 (dd, J=8.51, 2.35 Hz, 1H), 7.94 (d, J=2.05 Hz, 1H), 7.66 (d, J=16.14 Hz, 1H), 7.59 (d, J=7.63 Hz, 1H), 7.35 (d, J=8.22 Hz, 1H), 7.09 (s, 1H), 7.05-7.16 (m, 2H), 6.91-7.04 (m, 1H), 6.55 (d, J=16.14 Hz, 1H), 3.72 (s, 3H), 3.69 (s, 3H), 3.66 (d, J=13.50 Hz, 1H), 3.59 (d, J=13.50 Hz, 1H), 2.96 (d, J=16.73 Hz, 1H), 2.88 (d, J=16.73 Hz, 1H), 2.55-2.72 (m, 2H), 2.32-2.47 (m, 2H), 1.59-1.86 (m, 3H), 1.35-1.59 (m, 1H).

Step B

E)-3-[1'-(1-Methyl-1H-indol-3-ylmethyl)-4-oxo-spiro(chromane-2,3'-piperidine)-6-yl]-acrylic acid methyl ester (380 mg, 0.85 mmol) was hydrolyzed with 1 M NaOH (1.1 ml) following the procedure described in Example 30, Step A, giving (E)-3-[1'-(1-methyl-1H-indol-3-ylmethyl)-4-oxo-spiro(chromane-2,3'-piperidine)-6-yl]-acrylic acid (180 mg, hydrochloride salt) as a brown solid. [LC-MS: (ES+) MH⁺: 431]. The obtained acid was suspended in DCM (15 ml), treated with TEA (0.18 ml, 1.35 mmol) and then with EDC (258 mg, 1.35 mmol), HOBt (182 mg, 1.35 mmol) and NH₂OTHP (126 mg, 1.08 mmol) following the procedure described in Example 30, Step B, giving (E)-3-[1'-(1-methyl-1H-indol-3-ylmethyl)-4-oxo-spiro(chromane-2,3'-piperidine)-6-yl]-N-(tetrahydro-pyran-2-yloxy)-acrylamide (300 mg) as a light yellow solid.

Y=66% over 2 steps

LC-MS: (ES+) MH⁺: 530

¹H-NMR (300 MHz, DMSO-d₆) δ (ppm) 11.12 (bs, 1H), 7.86 (d, J=2.35 Hz, 1H), 7.73-7.81 (m, 1H), 7.60 (d, J=7.92 Hz, 1H), 7.46 (d, J=15.85 Hz, 1H), 7.35 (d, J=8.22 Hz, 1H), 6.89-7.20 (m, 4H), 6.45 (d, J=16.43 Hz, 1H), 4.66-5.06 (m, 1H), 3.87-4.04 (m, 1H), 3.69 (s, 3H), 3.67 (d, J=13.50 Hz, 1H), 3.60 (d, J=13.50 Hz, 1H), 3.46-3.58 (m, 1H), 2.96 (d, J=16.73 Hz, 1H), 2.88 (d, J=16.73 Hz, 1H), 2.55-2.66 (m, 2H), 2.29-2.46 (m, 2H), 1.37-1.82 (m, 10H).

Step C (E)-3-[1'-(1-Methyl-1H-indol-3-ylmethyl)-4-oxo-spiro (chromane-2,3'-piperidine)-6-yl]-N-(tetrahydro-pyran-2-yloxy)-acrylamide (300 mg, 0.56 mmol) in DCM (10 ml) was treated with 4 M HCl in dioxane (1 ml) as described in Example 30, Step C, giving (E)-3-[1'-(1-methyl-1H-indol-3-ylmethyl)-4-oxo-spiro(chromane-2,3'-piperidine)-6-yl]-N-hydroxy-acrylamide (215 mg, hydrochloride salt) as a light brown solid.

Y=80%, purity 98%

LC-MS: Method C, rt=3.67; (ES+) MH$^+$: 446

$^1$H-NMR (300 MHz, DMSO-d$_6$) δ (ppm) 10.72 (s, 1H), 9.92 (bs, 1H), 9.01 (bs, 1 H), 7.76-7.98 (m, 3H), 7.62 (s, 1H), 7.37-7.54 (m, 2H), 7.01-7.31 (m, 3H), 6.44 (d, J=15.85 Hz, 1H), 4.36-4.61 (m, 2H), 3.83 (s, 3H), 3.71 (d, J=13.20 Hz, 1H), 3.46-3.58 (m, 1H), 3.07-3.22 (m, 1H), 2.95 (d, J=16.73 Hz, 1H), 2.83-2.91 (m, 1 H), 2.78 (d, J=16.73 Hz, 1H), 1.88-2.14 (m, 2H), 1.68-1.85 (m, 1H), 1.46-1.68 (m, 1H).

Example 46

(±)-(E)-3-{1'-(1-Methyl-1H-indol-3-ylmethyl)-4-oxo-spiro[2H-(1,3)-benzoxazine-2,3'-piperidin]-6-yl}-N-hydroxy-acrylamide

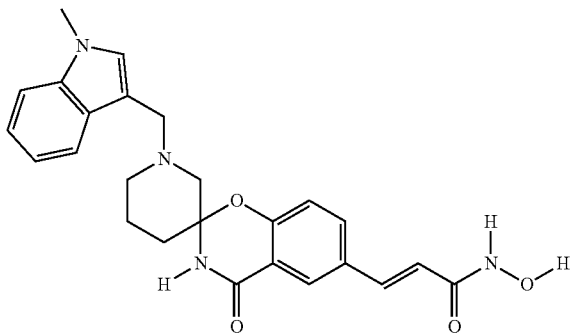 [SMILES: Cn1cc(CN2CCCC3(C2)NC(=O)c2cc(/C=C/C(=O)NO)ccc2O3)c2ccccc21]

0.1 M NaOH in MeOH (6 ml) was added to a suspension of Intermediate 5 (430 mg, 1.27 mmol) in MeOH (5 ml) and the mixture was stirred for 10 min. The pH value was adjusted to 5 with AcOH and the mixture was treated with N-methyl-indol-3-carbaldehyde (248 mg, 1.56 mmol) and NaBH$_3$CN (98 mg, 1.6 mmol), following the procedure described in Example 40, Step A to give the (±)-(E)-3-{1-(1-methyl-1H-indol-3-ylmethyl)-4-oxo-spiro[2H-(1,3)-benzoxazine-2,3'-piperidin]-6-yl}-acrylic acid methyl ester (250 mg) as a brown solid.

Y=44%

LC-MS: (ES+) MH$^+$: 446

$^1$H-NMR (300 MHz, DMSO-d$_6$) δ (ppm) 8.58 (s, 1H), 7.96 (d, J=2.05 Hz, 1H), 7.88 (dd, J=8.66, 2.20 Hz, 1H), 7.66 (d, J=16.14 Hz, 1H), 7.59 (d, J=7.92 Hz, 1H), 7.33 (d, J=8.22 Hz, 1H), 7.11 (ddd, J=8.22, 7.04, 1.17 Hz, 1H), 7.07 (s, 1H), 7.04 (d, J=8.51 Hz, 1H), 6.94-7.02 (m, 1H), 6.55 (d, J=16.14 Hz, 1H), 3.73 (s, 3 H), 3.66 (s, 3H), 3.63 (s, 2H), 2.94 (d, J=10.86 Hz, 1H), 2.60-2.71 (m, 1H), 2.07-2.34 (m, 2H), 1.48-2.07 (m, 4H).

Step B (±)-(E)-3-{1'-(1-Methyl-1H-indol-3-ylmethyl)-4-oxo-spiro[2H-(1,3)-benzoxazine-2,3'-piperidin]-6-yl}-acrylic acid methyl ester (250 mg, 0.561 mmol) was hydrolyzed with 1 M NaOH (0.73 ml) following the procedure described in Example 30, Step A, giving (E)-3-[1'-(1-methyl-1H-indol-3-ylmethyl)-4-oxo-spiro(chromane-2,3'-azetidine)-6-yl]-acrylic acid (150 mg) as a brown solid.

Y=62%

LC-MS: (ES+) MH$^+$: 432

$^1$H-NMR (300 MHz, DMSO-d$_6$) δ (ppm) 12.33 (bs, 1H), 8.57 (bs, 1H), 7.76-8.04 (m, 2H), 7.48-7.73 (m, 2H), 6.94-7.45 (m, 5H), 6.44 (d, J=15.85 Hz, 1H), 3.65-3.95 (m, 5H), 2.81-3.09 (m, 1H), 2.54-2.70 (m, 1H), 2.03-2.39 (m, 2H), 1.47-2.02 (m, 4H).

Step C

A suspension of (±)-(E)-3-{1'-(1-methyl-1H-indol-3-ylmethyl)-4-oxo-spiro[2H-(1,3)-benzoxazine-2,3'-piperidin]-6-yl}-acrylic acid (150 mg, 0.348 mmol) in DCM (4 ml) was treated with TEA (0.070 ml, 0.52 mmol) and then with EDC (99 mg, 0.52 mmol), HOBt (70 mg, 0.52 mmol) and NH$_2$OTHP (49 mg, 0.42 mmol) following the procedure described in Example 30, Step B, giving (±)-(E)-3-{1'-(1-methyl-1H-indol-3-ylmethyl)-4-oxo-spiro[2H-(1,3)-benzoxazine-2,3'-piperidin]-6-yl}-N-(tetrahydro-pyran-2-yloxy)acrylamide as a white solid [LC-MS: (ES+) MH$^+$: 531]. The solid was suspended in DCM (5 ml) and treated with 4 M HCl in dioxane (1 ml) as described in Example 30, Step C to give, after purification by preparative HPLC, (±)-(E)-3-[1'(1-methyl-1H-indol-3-ylmethyl)-4-oxo-spiro[2H-(1,3)-benzoxazine-2,3'-piperidin]-6-yl]-N-hyroxy-acrylamide (40 mg, trifluoroacetic salt) as a brown solid.

Y=21% over two steps, purity=95%

LC-MS: Method H, rt=1.47; (ES+) MH$^+$: 447

$^1$H-NMR (300 MHz, DMSO-d$_6$) δ (ppm) 10.71 (bs, 1H), 9.65 (bs, 1H), 9.03 (bs, 1 H), 8.94 (s, 1H), 7.91 (d, J=1.47 Hz, 1H), 7.67-7.85 (m, 2H), 7.35-7.61 (m, 2H), 7.00-7.34 (m, 3H), 6.44 (d, J=15.55 Hz, 1H), 4.51 (bs, 2H), 3.83-3.93 (m, 1H), 3.80 (s, 3H), 3.47-3.61 (m, 1H), 2.81-3.06 (m, 2H), 1.85-2.21 (m, 3H), 1.64-1.83 (m, 1H).

Example 47

(±)-(E)-3-[1'-(1-Methyl-1H-indol-3-ylmethyl)-4-oxo-spiro(chromane-2,4'-azepane)-6-yl]-N-hydroxy-acrylamide

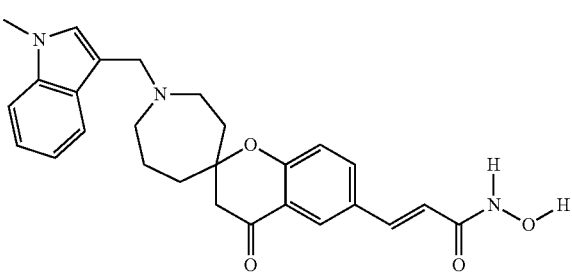 [SMILES: Cn1cc(CN2CCCC3(CC2)CC(=O)c2cc(/C=C/C(=O)NO)ccc2O3)c2ccccc21]

Step A

TEA (0.14 ml, 1.0 mmol) was added to suspension of Intermediate 3 (350 mg, 1.00 mmol) in DCM (10 ml). The mixture was stirred at RT for 10 min and then the pH value was adjusted to 5 with AcOH. The mixture was treated with N-methyl-indol-3-carbaldehyde (191 mg, 1.20 mmol) and NaBH(OAc)$_3$ (255 mg, 1.20 mmol) following the procedure described in Example 23, Step A, giving (±)-(E)-3-[1-(1-methyl-1H-indol-3-ylmethyl)-4-oxo-spiro(chromane-2,4'-azepane)-6-yl]-acrylic acid methyl ester (350 mg) as a light orange solid.

Y=76%

LC-MS: (ES+) MH+: 459

¹H-NMR (300 MHz, CHLOROFORM-d) δ (ppm) 7.97-8.09 (m, 1H), 7.47-7.75 (m, 5H), 7.29-7.42 (m, 2H), 7.13-7.24 (m, 1H), 6.38 (d, J=15.85 Hz, 1H), 3.83 (s, 2H), 3.82 (s, 3H), 3.82 (s, 3H), 2.80 (s, 2H), 1.68-2.53 (m, 10H).

Step B (±)-(E)-3-[1'-(1-Methyl-1H-indol-3-ylmethyl)-4-oxo-spiro(chromane-2,4'-azepane)-6-yl]-acrylic acid methyl ester (350 mg, 0.76 mmol) was hydrolyzed with 1 M NaOH (0.99 ml) following the procedure described in Example 30, Step A, giving ((±)-(E)-3-[1'-(1-methyl-1H-indol-3-ylmethyl)-4-oxo-spiro(chromane-2,4'-azepane)-6-yl]-acrylic acid as a white solid [LC-MS: (ES+) MH+: 445]. The obtained acid was suspended in DCM (15 ml), treated with TEA (0.16 ml, 1.14 mmol) and then with EDC (218 mg, 1.14 mmol), HOBt (154 mg, 1.14 mmol) and NH₂OTHP (106 mg, 0.905 mmol) following the procedure described in Example 30, Step B, giving (±)-(E)-3-[1'(1-methyl-1H-indol-3-ylmethyl)-4-oxo-spiro(chromane-2,4'-azepane)-6-yl]-N-(tetrahydro-pyran-2-yloxy)-acrylamide (280 mg) as a light yellow solid.

Y=68% over 2 steps

LC-MS: (ES+) MH+: 544

¹H-NMR (300 MHz, DMSO-d₆) δ (ppm) 11.11 (bs, 1H), 7.82-8.04 (m, 2H), 7.72-7.82 (m, 1H), 7.63-7.72 (m, 1H), 7.46 (d, J=15.85 Hz, 1H), 7.32-7.42 (m, 1H), 6.91-7.32 (m, 3H), 6.45 (d, J=15.55 Hz, 1H), 4.90 (bs, 1H), 3.87-4.09 (m, 1H), 3.76 (s, 3H), 3.70 (bs, 2H), 3.47-3.62 (m, 1H), 2.89 (s, 2H), 2.54-2.77 (m, 4H), 1.65-2.20 (m, 6H), 1.39-1.75 (m, 6H).

Step C (±)-(E)-3-[1'-(1-Methyl-1H-indol-3-ylmethyl)-4-oxo-spiro(chromane-2,4'-azepane)-6-yl]-N-(tetrahydro-pyran-2-yloxy)-acrylamide (280 mg, 0.51 mmol) in DCM (5 ml) was treated with 4 M HCl in dioxane (1 ml) as described in Example 30, Step C, giving after purification by preparative HPLC (±)-(E)-3-[1-(1-methyl-1H-indol-3-ylmethyl)-4-oxo-spiro(chromane-2,4'-azepane)-6-yl]-N-hydroxy-acrylamide (80 mg, trifluoroacetate salt) as a light brown solid.

Y=37%, purity 99%

LC-MS: Method H, rt=1.75; (ES+) MH+: 460

¹H-NMR (300 MHz, DMSO-d₆) δ (ppm) 10.64 (bs, 1H), 8.99 (bs, 1H), 7.86 (d, J=1.76 Hz, 1H), 7.74 (dd, J=8.80, 1.76 Hz, 1H), 7.67 (d, J=7.92 Hz, 1H), 7.42 (d, J=15.55 Hz, 1H), 7.39 (d, J=8.22 Hz, 1H), 7.24 (s, 1H), 7.15 (t, 1H), 7.03 (d, J=8.51 Hz, 1H), 6.97-7.08 (m, 1H), 6.39 (d, J=15.55 Hz, 1H), 3.80 (s, 2H), 3.75 (s, 3H), 2.91 (d, J=16.43 Hz, 1H), 2.85 (d, J=16.73 Hz, 1H), 2.60-2.80 (m, 4H), 1.84-2.13 (m, 4H), 1.64-1.84 (m, 1H), 1.42-1.64 (m, 1H).

Example 48

(±)-(E)-3-[1'-Ethyl-4-oxo-spiro(chromane-2,3'-piperidine)-6-yl]-N-hydroxy-acrylamide

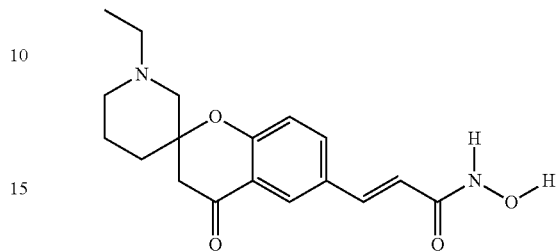

The title compound was obtained starting from (±)-(E)-3-[4-oxo-spiro(chromane-2,3'-piperidine)-6-yl]-acrylic acid methyl ester hydrochloride (Intermediate 2) and acetaldehyde following the experimental procedure described for Example 19. The title compound was obtained as its hydrochloride salt.

LC-MS: Method I, rt=1.70; (ES+) MH+: 331

¹H NMR (300 MHz, DMSO-d₆) δ (ppm): 10.73 (bs, 1H), 9.81 (bs, 1H), 7.91 (d, J=2.05 Hz, 1H), 7.84 (dd, J=8.66, 1.91 Hz, 1H), 7.45 (d, J=15.85 Hz, 1H), 7.25 (d, J=8.51 Hz, 1H), 6.47 (d, J=15.85 Hz, 1H), 3.75 (d, J=13.50 Hz, 1H), 3.37-3.52 (m, 1H), 3.07-3.35 (m, 4H), 3.03 (d, J=17.02 Hz, 1H), 2.82 (d, J=17.02 Hz, 1H), 1.88-2.26 (m, 2H), 1.52-1.87 (m, 2H), 1.26 (t, J=7.04 Hz, 3H).

Example 49

(±)-(E)-3-[1-Isopropyl-4-oxo-spiro(chromane-2,3'-piperidine)-6-yl]-N-hydroxy-acrylamide

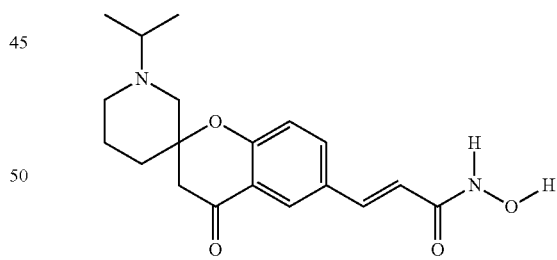

Step A

A mixture of (±)-(E)-3-[4-oxo-spiro(chromane-2,3'-piperidine)-6-yl]-acrylic acid methyl ester hydrochloride (Intermediate 2, 300 mg, 0.888 mmol), 2-iodopropane (302 mg, 1.76 mmol) and K₂CO₃ (491 mg, 3.55 mmol) in CH₃CN (40 ml) was stirred at 75° C. for 24 h. The solvent was removed and the residue was partitioned between EtOAc and H₂O. The organic layer was dried over Na₂SO₄ and evaporated to dryness. The crude mixture was purified by column chromatography (eluent: DCM/MeOH 98:2) to give (±)-(E)-3-[1'-isopropyl-4-oxo-spiro(chromane-2,3'-piperidine)-6-yl]-acrylic acid methyl ester (252 mg).

Y=83%

¹H NMR (300 MHz, DMSO-$d_6$) δ (ppm): 7.97 (d, J=2.35 Hz, 1H), 7.96 (dd, J=9.10, 2.35 Hz, 1H), 7.66 (d, J=16.14 Hz, 1H), 7.07 (d, J=9.39 Hz, 1H), 6.55 (d, J=16.14 Hz, 1H), 3.72 (s, 3H), 3.03 (d, J=16.73 Hz, 1H), 2.86 (d, J=16.73 Hz, 1H), 2.70 (spt, J=6.46 Hz, 1H), 2.60 (d, J=11.44 Hz, 1H), 2.45 (d, J=11.44 Hz, 1H), 2.31-2.45 (m, 2H), 1.62-1.86 (m, 3H), 1.35-1.60 (m, 1H), 0.88 (d, J=6.75 Hz, 3H), 0.87 (d, J=6.46 Hz, 3H).

Step B (±)-(E)-3-[1'-Isopropyl-4-oxo-spiro(chromane-2,3'-piperidine)-6-yl]-acrylic acid methyl ester (234 mg, 0.681 mmol) was treated with 1 M NaOH according to the procedure described in Example 16 STEP B to give (±)-(E)-3-[1'-isopropyl-4-oxo-spiro(chromane-2,3'-piperidine)-6-yl]-acrylic acid. The acid was treated with $NH_2$OTHP according to the procedure described in Example 16, Step C, giving (±)-(E)-3-[1'-isopropyl-4-oxo-spiro(chromane-2,3'-piperidine)-6-yl]-N-(tetrahydro-pyran-2-yloxy)-acrylamide. Removal of the THP protecting group following the procedure described in Example 16, Step C, gave (±)-(E)-3-[1'-isopropyl-4-oxo-spiro(chromane-2,3'-piperidine)-6-yl]-N-hydroxy-acrylamide hydrochloride as yellow powder (210 mg, 81% over three steps)

LC-MS: Method C, rt=2.48; (ES+) MH$^+$: 345

¹H NMR (300 MHz, DMSO-$d_6$) δ (ppm): 10.62 (bs, 1H), 9.61 (bs, 1H), 7.92 (d, J=2.05 Hz, 1H), 7.85 (dd, J=8.66, 1.91 Hz, 1H), 7.45 (d, J=15.85 Hz, 1H), 7.29 (d, J=8.51 Hz, 1H), 6.46 (d, J=15.85 Hz, 1H), 3.63 (d, J=12.32 Hz, 1H), 3.44-3.55 (m, 1H), 3.18-3.40 (m, 2H), 3.05 (d, J=17.02 Hz, 1H), 2.92-3.06 (m, 1H), 2.81 (d, J=17.02 Hz, 1H), 1.90-2.23 (m, 2H), 1.57-1.85 (m, 2H), 1.28 (d, J=6.46 Hz, 3H), 1.26 (d, J=6.75 Hz, 3H).

Y=87%

¹H NMR (300 MHz, DMSO-$d_6$) δ (ppm): 7.97 (d, J=2.35 Hz, 1H), 7.96 (dd, J=9.10, 2.35 Hz, 1H), 7.66 (d, J=16.14 Hz, 1H), 7.08 (d, J=9.39 Hz, 1H), 6.55 (d, J=15.85 Hz, 1H), 3.72 (s, 3H), 3.01 (d, J=16.73 Hz, 1H), 2.84 (d, J=16.73 Hz, 1H), 2.53-2.63 (m, 3H), 2.23-2.47 (m, 2H), 1.35-1.86 (m, 10H), 1.14-1.32 (m, 2H).

Step B (±)-(E)-3-[1'-Cyclopentyl-4-oxo-spiro(chromane-2,3'-piperidine)-6-yl]-acrylic acid methyl ester (260 mg, 0.704 mmol) was treated with 1 M NaOH according to the procedure described in Example 16 STEP B to give (±)-(E)-3-[1'-cyclopentyl-4-oxo-spiro(chromane-2,3'-piperidine)-6-yl]-acrylic acid. The acid was treated with $NH_2$OTHP according to the procedure described in Example 16, Step C, giving (±)-(E)-3-[1'-cyclopentyl-4-oxo-spiro(chromane-2,3'-piperidine)-6-yl]-N-(tetrahydro-pyran-2-yloxy)-acrylamide. Removal of the THP protecting group following the procedure described in Example 16, Step C, gave (±)-(E)-3-[1-cyclopentyl-4-oxo-spiro(chromane-2,3'-piperidine)-6-yl]-N-hydroxy-acrylamide hydrochloride as pale brown solid (109 mg, 38% over three steps).

LC-MS: Method C, rt=2.78; (ES+) MH$^+$: 371

¹H NMR (300 MHz, DMSO-$d_6$) δ (ppm): 10.72 (bs, 1H), 9.95 (bs, 1H), 7.92 (d, J=2.05 Hz, 1H), 7.85 (dd, J=8.51, 1.76 Hz, 1H), 7.45 (d, J=15.85 Hz, 1H), 7.26 (d, J=8.51 Hz, 1H), 6.46 (d, J=15.85 Hz, 1H), 3.75 (d, J=12.62 Hz, 1H), 3.43-3.62 (m, 2H), 3.28 (dd, 1H), 3.09 (d, J=17.02 Hz, 1H), 2.83-2.98 (m, 1H), 2.76 (d, J=17.02 Hz, 1H), 1.83-2.18 (m, 4H), 1.36-1.83 (m, 8H).

Example 50

(±)-(E)-3-[1'-Cyclopentyl-4-oxo-spiro(chromane-2,3'-piperidine)-6-yl]-N-hydroxy-acrylamide

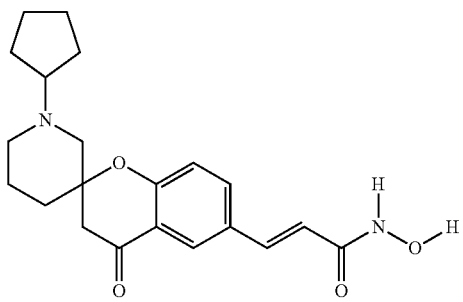 [SMILES: O=C(/C=C/c1ccc2c(c1)C(=O)CC1(CCCN(C3CCCC3)C1)O2)NO]

Step A

A mixture of (±)-(E)-3-[4-oxo-spiro(chromane-2,3'-piperidine)-6-yl]-acrylic acid methyl ester hydrochloride (Intermediate 2, 300 mg, 0.888 mmol), bromocyclopentane (397 mg, 2.66 mmol) and $K_2CO_3$ (491 mg, 3.55 mmol) in $CH_3CN$ (40 ml) was stirred at 75° C. Further bromocyclopentane (397 mg, 2.66 mmol) and catalytical amount of KI were added over three days. The solvent was removed and the residue was partitioned between EtOAc and $H_2O$. The organic layer was dried over $Na_2SO_4$ and evaporated to dryness. The crude product was purified by column chromatography (eluent: DCM/MeOH 98:2) to give (±)-(E)-3-[1'-cyclopentyl-4-oxo-spiro(chromane-2,3'-piperidine)-6-yl]-acrylic acid methyl ester (286 mg).

Example 51

(E)-3-(1'-Benzyl-8-fluoro-4-oxospiro[chroman-2,4'-piperidine]-6-yl)-N-hydroxy-acrylamide

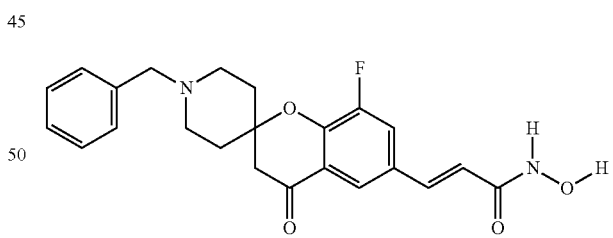

The title compound was obtained starting from (E)-3-{8-fluoro-4-oxo-spiro[chromane-2,4'-piperidine]-6-yl}-acrylic acid methyl ester (Intermediate 9) and benzaldehyde following the experimental procedure described for Example 19.

The title compound was obtained as its hydrochloride salt.

LC-MS: Method F, rt=1.40; (ES+) MH$^+$: 411

¹H NMR (300 MHz, DMSO-$d_6$) δ (ppm): 10.40-11.83 (m, 2H), 7.83 (dd, J=11.74, 1.47 Hz, 1H), 7.74 (s, 1H), 7.66 (dd, J=6.46, 2.93 Hz, 2H), 7.31-7.53 (m, 4H), 6.49 (d, J=15.85 Hz, 1H), 4.37 (d, J=4.69 Hz, 2H), 3.00-3.38 (m, 4H), 2.95 (s, 2H), 2.06-2.38 (m, 4H).

Example 52

(E)-3-(1'-Benzyl-8-methyl-4-oxospiro[chroman-2,4'-piperidine]-6-yl)-N-hydroxy-acrylamide

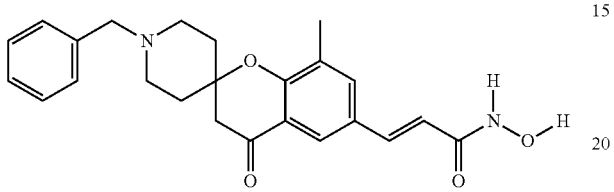

The title compound was obtained starting from methyl-4-oxo-spiro[chromane-2,4'-piperidine]-6-yl}-acrylic acid methyl ester (Intermediate 10) and benzaldehyde following the experimental procedure described for Example 19. The title compound was obtained as its hydrochloride salt.

LC-MS: Method H (Ascentis Express C18 (30×2.1 mm, 2.7 μm) column), rt=1.60; (ES+) MH$^+$: 407

$^1$H NMR (300 MHz, DMSO-d$_6$) δ (ppm): 11.00 (bs, 1H), 10.68 (bs, 1H), 7.74 (d, J=2.05 Hz, 1H), 7.57-7.72 (m, 3H), 7.44-7.54 (m, 3H), 7.38 (d, J=15.85 Hz, 1H), 6.42 (d, J=15.85 Hz, 1H), 4.39 (d, J=4.11 Hz, 2H), 3.25-3.41 (m, 2H), 2.95-3.17 (m, 2H), 2.87 (s, 2H), 2.13-2.28 (m, 4H), 2.12 (s, 3H).

Example 53

(E)-3-(1'-(4-Fluorobenzyl)-4-(methoxyimino)spiro[chroman-2,3'-piperidine]-6-yl)-N-hydroxyacrylamide

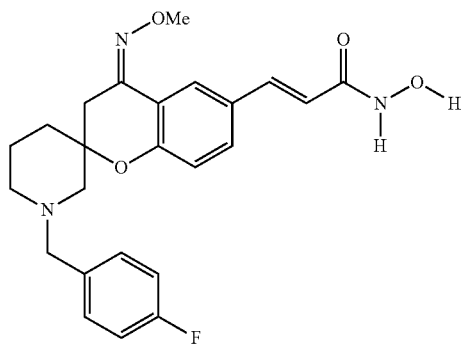 [SMILES: CO/N=C1/CC2(CCCN(Cc3ccc(F)cc3)C2)Oc2ccc(/C=C/C(=O)NO)cc21]

A mixture of (E)-3-(1'-(4-fluorobenzyl)-4-oxospiro[chroman-2,3'-piperidine]-6-yl)-N-hydroxyacrylamide hydrochloride (80 mg, 0.179 mmol) and O-methylhydroxylamine hydrochloride (32.6 mg, 0.390 mmol) in ethanol (2 ml) and pyridine (0.031 ml, 0.390 mmol) was heated at 80° C. for 2 h.

The solvent was removed in vacuo and the crude product was purified by preparative LC-MS to give the title compound (33.04 mg) as its trifluoroacetate salt.

Y=33%

LC-MS: Method J, rt 2.01 min, (ES+) MH$^+$: 440.2

$^1$H NMR (DMSO-d$_6$) δ (ppm): 10.68 (bs, 1H), 9.47 (bs, 1H), 9.01 (bs, 1H), 7.93 (bs, 1H), 7.41 (d, J=15.8 Hz, 1H), 7.25-7.67 (m, 5H), 7.04 (d, J=8.5 Hz, 1H), 6.38 (d, J=15.6 Hz, 1H), 4.21-4.53 (m, 2H), 3.96 (s, 3H), 3.43-3.56 (m, 2H), 3.09-3.33 (m, 1H), 3.00 (d, J=17.6 Hz, 1H), 2.81-2.94 (m, 1H), 2.75 (d, J=17.6 Hz, 1H), 1.40-2.08 (m, 4H).

Example 54

(E)-3-(1'-Cyclopentyl-4-(hydroxyimino)spiro[chroman-2,3'-piperidine]-6-yl)-N-hydroxyacrylamide

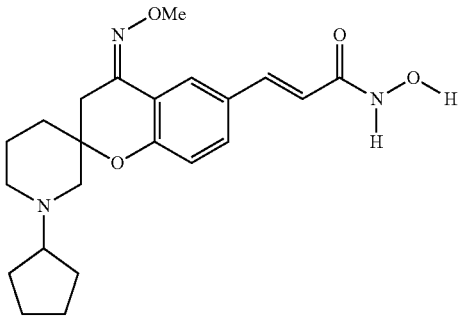 [SMILES: CO/N=C1/CC2(CCCN(C3CCCC3)C2)Oc2ccc(/C=C/C(=O)NO)cc21]

A mixture of (E)-3-(1'-cyclopentyl-4-oxospiro[chroman-2,3'-piperidine]-6-yl)-N-hydroxyacrylamide hydrochloride (80 mg, 0.197 mmol), hydroxylamine hydrochloride (27.3 mg, 0.393 mmol) and pyridine (0.032 ml, 0.393 mmol) in ethanol (2 ml) was heated at 80° C. The solvent was removed in vacuo and the crude was purified by preparative LC-MS to give the title compound (9.56 mg) as trifluoroacetate

Y=9.7%

LC-MS: Method E, rt 2.54 min; (ES+) MH$^+$: 386.2

$^1$H NMR (DMSO-d$_6$) δ (ppm): 11.57 (s, 1H), 10.68 (s, 1H), 9.18 (s, 1H), 8.99 (bs, 1H), 7.97 (s, 1H), 7.51-7.67 (m, 1H), 7.42 (d, J=15.6 Hz, 1H), 7.04 (d, J=9.4 Hz, 1H), 6.36 (d, J=16.1 Hz, 1H), 3.40-3.77 (m, 3H), 2.61-3.19 (m, 4H), 1.30-2.15 (m, 12H).

Example 55

(E)-3-(4-(Benzyloxyimino)-1'-phenethylspiro[chroman-2,3'-piperidine]-6-yl)-N-hydroxyacrylamide

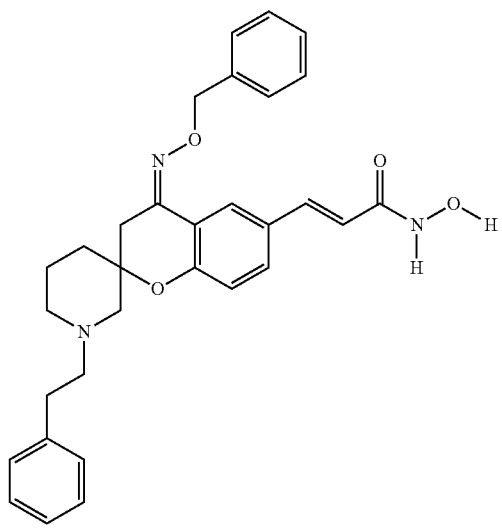 [SMILES: O=C(/C=C/c1ccc2c(c1)/C(=N\OCc1ccccc1)CC1(CCCN(CCc3ccccc3)C1)O2)NO]

A mixture of (E)-N-hydroxy-3-(4-oxo-1-phenethylspiro[chroman-2,3'-piperidine]-6-yl)acrylamide trifluoroacetate (0.05 g, 0.096 mmol) and O-benzylhydroxylamine hydrochloride (0.017 g, 0.106 mmol) in EtOH (2 ml) and pyridine (0.015 ml, 0.192 mmol) was heated at 80° C. for 4 h. The solvent was removed in vacuo and the crude was purified by preparative LC-MS to give the title compound (27 mg) as trifluoroacetate.

Y=45%

LC-MS: Method J, rt 2.80 min; (ES+) MH$^+$: 512.2

$^1$H NMR (DMSO-d$_6$) δ (ppm): 10.70 (bs, 1H), 9.43 (bs, 1H), 8.99 (bs, 1H), 7.97 (bs, 1H), 7.61 (d, J=9.1 Hz, 1H), 7.19-7.54 (m, 11H), 7.06 (d, J=8.2 Hz, 1H), 6.38 (d, J=15.8 Hz, 1H), 5.27 (s, 2H), 3.45-3.86 (m, 6H), 2.78-3.20 (m, 4H), 1.39-2.03 (m, 4H).

2. Biological Testing

Methods and Results

2.1 Assay of Enzyme Inhibition of HDAC

The in-vitro activity of HDAC inhibitors was assayed using a BIOMOL Kit, according to the instructions from the manufacturer (Biomolecular Research Laboratory). 15 µl of 30× diluted nuclear fraction of Hela cells, was diluted to 50 µl with the assay buffer containing the HDAC inhibitor and the substrate (lysine with acetylated amino group on the side chain) at a concentration of 200 µM. The samples were incubated for 15 min at RT and then exposed to a developer (10 min at RT). In this last step a fluorophore was produced, whose fluorescence was measured using an excitation wavelength of 355 nm and an emission at 460 nm. The IC$_{50}$ was calculated using GraphPad Software.

The obtained results are illustrated in the following Table 1. IC$_{50}$ results were allocated to one of 3 ranges as follows: Range A: IC$_{50}$≤0.1 µM; Range B: from 0.1 to 1.0 µM; Range C: IC$_{50}$≥1.0 µM.

TABLE 1

Results of the HDAC inhibition assay:

| Example | Biomol IC$_{50}$ [µM] |
|---|---|
| 1 | B |
| 2 | A |
| 3 | A |
| 4 | A |
| 5 | B |
| 6 | B |
| 7 | B |
| 8 | B |
| 9 | A |
| 10 | A |
| 11 | B |
| 12 | B |
| 13 | A |
| 14 | B |
| 15 | B |
| 16 | B |
| 17 | A |
| 18 | B |
| 19 | A |
| 20 | A |
| 21 | B |
| 22 | B |
| 23 | A |
| 24 | B |
| 25 | B |
| 26 | B |
| 27 | B |
| 28 | A |
| 29 | B |
| 30 | B |
| 31 | A |
| 32 | B |
| 33 | B |
| 34 | B |
| 35 | B |
| 36 | B |
| 37 | A |
| 38 | B |
| 39 | B |
| 40 | A |
| 41 | B |
| 42 | B |
| 43 | A |
| 44 | A |
| 45 | B |
| 46 | B |
| 47 | B |
| 48 | B |
| 49 | B |
| 50 | A |
| 51 | B |
| 52 | B |
| 53 | C |
| 54 | A |
| 55 | C |

2.2 Cell Growth

CellTiter-Glo® Luminescent Cell Viability Assay (Promega) is a homogeneous method of determining the number of viable cells in culture based on quantitation of the present ATP, which indicates the presence of metabolically active cells. The homogeneous assay procedure involves addition of a single reagent (CellTiter-Glo® Reagent) directly to the cells, which leads to cell lysis and generation of a luminescent signal proportional to the amount of the ATP and the number of cells present in culture. The assay relies on the properties of a proprietary thermostable luciferase (Ultra-Glo® recombinant luciferase), which generates a luminescent signal.

K562, A549, and HCT-116 cells, in exponential growth, were incubated for 72 h with different concentrations of the inhibitors. After 72 h, a volume of CellTiter-Glo® Reagent equal to the volume of cell culture medium was added. The content was mixed for 2 min to induce cell lysis. The luminescence was recorded after further 10 min at RT in order to obtain a stable luminescent signal.

The $IC_{50}$ was calculated using GraphPad Software.

The obtained results are illustrated in the following Table 2. $IC_{50}$ results were allocated to one of 3 ranges as follows: Range A: $IC_{50} \leq 1.0\ \mu M$; Range B: from 1.0 to 3.0 $\mu M$; Range C: $IC_{50} \geq 3.0\ \mu M$.

TABLE 2

Results of the antiproliferative assay:

| Example | K562 | A549 | HCT116 |
|---|---|---|---|
| 1 | C | B | B |
| 2 | A | A | A |
| 3 | A | A | A |
| 4 | A | A | A |
| 5 | C | C | C |
| 6 | A | B | A |
| 7 | A | A | A |
| 8 | A | A | A |
| 9 | A | A | A |
| 10 | A | A | A |
| 11 | A | A | A |
| 12 | A | A | A |
| 13 | A | A | A |
| 14 | A | A | A |
| 15 | A | B | A |
| 16 | C | C | C |
| 17 | A | B | A |
| 18 | A | B | A |
| 19 | A | B | A |
| 20 | A | A | A |
| 21 | B | C | B |
| 22 | C | C | B |
| 23 | A | A | A |
| 24 | C | C | C |
| 25 | B | C | A |
| 26 | A | A | A |
| 27 | B | C | B |
| 28 | A | A | A |
| 29 | A | A | A |
| 30 | B | C | C |
| 31 | A | A | A |
| 32 | A | A | A |
| 33 | A | A | A |
| 34 | A | A | A |
| 35 | A | B | A |
| 36 | C | C | C |
| 37 | A | B | A |
| 38 | B | C | B |
| 39 | B | C | B |
| 40 | A | A | A |
| 41 | A | B | A |
| 42 | A | B | A |
| 43 | A | A | A |
| 44 | A | A | A |
| 45 | A | A | A |
| 46 | A | A | A |
| 49 | A | A | A |
| 50 | A | A | A |
| 51 | A | B | A |
| 52 | A | B | A |
| 53 | B | C | B |
| 54 | A | A | A |
| 55 | A | B | A |

The invention claimed is:
1. Compounds of formula (I)

wherein:
m, n are independently zero or an integer from 1 to 4;
p is, zero or an integer from 1 to 3;
R is hydrogen; $C_1$-$C_6$ alkyl, optionally substituted by $C_3$-$C_8$ cycloalkyl, $C_6$-$C_{10}$ aryl, or hetero($C_2$-$C_9$)aryl; (CO)$R^2$; (SO$_2$)$R^3$; $C_3$-$C_8$ cycloalkyl; $C_6$-$C_{10}$ aryl or hetero($C_2$-$C_9$)aryl;
$R^1$ is halogen, $C_1$-$C_6$ alkyl, $C_1$-$C_6$ haloalkyl, $C_1$-$C_6$ alkoxy, or $C_1$-$C_6$ haloalkoxy;
Y is $CH_2$ or $NR^4$;
Z is C=$R^5$;
$R^2$ is $C_1$-$C_6$ alkyl, optionally substituted by $C_6$-$C_{10}$ aryl or by hetero($C_2$-$C_9$)aryl; $C_6$-$C_{10}$ aryl; hetero($C_2$-$C_9$)aryl; O—$C_1$-$C_6$ alkyl, optionally substituted by $C_6$-$C_{10}$ aryl; O—($C_6$-$C_{10}$-aryl) or $NR^6R^7$;
$R^3$ is $C_1$-$C_6$ alkyl, optionally substituted by $C_6$-$C_{10}$ aryl or by hetero($C_2$-$C_9$)aryl; $C_6$-$C_{10}$ aryl or hetero($C_2$-$C_9$)aryl;
$R^4$ is hydrogen; $C_1$-$C_6$ alkyl, optionally substituted by $C_6$-$C_{10}$ aryl or by hetero($C_2$-$C_9$)aryl;
$R^5$ is oxygen or $NOR^8$;
$R^6$ is hydrogen; $C_1$-$C_6$ alkyl, optionally substituted by $C_6$-$C_{10}$ aryl or by hetero($C_2$-$C_9$)aryl; $C_6$-$C_{10}$ aryl or hetero($C_2$-$C_9$)aryl;
$R^7$ is hydrogen; $C_1$-$C_6$ alkyl, optionally substituted by $C_6$-$C_{10}$ aryl or by hetero($C_2$-$C_9$)aryl; or $R^6$ and $R^7$ together with the nitrogen to which they are bound form a $C_4$-$C_9$-heterocyclic ring, optionally containing one or more further heteroatoms in the ring selected from $NR^9$, O or S;
$R^8$ is hydrogen; $C_1$-$C_6$ alkyl, optionally substituted by $C_6$-$C_{10}$ aryl;
$R^9$ is hydrogen; $C_1$-$C_6$ alkyl, optionally substituted by $C_6$-$C_{10}$ aryl or by hetero($C_2$-$C_9$)aryl; $C_6$-$C_{10}$ aryl; hetero($C_2$-$C_9$)aryl; (CO)$R^{10}$; or (SO$_2$)$R^{11}$;
$R^{10}$ is $C_1$-$C_6$ alkyl, optionally substituted by $C_6$-$C_{10}$ aryl or by hetero($C_2$-$C_9$)aryl; O—$C_1$-$C_6$ alkyl, optionally substituted by $C_6$-$C_{10}$ aryl; O—($C_6$-$C_{10}$-aryl) or $NR^{12}R^{13}$;
$R^{11}$ is $C_1$-$C_6$ alkyl, optionally substituted by $C_6$-$C_{10}$ aryl or by hetero($C_2$-$C_9$)aryl; $C_6$-$C_{10}$ aryl or hetero($C_2$-$C_9$)aryl;
$R^{12}$ is hydrogen; $C_1$-$C_6$ alkyl, optionally substituted by $C_6$-$C_{10}$ aryl or by hetero($C_2$-$C_9$)aryl; $C_6$-$C_{10}$ aryl or hetero($C_2$-$C_9$)aryl;
$R^{13}$ is hydrogen; $C_1$-$C_6$ alkyl, optionally substituted by $C_6$-$C_{10}$ aryl or hetero($C_2$-$C_9$)aryl;
and the pharmaceutically acceptable salts thereof; provided that when p is zero, then n and m cannot be both 1.
2. Compounds according to claim 1, wherein:
m, n are independently zero or an integer from 1 to 4;
p is zero or 1;
R is hydrogen; $C_1$-$C_4$ alkyl, optionally substituted by $C_3$-$C_8$ cycloalkyl, phenyl, or hetero($C_2$-$C_9$)aryl; (CO)$R^2$; $C_3$-$C_8$ cycloalkyl; phenyl; or hetero($C_2$-$C_9$)aryl;

R¹ is halogen, $C_1$-$C_4$ alkyl, $C_1$-$C_4$ haloalkyl, $C_1$-$C_4$ alkoxy, or $C_1$-$C_4$ haloalkoxy;

Y is $CH_2$ or $NR^4$;

Z is C=$R^5$;

R² is $C_1$-$C_4$ alkyl, optionally substituted by phenyl or by hetero($C_2$-$C_9$)aryl; phenyl; hetero($C_2$-$C_9$)aryl; O—$C_1$-$C_4$ alkyl; or $NR^6R^7$;

R⁴ is hydrogen; $C_1$-$C_4$ alkyl, optionally substituted by phenyl;

R⁵ is oxygen or $NOR^8$;

R⁶ is hydrogen; $C_1$-$C_4$ alkyl, optionally substituted by phenyl; or phenyl;

R⁷ is hydrogen; $C_1$-$C_4$ alkyl, optionally substituted by phenyl;

R⁸ is hydrogen; $C_1$-$C_4$ alkyl, optionally substituted by phenyl;

and the pharmaceutically acceptable salts thereof.

3. Compounds according to claim 1, selected from:

(±)-(E)-3-[4-oxo-spiro(chromane-2,3'-pyrrolidine)-6-yl]-N-hydroxy-acrylamide;

(±)-(E)-3-[1'-Benzyl-4-oxo-spiro(chromane-2,3'-pyrrolidine)-6-yl]-N-hydroxy-acrylamide;

(−)-(E)-3-[1'-Benzyl-4-oxo-spiro(chromane-2,3'-pyrrolidine)-6-yl]-N-hydroxy-acrylamide;

(+)-(E)-3-[1'-Benzyl-4-oxo-spiro(chromane-2,3'-pyrrolidine)-6-yl]-N-hydroxy-acrylamide;

(±)-(E)-3-[1'-Acetyl-4-oxo-spiro(chromane-2,3'-pyrrolidine)-6-yl]-N-hydroxy-acrylamide;

(±)-(E)-3-[1'-Benzoyl-4-oxo-spiro(chromane-2,3'-pyrrolidine)-6-yl]-N-hydroxy-acrylamide;

(±)-(E)-3-[1'-Methyl-4-oxo-spiro(chromane-2,3'-pyrrolidine)-6-yl]-N-hydroxy-acrylamide;

(±)-(E)-3-[1'-Ethyloxycarbonyl-4-oxo-spiro(chromane-2,3'-pyrrolidine)-6-yl]-N-hydroxy-acrylamide;

(±)-(E)-3-[1'-(2-Phenyl-ethyl)-4-oxo-spiro(chromane-2,3'-pyrrolidine)-6-yl]-N-hydroxy-acrylamide;

(±)-(E)-3-[1'-(1-Methyl-1H-indol-3-ylmethyl)-4-oxo-spiro(chromane-2,3'-pyrrolidine)-6-yl]-N-hydroxy-acrylamide;

(±)-(E)-3-[1'-(4-Fluoro-benzyl)-4-oxo-spiro(chromane-2,3'-pyrrolidine)-6-yl]-N-hydroxy-acrylamide;

(±)-(E)-3-[4-oxo-spiro(chromane-2,3'-piperidine)-6-yl]-N-hydroxy-acrylamide;

(±)-(E)-3-[1'-Benzyl-4-oxo-spiro(chromane-2,3'-piperidine)-6-yl]-N-hydroxy-acrylamide;

(±)-(E)-3-[1'-Methyl-4-oxo-spiro(chromane-2,3'-piperidine)-6-yl]-N-hydroxy-acrylamide;

(±)-(E)-3-[1'-Ethyloxycarbonyl-4-oxo-spiro(chromane-2,3'-piperidine)-6-yl]-N-hydroxy-acrylamide;

(±)-(E)-3-[1'-Acetyl-4-oxo-spiro(chromane-2,3'-piperidine)-6-yl]-N-hydroxy-acrylamide;

(−)-(E)-3-[1'-Benzyl-4-oxo-spiro(chromane-2,3'-piperidine)-6-yl]-N-hydroxy-acrylamide;

(+)-(E)-3-[1'-Benzyl-4-oxo-spiro(chromane-2,3'-piperidine)-6-yl]-N-hydroxy-acrylamide;

(±)-(E)-3-[1'-(4-Fluoro-benzyl)-4-oxo-spiro(chromane-2,3'-piperidine)-6-yl]-N-hydroxy-acrylamide;

(±)-(E)-3-[1'-(2-Phenyl-ethyl)-4-oxo-spiro(chromane-2,3'-piperidine)-6-yl]-N-hydroxy-acrylamide;

(±)-(E)-3-[1'-Benzoyl-4-oxo-spiro(chromane-2,3'-piperidine)-6-yl]-N-hydroxy-acrylamide;

(±)-(E)-3-[4-oxo-spiro(chromane-2,4'-azepane)-6-yl]-N-hydroxy-acrylamide;

(±)-(E)-3-[1'-Benzyl-4-oxo-spiro(chromane-2,4'-azepane)-6-yl]-N-hydroxy-acrylamide;

(±)-(E)-3-[1'-Acetyl-4-oxo-spiro(chromane-2,4'-azepane)-6-yl]-N-hydroxy-acrylamide;

(±)-(E)-3-[1'-Benzoyl-4-oxo-spiro(chromane-2,4'-azepane)-6-yl]-N-hydroxy-acrylamide;

(±)-(E)-3-[1'-Methyl-4-oxo-spiro(chromane-2,4'-azepane)-6-yl]-N-hydroxy-acrylamide;

(±)-(E)-3-[1'-Ethyloxycarbonyl-4-oxo-spiro(chromane-2,4'-azepane)-6-yl]-N-hydroxy-acrylamide;

(±)-(E)-3-[1'-(2-Phenyl-ethyl)-4-oxo-spiro(chromane-2,4'-azepane)-6-yl]-N-hydroxy-acrylamide;

(±)-(E)-3-[1'-(4-Fluoro-benzyl)-4-oxo-spiro(chromane-2,4'-azepane)-6-yl]-N-hydroxy-acrylamide;

(E)-3-[4-oxo-spiro(chromane-2,3'-azetidine)-6-yl]-N-hydroxy-acrylamide;

(E)-3-[1'-Benzyl-4-oxo-spiro(chromane-2,3'-azetidine)-6-yl]-N-hydroxy-acrylamide;

(E)-3-[1'-(2-Phenyl-ethyl)-4-oxo-spiro(chromane-2,3'-azetidine)-6-yl]-N-hydroxy-acrylamide;

(E)-3-[1'-(4-Fluoro-benzyl)-4-oxo-spiro(chromane-2,3'-azetidine)-6-yl]-N-hydroxy-acrylamide;

(E)-3-[1'-Methyl-4-oxo-spiro(chromane-2,3'-azetidine)-6-yl]-N-hydroxy-acrylamide;

(E)-3-{1-[2-(4-Fluoro-phenyl)-ethyl]-4-oxo-spiro(chromane-2,3'-azetidine)-6-yl}-N-hydroxy-acrylamide;

(E)-3-[1'-Acetyl-4-oxo-spiro(chromane-2,3'-azetidine)-6-yl]-N-hydroxy-acrylamide;

(E)-3-[1'-Benzoyl-4-oxo-spiro(chromane-2,3'-azetidine)-6-yl]-N-hydroxy-acrylamide;

(E)-3-[1'-Ethyloxycarbonyl-4-oxo-spiro(chromane-2,3'-azetidine)-6-yl]-N-hydroxy-acrylamide;

(±)-(E)-3-{3,4-Dihydro-4-oxo-spiro[2H-(1,3)-benzoxazine-2,3'-piperidin]-6-yl}-N-hydroxy-acrylamide;

(±)-(E)-3-{1'-Benzyl-3,4-dihydro-4-oxo-spiro[2H-(1,3)-benzoxazine-2,3'-piperidin]-6-yl}-N-hydroxy-acrylamide;

(±)-(E)-3-[1'-Methyl-3,4-dihydro-4-oxo-spiro[2H-(1,3)-benzoxazine-2,3'-piperidin]-6-yl]-N-hydroxy-acrylamide;

(±)-(E)-3-{1'-(4-Fluoro-benzyl)-3,4-dihydro-4-oxo-spiro[2H-(1,3)-benzoxazine-2,3'-piperidin]-6-yl}-N-hydroxy-acrylamide;

(±)-(E)-3-{1'-(2-Phenyl-ethyl)-3,4-dihydro-4-oxo-spiro[2H-(1,3)-benzoxazine-2,3'-piperidin]-6-yl}-N-hydroxy-acrylamide;

(E)-3-[1'-(1-Methyl-1H-indol-3-ylmethyl)-4-oxo-spiro(chromane-2,3'-azetidine)-6-yl]-N-hydroxy-acrylamide;

(±)-(E)-3-[1'-(1-Methyl-1H-indol-3-ylmethyl)-4-oxo-spiro(chromane-2,3'-piperidine)-6-yl]-N-hydroxy-acrylamide;

(±)-(E)-3-{1'-(1-Methyl-1H-indol-3-ylmethyl)-4-oxo-spiro[2H-(1,3)-benzoxazine-2,3'-piperidin]-6-yl}-N-hydroxy-acrylamide;

(±)-(E)-3-[1'-(1-Methyl-1H-indol-3-ylmethyl)-4-oxo-spiro(chromane-2,4'-azepane)-6-yl]-N-hydroxy-acrylamide;

(±)-(E)-3-(1'-Ethyl-4-oxospiro[chromane-2,3'-piperidine]-6-yl)-N-hydroxy-acrylamide;

(±)-(E)-3-(1'-Isopropyl-4-oxospiro[chromane-2,3'-piperidine]-6-yl)-N-hydroxy-acrylamide;

(±)-(E)-3-(1'-Cyclopentyl-4-oxospiro[chromane-2,3'-piperidine]-6-yl)-N-hydroxy-acrylamide;

(E)-3-(1'-Benzyl-8-fluoro-4-oxospiro[chromane-2,4'-piperidine]-6-yl)-N-hydroxy-acrylamide;

(E)-3-(1'-Benzyl-8-methyl-4-oxospiro[chromane-2,4'-piperidine]-6-yl)-N-hydroxy-acrylamide;

(E)-3-(1'-(4-Fluorobenzyl)-4-(methoxyimino)spiro[chroman-2,3'-piperidine]-6-yl)-N-hydroxyacrylamide;

(E)-3-(1'-Cyclopentyl-4-(hydroxyimino)spiro[chroman-2,3'-piperidine]-6-yl)-N-hydroxyacrylamide;

(E)-3-(4-(Benzyloxyimino)-1'-phenethylspiro[chroman-2,3'-piperidine]-6-yl)-N-hydroxyacrylamide.

4. Compounds as described in claim 1, for use as HDAC inhibitors.

5. Pharmaceutical composition comprising one or more compounds of formula (I) as described in claim 1.

6. Pharmaceutical composition according to claim 5, in the form of tablets, capsules, oral preparations, powders, granules, pills, injectable or infusible liquid solutions, suspensions, emulsions, suppositories, ointments, creams, lotions, gels, pastes, transdermal delivery devices.

7. Process for preparing a compound according to claim 1, in which Z is C=O, comprising the transformation of a compound of formula A1 into a compound of formula A2, and the subsequent transformation of a compound of formula A2 into a compound of formula (I), as represented in Scheme A below:

Scheme A

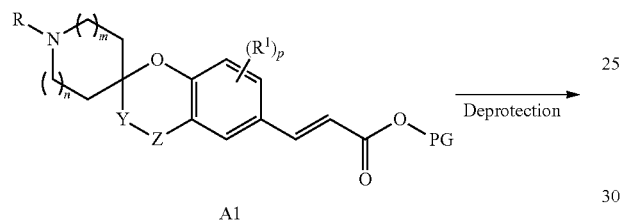

A1

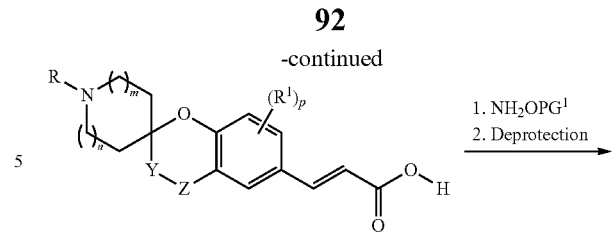

A2

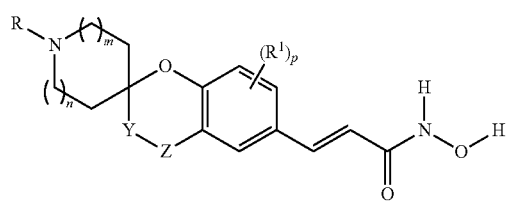

(I)

wherein:
Z is C=O
PG and $PG^1$ are protecting groups wherein PG is a methyl or tert-butyl group and
$PG^1$ is a O-(tetrahydro-2H-pyran-2-yl) group.

* * * * *